(12) United States Patent
Breault et al.

(10) Patent No.: US 6,969,714 B2
(45) Date of Patent: Nov. 29, 2005

(54) IMIDAZOLO-5-YL-2-ANILINO-PYRIMIDINES AS AGENTS FOR THE INHIBITION OF THE CELL PROLIFERATION

(75) Inventors: Gloria Anne Breault, Macclesfield (GB); Nicholas John Newcombe, Macclesfield (GB); Andrew Peter Thomas, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 222 days.

(21) Appl. No.: 10/363,655

(22) PCT Filed: Aug. 30, 2001

(86) PCT No.: PCT/GB01/03864

§ 371 (c)(1),
(2), (4) Date: Mar. 4, 2003

(87) PCT Pub. No.: WO02/20512

PCT Pub. Date: Mar. 14, 2002

(65) Prior Publication Data

US 2004/0014776 A1 Jan. 22, 2004

(30) Foreign Application Priority Data

Sep. 5, 2000 (GB) .............................................. 0021726

(51) Int. Cl.$^7$ .................... C07D 403/04; A61K 31/4178
(52) U.S. Cl. .............................. 514/235.8; 514/255.05; 514/275; 544/122; 544/331
(58) Field of Search ............................... 544/122, 331, 544/235.8, 255.05, 275

(56) References Cited

U.S. PATENT DOCUMENTS

| | | | |
|---|---|---|---|
| 4,983,608 A | 1/1991 | Effland et al. ............... | 514/216 |
| 5,516,775 A | 5/1996 | Zimmermann et al. .. | 514/224.2 |
| 5,521,184 A | 5/1996 | Zimmermann ............... | 514/252 |
| 5,610,303 A | 3/1997 | Kimura et al. ............... | 544/326 |
| 5,739,143 A | 4/1998 | Adams et al. ............... | 514/275 |
| 5,859,041 A | 1/1999 | Liverton et al. ............ | 514/396 |
| 6,593,326 B1 | 7/2003 | Bradbury et al. ......... | 514/235.8 |
| 2003/0144303 A1 * | 7/2003 | Hawley et al. .............. | 514/256 |

FOREIGN PATENT DOCUMENTS

| | | |
|---|---|---|
| CA | 2231765 | 9/1998 |
| EP | 0 135 472 | 3/1985 |
| EP | 0 363 002 | 4/1990 |
| EP | 0 379 806 B1 | 8/1990 |
| EP | 0 945 443 A1 | 9/1999 |
| WO | 91/18887 | 12/1991 |
| WO | 92/20642 | 11/1992 |
| WO | 95/09847 | 4/1995 |
| WO | 95/09851 | 4/1995 |
| WO | 95/09852 | 4/1995 |
| WO | 95/09853 | 4/1995 |
| WO | 95/15952 | 6/1995 |
| WO | 96/015177 | 2/1996 |
| WO | 96/28427 | 9/1996 |
| WO | 96/40143 | 12/1996 |
| WO | 97/19065 | 5/1997 |
| WO | 97/35856 | 10/1997 |
| WO | 97/40017 | 10/1997 |
| WO | 97/44326 | 11/1997 |
| WO | 97/47618 | 12/1997 |
| WO | 98/11095 | 3/1998 |
| WO | 98/16230 | 4/1998 |
| WO | 98/18782 | 5/1998 |
| WO | 98/25619 | 6/1998 |
| WO | 98/33798 | 8/1998 |
| WO | 98/41512 | 9/1998 |
| WO | 98/54093 | 12/1998 |
| WO | 98/56788 | 12/1998 |
| WO | 99/01136 | 1/1999 |
| WO | 99/32121 | 1/1999 |
| WO | 99/18096 | 4/1999 |
| WO | 99/18942 | 4/1999 |
| WO | 99/31073 | 6/1999 |
| WO | 99/41253 | 8/1999 |
| WO | 99/50250 | 10/1999 |
| WO | 99/50251 | 10/1999 |
| WO | 00/12485 | 3/2000 |
| WO | 00/12486 | 3/2000 |
| WO | 00/17202 | 3/2000 |
| WO | 00/49018 | 8/2000 |
| WO | 00/53595 | 9/2000 |
| WO | 00/55161 | 9/2000 |
| WO | 00/59892 | 10/2000 |
| WO | 00/78731 A1 | 12/2000 |
| WO | 01/14375 A1 | 3/2001 |
| WO | 01/29009 A1 | 4/2001 |
| WO | 01/30778 A1 | 5/2001 |
| WO | 01/37835 A | 5/2001 |
| WO | 01/47897 A1 | 7/2001 |
| WO | 01/47921 A1 | 7/2001 |
| WO | 01/60816 A1 | 8/2001 |
| WO | 01/64653 A1 | 9/2001 |
| WO | 01/64654 A1 | 9/2001 |
| WO | 01/64655 A1 | 9/2001 |
| WO | 01/64656 A1 | 9/2001 |
| WO | 01/72717 A1 | 10/2001 |
| WO | 02/04429 A1 | 1/2002 |
| WO | 02/066481 A1 | 8/2002 |
| WO | 02/096887 A1 | 12/2002 |

OTHER PUBLICATIONS

Boschelli et al., Synthesis and Tyrosine Kinase Inhibitory Activity of a Series of 2–Amino–8–H–pyrido[2,3–d]pyrimidines: Identification of Potent, Selective Platelet–Derived Growth Factor Receptor Tyrosine Kinase Inhibitors, J. Med. Chem., vol. 41, 1998, pp. 4365–4377.

(Continued)

*Primary Examiner*—Deepak Rao
(74) *Attorney, Agent, or Firm*—Morgan, Lewis & Bockius LLP

(57) ABSTRACT

Compounds of the formula (I): wherein $R^1$, $R^2$, $R^3$, $R^4$, $R^5$, $R^6$, p, q, and n are as defined within and a pharmaceutically acceptable salts and in vivo hydrolysable esters are described. Also described are processes for their preparation and their use as medicaments, particularly medicaments for producing a cell cycle inhibitory (anti-cell-proliferation) effect in a warm-blooded animal, such as man.

15 Claims, No Drawings

OTHER PUBLICATIONS

Deady et al., "Reactions of some Quinazoline Compounds with Ethoxymethylenemalonic Acid Derivatives", J. Heterocyclic Chem., vol. 26, 1989, pp. 161–168.

El–Kerdawy et al.; "2,4–Bis (Substituted)–5–Nitropyrimidines of Expected Diuretic Action"; Egypt J. Chem. vol. 29, No. 2, 1986, pp. 247–251.

Fiziol Akt Veshchestva, 1975, vol. 7, pp. 68–72.

Ghosh et al.; "2,4–Bis(arylamino)–5–methylpyrimidines as Antimicrobial Agents"; J. Med. Chem., 1967, vol. 10, No. 5, pp. 974–975.

Ghosh, "2,4–Bis(Arylamino)–6–Methyl Pyrimidines as Antimicrobial Agents", J. Indian Chem. Soc., vol. 58, No. 5, 1981, pp. 512–513.

Ghosh, "2,4–Bis(arylamino)–6–methylpyrimidines as an antimicrobial agents", Chemical Abstract No. 97712f, vol. 95, 1981, pp. 648.

Schmidt et al.; "A Convenient Synthesis of 2–substituted 4–Amino–5–pyrimidinecarbonitriles"; J. Heterocycle Chem., 1997, vol. 24, No. 5, pp. 1305–1307.

Zimmermann et al., Phenylamino–Pyrimidine (PAP) Derivatives: A New Class of Potent and Selective Inhibitors of Protein Kinase C (PKC), Arch. Pharm. Pharm. Med. Chem., vol. 329, 1996, pp. 371–376.

* cited by examiner

IMIDAZOLO-5-YL-2-ANILINO-PYRIMIDINES AS AGENTS FOR THE INHIBITION OF THE CELL PROLIFERATION

This application is a 371 of PCT/GB01/03864 filed Aug. 30, 2001.

The invention relates to pyrimidine derivatives, or pharmaceutically acceptable salts or in vivo hydrolysable esters thereof which possess cell-cycle inhibitory activity and are accordingly useful for their anti-cell-proliferation (such as anti-cancer) activity and are therefore useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppressor gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

The present invention is based on the discovery that certain pyrimidine compounds surprisingly inhibit the effects of cell cycle kinases showing selectivity for CDK2, CDK4 and CDK6, and thus possess anti-cell-proliferation properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Accordingly, the present invention provides a compound of formula (I):

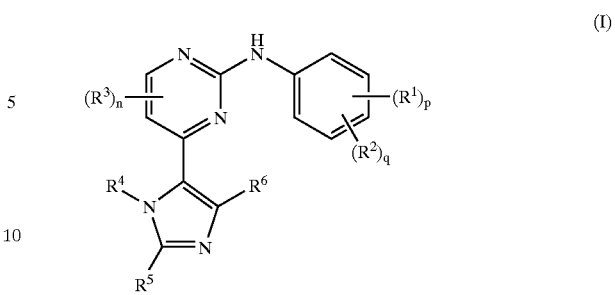

wherein:
$R^1$ is halo, nitro, cyano, hydroxy, amino, carboxy, carbamoyl, mercapto, $C_{1-6}$alkyl, $C_{1-6}$alkoxy, $C_{2-6}$alkenyl or $C_{2-6}$alkynyl;
p is 0–4; wherein the values of $R^1$ may be the same or different;
$R^2$ is sulphamoyl or a group $R^a$—$R^b$—;
q is 0–2; wherein the values of $R^2$ maybe the same or different; and wherein p+q=0–5;
$R^3$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N-($C_{1-3}$alkyl)amino, N,N-($C_{1-3}$alkyl)$_2$amino, $C_{1-3}$alkanoylamino, N-($C_{1-3}$alkyl)carbamoyl, N,N-($C_{1-3}$alkyl)$_2$carbamoyl, $C_{1-3}$alkylS(O)$_a$ wherein a is 0 to 2, N-($C_{1-3}$alkyl)sulphamoyl or N,N-($C_{1-3}$ alkyl)$_2$ sulphamoyl; wherein $R^3$ may be optionally substituted on carbon by one or more $R^c$;
n is 0 to 2, wherein the values of $R^3$ may be the same or different;
$R^4$ is hydrogen, $C_{1-6}$alkyl, $C_{2-6}$alkenyl, $C_{2-6}$alkynyl, $C_{3-8}$cycloalkyl, phenyl or a carbon-linked heterocyclic group; wherein $R^4$ may be optionally substituted on carbon by one or more $R^d$; and wherein if said heterocyclic group contains an —NH— moiety that nitrogen may be optionally substituted by a group selected from $R^n$;
$R^5$ and $R^6$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$ amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$ alkyl)$_2$sulphamoyl, $C_{1-6}$alkylsulphonylamino, $C_{3-8}$cycloalkyl or a 4–7 membered saturated heterocyclic group; wherein $R^5$ and $R^6$ independently of each other may be optionally substituted on carbon by one or more $R^e$; and wherein if said 4–7 membered saturated heterocyclic group contains an —NH— moiety that nitrogen may be optionally substituted by a group selected from $R^f$;
$R^a$ is selected from $C_{1-6}$alkyl, $C_{2-6}$alkenyl, $C_{2-6}$alkynyl, $C_{3-8}$cycloalkyl, $C_{3-8}$cycloalkylC$_{1-6}$alkyl, phenyl, a heterocyclic group, phenylC$_{1-6}$alkyl or (heterocyclic group)C$_{1-6}$ alkyl; wherein $R^a$ may be optionally substituted on carbon by one or more $R^g$; and wherein if said heterocyclic group contains an —NH— moiety that nitrogen may be optionally substituted by a group selected from $R^h$;
$R^b$ is —C(O)—, —N($R^m$)C(O)—, —C(O)N($R^m$)—, —S(O)$_r$—, —OC(O)N($R^m$)SO$_2$—, —SO$_2$N($R^m$)— or —N($R^m$)SO$_2$—; wherein $R^m$ is hydrogen or $C_{1-6}$alkyl optionally substituted by one or more $R^i$ and r is 1–2;
$R^d$, $R^g$ and $R^i$ are independently selected from halo, nitro, cyano, hydroxy, amino, carboxy, carbamoyl mercapto, sulphamoyl, $C_{1-6}$alkyl, $C_{2-6}$alkenyl, $C_{2-6}$alkynyl, $C_{1-6}$alkoxy, $C_{1-6}$alkoxy$C_{1-6}$alkoxy, $C_{1-6}$alkoxy$C_{1-6}$alkoxy$C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, $C_{1-6}$alkylsulphonylamino, $C_{3-8}$cycloalkyl, phenyl, heterocyclic group, phenyl$C_{1-6}$alkyl-R$^o$—, (heterocyclic group)$C_{1-6}$alkyl-R$^o$—, phenyl-R$^o$— or (heterocyclic group)-R$^o$—; wherein R$^d$, R$^g$ and R$^i$ independently of each other may be optionally substituted on carbon by one or more R$^j$; and wherein if said heterocyclic group contains an —NH— moiety that nitrogen may be optionally substituted by a group selected from R$^k$;

R$^o$ is —O—, —N(R$^p$)—, —C(O)—, —N(R$^p$)C(O)—, —C(O)N(R$^p$)—, —S(O)$_s$—, —SO$_2$N(R$^p$)— or —N(R$^p$)SO$_2$—; wherein R$^p$ is hydrogen or $C_{1-6}$alkyl and s is 0–2;

R$^f$, R$^h$, R$^k$ and R$^n$ are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)carbamoyl, benzyl, benzyloxycarbonyl, benzoyl and phenylsulphonyl; wherein R$^f$, R$^h$, R$^k$ and R$^n$ independently of each other may be optionally substituted on carbon by on or more R$^i$; and R$^c$, R$^e$, R$^i$ and R$^j$ are independently selected from halo, nitro, cyano, hydroxy, trifluoromethoxy, trifluoromethyl amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-ethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N,N-ethylsulphamoyl, N,N-dimethylsulphamoyl, N,N-diethylsulphamoyl or N-methyl-N-ethylsulphamoyl;

or a pharmaceutically acceptable salt or an in vivo hydrolysable ester thereof.

In another aspect the present invention provides a compound of formula (I):

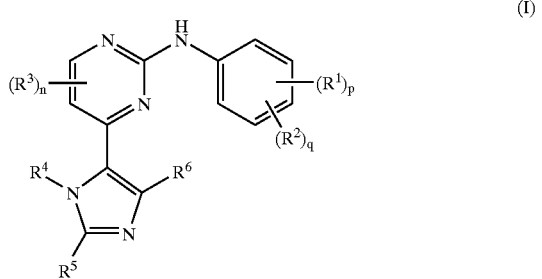

(I)

wherein:

R$^1$ is halo, nitro, cyano, hydroxy, ammo, carboxy, carbamoyl, mercapto, $C_{1-6}$alkyl, $C_{1-6}$alkoxy, $C_{2-6}$alkenyl or $C_{2-6}$alkynyl;

p is 0–4; wherein the values of R$^1$ may be the same or different;

R$^2$ is sulphamoyl or a group R$^a$—R$^b$—;

q is 0–2; wherein the values of R$^2$ maybe the same or different; and wherein p+q 0–5;

R$^3$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N-($C_{1-3}$alkyl)amino, N,N-($C_{1-3}$alkyl)$_2$amino, $C_{1-3}$alkanoylamino, N-($C_{1-3}$alkyl)carbamoyl, N,N-($C_{1-3}$alkyl)$_2$carbamoyl, $C_{1-3}$alkylS(O)$_a$ wherein a is 0 to 2, N-($C_{1-3}$alkyl)sulphamoyl or N,N-($C_{1-3}$alkyl)$_2$ sulphamoyl; wherein R$^3$ may be optionally substituted on carbon by one or more R$^c$;

n is 0 to 2, wherein the values of R$^3$ maybe the same or different;

R$^4$ is hydrogen, $C_{1-6}$alkyl, $C_{2-6}$alkenyl, $C_{2-6}$alkynyl, $C_{3-8}$cycloalkyl, phenyl or a carbon-linked heterocyclic group; wherein R$^4$ may be optionally substituted on carbon by one or more R$^d$; and wherein if said heterocyclic group contains an —NH— moiety that nitrogen may be optionally substituted by a group selected from R$^n$;

R$^5$ and R$^6$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$ amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl $C_{1-6}$alkylsulphonylamino, $C_{3-8}$cycloalkyl or a 4–7 membered saturated heterocyclic group; wherein R$^5$ and R$^6$ independently of each other may be optionally substituted on carbon by one or more R$^e$; and wherein if said 4–7 membered saturated heterocyclic group contains an —NH— moiety that nitrogen may be optionally substituted by a group selected from R$^f$;

R$^a$ is selected from $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, a heterocyclic group, phenyl$C_{1-6}$alkyl or (heterocyclic group)$C_{1-6}$alkyl; wherein R$^a$ may be optionally substituted on carbon by one or more R$^g$; and wherein if said heterocyclic group contains an —NH— moiety that nitrogen may be optionally substituted by a group selected from R$^h$;

R$^b$ is —C(O)—, —N(R$^m$)C(O)—, —C(O)N(R$^m$)—, —S(O)$_r$—, —SO$_2$N(R$^m$)— or —N(R$^m$)SO$_2$—; wherein R$^m$ is hydrogen or $C_{1-6}$alkyl optionally substituted by one or more R$^i$ and r is 1–2;

R$^d$, R$^g$ and R$^i$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl) carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl) sulphamoyl, N,N-($C_{1-6}$alkyl)$_2$sulphamoyl, $C_{1-6}$alkylsulphonylamino, $C_{3-8}$cycloalkyl, phenyl, heterocyclic group, phenyl-R$^o$— or (heterocyclic group)-R$^o$—; wherein R$^d$, R$^g$ and R$^i$ independently of each other may be optionally substituted on carbon by one or more R$^j$; and wherein if said heterocyclic group contains an —NH— moiety that nitrogen may be optionally substituted by a group selected from R$^k$;

R$^o$ is —O—, —N(R$^p$)—, —C(O)—, —N(R$^p$)C(O)—, —C(O)N(R$_p$)—, —S(O)$_s$—, —SO$_2$N(R$^p$)— or —N(R$^p$)SO$_2$—; wherein R$^p$ is hydrogen or $C_{1-6}$alkyl and s is 0–2;

R$^f$, R$^h$, R$^k$ and R$^n$ are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)carbamoyl, benzyl, benzyloxycarbonyl, benzoyl and phenylsulphonyl; wherein R$^f$, R$^h$ and R$^k$ independently of each other may be optionally substituted on carbon by on or more R$^i$; and R$^c$, R$^e$, R$^i$ and R$^j$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;
or a pharmaceutically acceptable salt or an in vivo hydrolysable ester thereof.

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, $C_{1-3}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" includes phenyl$C_{1-4}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclic group" is a saturated, partially saturated or unsaturated, mono or bicyclic ring containing 4–12 atoms of which at least one atom is chosen from nitrogen, sulphur or oxygen, which may, unless otherwise specified, be carbon or nitrogen linked, wherein a —$CH_2$— group can optionally be replaced by a —C(O)—, a ring nitrogen atom may optionally bear a $C_{1-6}$alkyl group and form a quaternary compound or a ring nitrogen and/or sulphur atom may be optionally oxidised to form the N-oxide and or the S-oxides. Examples and suitable values of the term "heterocyclic group" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. Preferably a "heterocyclic group" is a saturated, partially saturated or unsaturated, mono or bicyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidised to form the S-oxides. More preferably a "heterocyclic group" is tetrahydrofuryl, pyridyl, pyrrolidinonyl, morpholino, imidazolyl, piperidinyl or pyrrolidinyl. Particularly a "heterocyclic group" is tetrahydrofuryl or morpholino. In another aspect of the invention, particularly a "heterocyclic group" is tetrahydrofuran-2-yl, 2-oxopyrrolidin-1-yl, furan-2-yl, oxazolyl, morpholino, piperidinyl, thiazolyl, pyrazinyl, isoxazolyl, tetrahydropyran, pyridyl, isoxazolyl, isothiazolyl, 1,2,5-thiadiazolyl, phthalimido.

A "4–7 membered saturated heterocyclic group" is a saturated monocyclic ring containing 4–7 atoms of which at least one atom is chosen from nitrogen, sulphur or oxygen, which may, unless otherwise specified, be carbon or nitrogen linked, wherein a —$CH_2$— group can optionally be replaced by a —C(O)— and a sulphur atom may be optionally oxidised to form the S-oxides. Examples and suitable values of the term "heterocyclic group" are morpholino, piperidyl, 1,4-dioxanyl, 1,3-dioxolanyl, 1,2-oxathiolanyl, imidazolidinyl, pyrazolidinyl, piperazinyl, thiazolidinyl, pyrrolidinyl, thiomorpholino, homopiperazinyl and tetrahydropyranyl.

An example of "$C_{1-6}$alkanoyloxy" is acetoxy. Examples of "$C_{1-6}$alkoxycarbonyl" include $C_{1-4}$alkoxycarbonyl, methoxycarbonyl, ethoxycarbonyl, n- and t-butoxycarbonyl. Examples of "$C_{1-6}$alkoxy" include $C_{1-4}$alkoxy, $C_{1-3}$alkoxy, methoxy, ethoxy and propoxy. Examples of "$C_{1-6}$alkanoylamino" include formamido, acetamido and propionylamino. Examples of "$C_{1-6}$alkylS(O)$_a$ wherein a is 0 to 2" include $C_{1-4}$alkylsulphonyl, methylthio, ethylthio, methylsulphinyl, ethylsulphinyl, mesyl and ethylsulphonyl. Examples of "$C_{1-6}$alkylS(O)$_r$ wherein r is 1 to 2" include methylsulphinyl, ethylsulphinyl, mesyl and ethylsulphonyl. Examples of "$C_{1-6}$alkanoyl" include $C_{1-4}$alkanoyl, propionyl and acetyl. Examples of "N-$C_{1-6}$alkylamino" include methylamino and ethylamino. Examples of "N,N-($C_{1-6}$alkyl)$_2$amino" include di-N-methylamino, di-(N-ethyl)amino and N-ethyl-N-methylamino. Examples of "$C_{2-6}$alkenyl" are vinyl, allyl and 1-propenyl. Examples of "$C_{2-6}$alkynyl" are ethynyl, 1-propynyl and 2-propynyl. Examples of "N-($C_{1-6}$alkyl)sulphamoyl" are N-(methyl)sulphamoyl and N-(ethyl)sulphamoyl. Examples of "N-($C_{1-6}$alkyl)$_2$sulphamoyl" are N,N-(dimethyl)sulphamoyl and N-(methyl)-N-(ethyl)sulphamoyl. Examples of "N-($C_{1-6}$alkyl)carbamoyl" are N-($C_{1-4}$alkyl)carbamoyl, methylaminocarbonyl and ethylaminocarbonyl. Examples of "N,N-($C_{1-6}$alkyl)$_2$carbamoyl" are N,N-($C_{1-4}$alkyl)$_2$carbamoyl, dimethylaminocarbonyl and methylethylaminocarbonyl. Examples of "$C_{3-8}$cycloalkyl" are cyclopropyl, cyclobutyl, cyclopropyl and cyclohexyl. Examples of "(heterocyclic group)$C_{1-6}$alkyl" include pyridylmethyl, 3-morpholinopropyl and 2-pyrimid-2-ylethyl. Examples of "$C_{3-8}$cycloalkyl$C_{1-6}$alkyl" are cyclopropylethyl, cyclobutylmethyl, 2-cyclopropylpropyl and cyclohexylethyl.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and maybe formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

Some compounds of the formula (I) may have chiral centres and/or geometric isomeric centres (E- and Z-isomers), and it is to be understood that the invention encompasses all such optical, diastereoisomers and geometric isomers that possess CDK inhibitory activity.

The invention relates to any and all tautomeric forms of the compounds of the formula (I) that possess CDK inhibitory activity. In particular the skilled reader will appreciate that when $R^4$ is hydrogen, the imidazole ring as drawn in formula (I) may tautomerise.

It is also to be understood that certain compounds of the formula (I) can exist in solvated as well as unsolvated forms such as, for example, hydrated forms. It is to be understood that the invention encompasses all such solvated forms which possess CDK inhibitory activity.

Preferred values of $R^1$, $R^2$, $R^3$, $R^4$, $R^5$, $R^6$, n, p and q are as follows. Such values may be used where appropriate with any of the definitions, claims or embodiments defined hereinbefore or hereinafter.

Preferably $R^1$ is halo, amino, $C_{1-6}$alkyl or $C_{1-6}$alkoxy.
More preferably $R^1$ is halo, $C_{1-4}$alkyl or $C_{1-4}$alkoxy.
Particularly $R^1$ is chloro, $C_{1-3}$alkyl or $C_{1-3}$alkoxy.
More particularly $R^1$ is chloro.
In another aspect of the invention, preferably $R^1$ is halo, amino, $C_{1-6}$alkyl or $C_{1-6}$alkoxy.
In another aspect of the invention, more preferably $R^1$ is chloro, amino, methyl or methoxy.
Preferably p is 0–2; wherein the values of $R^1$ may be the same or different.
More preferably p is 0 or 1.
In one aspect of the invention, preferably p is 0.
In another aspect of the invention, preferably p is 1.
Preferably when p is 1, $R^1$ is meta or para to the —NH— of the aniline of formula (I).
More preferably when p is 1, $R^1$ is meta to the —NH— of the aniline of formula (I).
Preferably $R^2$ is sulphamoyl or a group $R^a$—$R^b$—; wherein
$R^a$ is selected from $C_{1-6}$alkyl, $C_{3-8}$cycloalkyl, $C_{3-8}$cycloalkylC$_{1-6}$alkyl, phenyl, a heterocyclic group, phenylC$_{1-6}$alkyl or (heterocyclic group)C$_{1-6}$alkyl; wherein $R^a$ may be optionally substituted on carbon by one or more $R^g$;
$R^b$ is —N(R$^m$)C(O)—, —C(O)N(R$^m$)—, —SO$_2$N(R$^m$)— or —N(R$^m$)SO$_2$—; wherein R$^m$ is hydrogen;
$R^g$ is selected from halo, hydroxy, amino, carbamoyl, $C_{1-6}$alkyl or $C_{1-6}$alkoxy, and
$R^j$ is selected from halo or hydroxy.

More preferably $R^2$ is sulphamoyl or a group $R^a$—$R^b$—, wherein
$R^a$ is selected from $C_{1-6}$alkyl, $C_{3-8}$cycloalylC$_{1-6}$alkyl, phenylC$_{1-6}$alkyl or (heterocyclic group)C$_{1-6}$alkyl; wherein $R^a$ may be optionally substituted on carbon by one or more $R^g$;
$R^b$ is —N(R$^m$)SO$_2$—; wherein R$^m$ is hydrogen;
$R^g$ is selected from halo, hydroxy, carbamoyl or $C_{1-6}$alkoxy; and
$R^j$ is selected from hydroxy.

Particularly $R^2$ is sulphamoyl, N-(tetrahydrofuran-2-ylmethyl)sulphamoyl, N-[3-(2-oxopyrrolidin-1-yl)propyl]sulphamoyl, N-(3-methoxypropyl)sulphamoyl, N-(4-fluorobenzyl)sulphamoyl, N-(cyclopropylmethyl)sulphamoyl, N-propylsulphamoyl, N-(2,3-dihydroxypropyl)sulphamoyl, N-[2-(2-hydroxyethoxy)ethyl]sulphamoyl, N-(furan-2-ylmethyl)sulphamoyl, N-(2-hydroxyethyl)sulphamoyl or N-(carbamoylmethyl)sulphamoyl.

In another aspect of the invention, preferably $R^2$ is sulphamoyl or a group $R^a$—$R^b$—; wherein
$R^a$ is selected from $C_{1-6}$alkyl, $C_{2-6}$alkenyl, $C_{2-6}$alkynyl, $C_{3-8}$cycloalkyl, phenyl or a heterocyclic group; wherein $R^a$ may be optionally substituted on carbon by one or more $R^g$;
$R^b$ is —N(R$^m$)C(O)—, —C(O)N(R$^m$)—, —S(O)$_r$—, —OC(O)N(R$^m$)SO$_2$—, —SO$_2$N(R$^m$)— or —N(R$^m$)SO$_2$—; wherein R$^m$ is hydrogen or $C_{1-6}$alkyl and r is 2;
$R^g$ is selected from halo, hydroxy, amino, cyano, carbamoyl, $C_{1-6}$alkyl, $C_{1-6}$alkoxy, $C_{1-6}$alkoxyC$_{1-6}$alkoxy, $C_{1-6}$alkoxyC$_{1-6}$alkoxyC$_{1-6}$alkoxy, N,N-(C$_{1-6}$alkyl)$_2$amino, $C_{1-6}$alkylS(O)$_a$ wherein a is 2, $C_{3-8}$cycloalkyl, phenyl, heterocyclic group, phenylC$_{1-6}$alkyl-R$^o$— or (heterocyclic group)-R$^o$—; wherein $R^g$ may be optionally substituted on carbon by one or more $R^j$;
$R^o$ is —O—; and
$R^j$ is selected from halo, hydroxy, methyl or methoxy.

In another aspect of the invention, more preferably $R^2$ is sulphamoyl or a group $R^a$—$R^b$—; wherein
$R^a$ is selected from methyl, ethyl, propyl, t-butyl, pentyl, 1,1-dimethylpropyl, 2,2-dimethylpropyl, allyl, 2-propynyl, cyclopropyl, cyclobutyl, phenyl or oxazolyl; wherein $R^a$ may be optionally substituted on carbon by one or more $R^g$;
$R^b$ is —N(R$^m$)C(O)—, —C(O)N(R$^m$)—, —S(O)$_2$—, —OC(O)N(R$^m$)SO$_2$—, —SO$_2$N(R$^m$)— or —N(R$^m$)SO$_2$—; wherein R$^m$ is hydrogen or methyl;
$R^g$ is selected from fluoro, hydroxy, amino, cyano, carbamoyl, methyl, methoxy, ethoxy, isopropoxy, ethoxyethoxy, ethoxyethoxyethoxy, N,N-dimethylamino, mesyl, cyclopropyl, phenyl, tetrahydrofuranyl, 2-oxopyrrordinyl, 1,3-dioxolanyl, morpholino, piperidinyl, furan, thiazolyl, pyrazinyl, isoxazolyl, tetrahydropyran, pyridyl, benzyloxy, isoxazolyloxy, isothiazolyloxy, 1,2,5-thiadiazolyloxy, wherein $R^g$ maybe optionally substituted on carbon by one or more $R^j$; and
$R^j$ is selected from fluoro, hydroxy, methyl or methoxy.

In another aspect of the invention, particularly $R^2$ is sulphamoyl, N-(t-butoxycarbonyl)sulphamoyl, N-(tetrahydrofur-2-ylmethyl)sulphamoyl, N-(cyclopropylmethyl)sulphamoyl, N-(fur-2-ylmethyl)sulphamoyl, N-(cyanomethyl)sulphamoyl, N-(2,2-dimethyl-1,3-dioxolan-4-ylmethyl)sulphamoyl, N-(carbamoylmethyl)sulphamoyl, N-methylsulphamoyl, N-(4-fluorobenzyl)sulphamoyl, N-(pyridin-2-ylmethyl)sulphamoyl, N-(pyridin-3-ylmethyl)sulphamoyl, N-(4-methylthiazol-2-yl)sulphamoyl, N-(3-methylisoxazol-5-ylmethyl)sulphamoyl, N-(tetrahydropyran-2-ylmethyl)sulphamoyl, N-(2-methylpyrazin-5-yl)sulphamoyl, N-[2-(2- hydroxyethoxy)ethyl]sulphamoyl, N-(2-hydroxyethyl) sulphamoyl, N-(2,2,2-trifluoroethyl)sulphamoyl, N-(2-methoxyethyl)sulphamoyl, N-(2-mesylethyl)sulphamoyl, N-(2-benzyloxyethyl)sulphamoyl, N-(2,2-dimethoxyethyl) sulphamoyl, N-[2-(N,N-dimethylamino)ethyl]sulphamoyl, N-(2-piperidin-1-ylethyl)sulphamoyl, N-[2-(methoxymethoxy)ethyl]sulphamoyl, N-ethylsulphamoyl, N-[2-(2-methoxyethoxy)ethyl]sulphamoyl, N-{2-[2-(2-methoxyethoxy)ethoxy]ethyl}sulphamoyl, N-(2-{2-[2-(2-methoxyethoxy)ethoxy]ethoxy}ethyl)sulphamoyl, N-(2-pyridin-2-ylethyl)sulphamoyl, N-(2-pyridin-4-ylethyl) sulphamoyl, N-(2-isoxazol-3-yloxyethyl)sulphamoyl, N-(2-isothiazol-3-yloxyethyl)sulphamoyl, N-(2-1,2-5-thiadiazol-3-yloxyethyl)sulphamoyl, N-methyl-N-(2-methoxyethyl) sulphamoyl, N-[3-(2-oxopyrrolidin1yl)propyl]sulphamoyl, N-(3-methoxypropyl)sulphamoyl, N-propylsulphamoyl, N-(2,3-dihydroxypropyl)sulphamoyl, N-(3-morpholinopropyl)sulphamoyl, N-[3-(N,N-dimethylamino) propyl]sulphamoyl, N-(3,3,3-trifluoropropyl)sulphamoyl, N-(2,2-dimethyl-3-hydroxypropyl)sulphamoyl, N-(3-hydroxypropyl)sulphamoyl, N-(3-ethoxypropyl) sulphamoyl, N-(2-hydroxypropyl)sulphamoyl, N-(3-isopropoxypropyl)sulphamoyl, N-(3-isopropoxy-2-hydroxypropyl)sulphamoyl, N-(3-isoxazol-3-yloxypropyl) sulphamoyl, N-(3-isothiazol-3-yloxypropyl)sulphamoyl, N-(3-1,2-5-thiadiazol-3-yloxypropyl)sulphamoyl, N-(1,1-dimethylpropyl)sulphamoyl, N-methyl-N-(3-morpholinopropyl)sulphamoyl, N-butylsulphamoyl, N-t-butylsulphamoyl, N-(2-hydroxybutyl)sulphamoyl, N-methyl-N-t-butylsulphamoyl, N-pentylsulphamoyl N-(5-hydroxypentyl)sulphamoyl, N-(4,5-dimethyloxazol-2-yl) sulphamoyl, N-(cyclopropyl)sulphamoyl, N-(cyclobutyl) sulphamoyl, N-(3-trifluoromethylphenyl)sulphamoyl, N-allylsulphamoyl, N-(2-propynyl)sulphamoyl, N-methylcarbamoyl, acetamido, mesylamino or mesyl.

In another aspect of the invention, more particularly $R^2$ is N-(cyclopropylmethyl)sulphamoyl, N-(2,2,2-trifluoroethyl) sulphamoyl, N-(2-methoxyethyl)sulphamoyl, N-(3-methoxypropyl)sulphamoyl, N-(cyclopropyl)sulphamoyl or N-(cyclobutyl)sulphamoyl.

Preferably q is 0 or 1.

In one aspect of the invention, preferably q is 0.

In another aspect of the invention, preferably q is 1.

Preferably when q is 1, $R^2$ is meta or para to the —NH— of the aniline of formula (I).

More preferably when q is 1, $R^2$ is para to the —NH— of the aniline of formula (I).

Preferably p+q=0–3.

More preferably p+q is 0–2.

Particularly p+q is 0 or 1.

In one aspect of the invention, preferably p+q is 0.

In another aspect of the invention, preferably p+q is 1.

Preferably $R^3$ is halo.

More preferably $R^3$ is bromo.

In another aspect of the invention preferably $R^3$ is bromo or chloro.

Preferably n is 0 or 1.

In one aspect of the invention, more preferably n is 0.

In another aspect of the invention, more preferably n is 1.

Preferably when n is 1, $R^3$ is in the 5-position of the pyrimidine ring.

Preferably $R^4$ is hydrogen, $C_{1-6}$alkyl, $C_{2-6}$alkenyl, $C_{2-6}$alkynyl; wherein $R^4$ may be optionally substituted on carbon by one or more $R^d$; wherein $R^d$ is as defined herein before.

More preferably $R^4$ is hydrogen or $C_{1-6}$alkyl; wherein $R^4$ may be optionally substituted on carbon by one or more $R^d$;

$R^d$ is selected from amino, $C_{1-6}$alkoxy, $C_{1-6}$alkanoylamino, $C_{1-6}$alkylsulphonylamino, phenyl, heterocyclic group, or (heterocyclic group)-$R_o$—; wherein $R^d$ may be optionally substituted on carbon by one or more $R^j$;

$R^o$ is —C(O)N($R^p$)—; wherein $R^p$ is hydrogen; and $R^j$ is halo.

Particularly $R^4$ is hydrogen or $C_{1-6}$alkyl; wherein $R^4$ may be optionally substituted on carbon by one or more $R^d$;

$R^d$ is selected from amino, $C_{1-6}$alkoxy, phenyl or heterocyclic group.

More particularly $R^4$ is hydrogen, methyl, ethyl, benzyl, 2-phthalimidoethyl, 2-aminoethyl or 2-methoxyethyl.

Particularly preferred $R^4$ is methyl or ethyl.

In another aspect of the invention, preferably $R^4$ is hydrogen, $C_{1-6}$alkyl or $C_{2-6}$alkenyl; wherein $R^4$ may be optionally substituted on carbon by one or more $R^d$; wherein $R^d$ is selected from halo, amino, $C_{1-6}$alkoxy, $C_{1-6}$alkanoylamino, $C_{1-6}$alkylsulphonylamino, phenyl or heterocyclic group.

In another aspect of the invention, more preferably $R^4$ is hydrogen, methyl, ethyl, isopropyl or 3-butenyl; wherein $R^4$ may be optionally substituted on carbon by one or more $R^d$; wherein $R^d$ is selected from fluoro, amino, methoxy, acetamido, mesylamino, phenyl or phthalimido.

In another aspect of the invention, particularly $R^4$ is hydrogen, methyl, ethyl, isopropyl, 3-butenyl, benzyl, 2-phthalimidoethyl, 2-aminoethyl, 2-methoxyethyl, 2-acetamidoethyl, 2-mesylaminoethyl or 2,2,2-trifluoroethyl.

In another aspect of the invention, more particularly $R^4$ is methyl, ethyl or isopropyl.

Preferably $R^5$ and $R^6$ are independently selected from hydrogen or $C_{1-6}$alkyl.

More preferably $R^5$ and $R^6$ are independently selected from hydrogen or methyl.

Particularly $R^5$ is selected from hydrogen or methyl and $R^6$ is hydrogen.

In another aspect of the invention, preferably $R^5$ and $R^6$ are independently selected from hydrogen or $C_{1-6}$alkyl; wherein $R^5$ and $R^6$ independently of each other may be optionally substituted on carbon by one or more $R^e$; wherein $R^e$ is selected from halo or methoxy.

In another aspect of the invention, more preferably $R^5$ and $R^6$ are independently selected from hydrogen, methyl, ethyl or isopropyl; wherein $R^5$ and $R^6$ independently of each other may be optionally substituted on carbon by one or more $R^e$; wherein $R^e$ is selected from fluoro or methoxy.

In another aspect of the invention, more preferably $R^5$ and $R^6$ are independently selected from hydrogen, methyl, ethyl, isopropyl, trifluoromethyl or methoxymethyl.

In another aspect of the invention, more preferably $R^5$ is methyl or isopropyl and $R^6$ is hydrogen.

Therefore in another aspect of the invention, there is provided a compound of formula (I) (as depicted above) wherein:

$R^1$ is chloro;

p is 0 or 1;

$R^2$ is sulphamoyl or a group $R^a$—$R^b$—;

$R^a$ is selected from $C_{1-6}$alkyl, $C_{3-8}$cycloalkyl$C_{1-6}$alkyl, phenyl$C_{1-6}$alkyl or (heterocyclic group)$C_{1-6}$alkyl; wherein $R^a$ maybe optionally substituted on carbon by one or more $R^g$;

$R^b$ is —N($R^m$)SO$_2$—; wherein $R^m$ is hydrogen;

$R^g$ is selected from halo, hydroxy, carbamoyl or $C_{1-6}$alkoxy;

$R^j$ is selected from hydroxy;
q is 0 or 1;
p+q is 0 or 1;
n is 0;
$R^4$ is hydrogen or $C_{1-6}$alkyl; wherein $R^4$ may be optionally substituted on carbon by one or more $R^d$;
$R^d$ is selected from amino, $C_{1-6}$alkoxy, phenyl or heterocyclic group; and
$R^5$ and $R^6$ are independently selected from hydrogen or $C_{1-6}$alkyl;
or a pharmaceutically acceptable salt or an in vivo hydrolysable ester thereof.

Therefore in a further aspect of the invention, there is provided a compound of formula (I) (as depicted above) wherein:
$R^1$ is chloro;
p is 0 or 1; and when p is 1, $R^1$ is meta to the —NH— of the aniline of formula (I);
$R^2$ is sulphamoyl, N-(tetrahydrofuran-2-ylmethyl)sulphamoyl, N-[3-(2-oxopyrrolidin-1-yl)propyl]sulphamoyl, N-(3-methoxypropyl)sulphamoyl, N-(4-fluorobenzyl)sulphamoyl, N-(cyclopropylmethyl)sulphamoyl, N-propylsulphamoyl, N-(2,3-dihydroxypropyl)sulphamoyl, N-[2-(2-hydroxyethoxy)ethyl]sulphamoyl, N-(furan-2-ylmethyl)sulphamoyl, N-(2-hydroxyethyl)sulphamoyl or N-(carbamoylmethyl)sulphamoyl;
q is 0 or 1; and when q is 1, $R^2$ is para to the —NH— of the aniline of formula (I);
p+q is 1;
n is 0;
$R^4$ is methyl or ethyl; and
$R^5$ is selected from hydrogen or methyl and $R^6$ is hydrogen;
or a pharmaceutically acceptable salt or an in vivo hydrolysable ester thereof.

Therefore in an a further additional aspect of the invention, there is provided a compound of formula (I) (as depicted above) wherein:
$R^1$ is halo, amino, $C_{1-6}$alkyl or $C_{1-6}$alkoxy;
p is 0–2; wherein the values of $R^1$ may be the same or different;
$R^2$ is sulphamoyl or a group $R^a$—$R^b$—; wherein
$R^a$ is selected from $C_{1-6}$alkyl, $C_{2-6}$alkenyl, $C_{2-6}$alkynyl, $C_{3-8}$cycloalkyl, phenyl or a heterocyclic group; wherein $R^a$ may be optionally substituted on carbon by one or more $R^g$;
$R^b$ is —N($R^m$)C(O)—, —C(O)$R^m$)—, —S(O)$_r$—, —OC(O)N($R^m$)SO$_2$—, —SO$_2$N($R^m$)— or —N($R^m$)SO$_2$—; wherein $R^m$ is hydrogen or $C_{1-6}$alkyl and r is 2;
$R^g$ is selected from halo, hydroxy, amino, cyano, carbamoyl, $C_{1-6}$alkyl, $C_{1-6}$alkoxy, $C_{1-6}$alkoxy$C_{1-6}$alkoxy, $C_{1-6}$alkoxy$C_{1-6}$alkoxy$C_{1-6}$alkoxy, N,N-($C_{1-6}$alkyl)$_2$amino, $C_{1-6}$alkylS(O)$_a$ wherein a is 2, $C_{3-8}$cycloalkyl, phenyl, heterocyclic group, phenyl$C_{1-6}$alkyl-$R^o$— or (heterocyclic group)-$R^o$—; wherein $R^g$ may be optionally substituted on carbon by one or more $R^j$;
$R^o$ is —O—;
$R^j$ is selected from halo, hydroxy, methyl or methoxy;
q is 0 or 1;
$R^3$ is halo;
n is 0 or 1;
$R^4$ is hydrogen, $C_{1-6}$alkyl or $C_{2-6}$alkenyl; wherein $R^4$ maybe optionally substituted on carbon by one or more $R^d$; wherein
$R^d$ is selected from halo, ammo, $C_{1-6}$alkoxy, $C_{1-6}$alkanoylamino, $C_{1-6}$alkylsulphonylamino, phenyl or heterocyclic group; and
$R^5$ and $R^6$ are independently selected from hydrogen or $C_{1-6}$alkyl; wherein $R^5$ and $R^6$ independently of each other may be optionally substituted on carbon by one or more $R^e$; wherein
$R^e$ is selected from halo or methoxy.
or a pharmaceutically acceptable salt or an in vivo hydrolysable ester thereof.

Therefore in another further additional aspect of the invention, there is provided a compound of formula (I) (as depicted above) wherein:
$R^1$ is chloro, amino, methyl or methoxy;
p is 0–2; wherein the values of $R^1$ may be the same or different;
$R^2$ is sulphamoyl, N-(tetrahydrofur-2-ylmethyl)sulphamoyl, N-(cyclopropylmethyl)sulphamoyl, N-(fur-2-ylmethyl)sulphamoyl, N-(2,2-dimethyl-1,3-dioxolan-4-ylmethyl)sulphamoyl, N-(cyanomethyl)sulphamoyl, N-(carbamoylmethyl)sulphamoyl, N-methylsulphamoyl, N-(4-fluorobenzyl)sulphamoyl, N-(pyridin-2-ylmethyl)sulphamoyl, N-(pyridin-3-ylmethyl)sulphamoyl, N-(4-methylthiazol-2-yl)sulphamoyl, N-(3-methylisoxazol-5-ylmethyl)sulphamoyl, N-(tetrahydropyran-2-ylmethyl)sulphamoyl, N-(2-methylpyrazin-5-yl)sulphamoyl, N-[2-(2-hydroxyethoxy)ethyl]sulphamoyl, N-(2-hydroxyethyl)sulphamoyl, N-(2,2,2-trifluoroethyl)sulphamoyl, N-(2-methoxyethyl)sulphamoyl, N-(2-mesylethyl)sulphamoyl, N-(2-benzyloxyethyl)sulphamoyl, N-(2,2-dimethoxyethyl)sulphamoyl, N-[2-(N,N-dimethylamino)ethyl]sulphamoyl, N-(2-piperidin-1-ylethyl)sulphamoyl, N-[2-(methoxymethoxy)ethyl]sulphamoyl, N-ethylsulphamoyl, N-[2-(2-methoxyethoxy)ethyl]sulphamoyl, N-{2-[2-(2-methoxyethoxy)ethoxy]ethyl}sulphamoyl, N-(2-{2-[2-(2-methoxyethoxy)ethoxy]ethoxy}ethyl)sulphamoyl, N-(2-pyridin-2-ylethyl)sulphamoyl, N-(2-pyridin-4-ylethyl)sulphamoyl, N-(2-isoxazol-3-yloxyethyl)sulphamoyl, N-(2-isothiazol-3-yloxyethyl)sulphamoyl, N-(2-1,2-5-thiadiazol-3-yloxyethyl)sulphamoyl, N-methyl-N-(2-methoxyethyl)sulphamoyl, N-[3-(2-oxopyrrolidin-1yl)propyl]sulphamoyl, N-(3-methoxypropyl)sulphamoyl, N-propylsulphamoyl, N-(2,3-dihydroxypropyl)sulphamoyl, N-(3-morpholinopropyl)sulphamoyl, N-[3-(N,N-dimethylamino)propyl]sulphamoyl, N-(3,3,3-trifluoropropyl)sulphamoyl, N-(2,2-dimethyl-3-hydroxypropyl)sulphamoyl, N-(3-hydroxypropyl)sulphamoyl, N-(3-ethoxypropyl)sulphamoyl, N-(2-hydroxypropyl)sulphamoyl, N-(3-isopropoxypropyl)sulphamoyl, N-(3-isopropoxy-2-hydroxypropyl)sulphamoyl, N-(3-isoxazol-3-yloxypropyl)sulphamoyl, N-(3-isothiazol-3-yloxypropyl)sulphamoyl, N-(3-1,2-5-thiadiazol-3-yloxypropyl)sulphamoyl, N-(1,1-dimethylpropyl)sulphamoyl, N-methyl-N-(3-morpholinopropyl)sulphamoyl, N-butylsulphamoyl, N-t-butylsulphamoyl, N-(2-hydroxybutyl)sulphamoyl, N-methyl-N-t-butylsulphamoyl, N-pentylsulphamoyl, N-(5-hydroxypentyl)sulphamoyl, N-(4,5-dimethyloxazol-2-yl)sulphamoyl, N-(cyclopropyl)sulphamoyl, N-(cyclobutyl)sulphamoyl, N-(3-trifluoromethylphenyl)sulphamoyl, N-allylsulphamoyl N-(2-propynyl)sulphamoyl, N-methylcarbamoyl, acetamido, mesylamino or mesyl;
q is 0 or 1;
$R^3$ is bromo or chloro;
n is 0 or 1;
$R^4$ is hydrogen, methyl, ethyl, isopropyl, 3-butenyl, benzyl, 2-phthalimidoethyl, 2-aminoethyl, 2-methoxyethyl, 2-acetamidoethyl, 2-mesylaminoethyl or 2,2,2-trifluoroethyl;
$R^5$ and $R^6$ are independently selected from hydrogen, methyl, ethyl, isopropyl, trifluoromethyl or methoxymethyl;
or a pharmaceutically acceptable salt or an in vivo hydrolysable ester thereof.

In another aspect of the invention, preferred compounds of the invention are any one of the Examples or a pharmaceutically acceptable salt or an in vivo hydrolysable ester thereof.

In a further aspect of the invention, preferred compounds of the invention are Examples 25, 37, 42, 43, 53, 67, 121, 122, 123 and 136.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt or an in vivo hydrolysable ester thereof which process (wherein $R^1$, $R^2$, $R^3$, $R^4$, $R^5$, $R^6$, n, p and q are, unless otherwise specified, as defined in formula (I)) comprises of:

Process a) Reaction of a Pyrimidine of Formula (II):

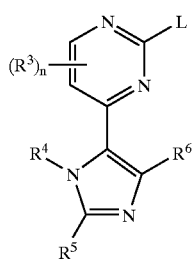
(II)

wherein L is a displaceable group; with an aniline of formula (III):

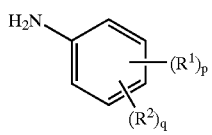
(III)

or
Process b) Reacting a Compound of Formula (IV):

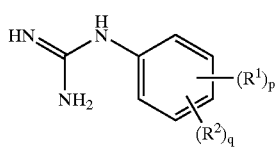
(IV)

with a compound of formula (V):

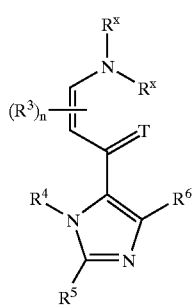
(V)

wherein T is O or S; $R^x$ maybe the same or different and is selected from $C_{1-6}$alkyl;

Process c) for Compounds of Formula (I) Where $R^2$ is Sulphamoyl or a Group $R^a$—$R^b$— and $R^b$ is —$NHSO_2$—; Reacting a Pyrimidine of Formula (VI):

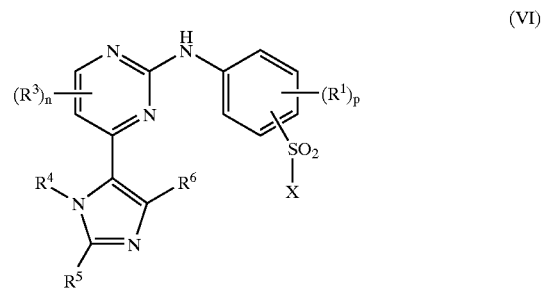
(VI)

wherein X is a displaceable group; with an amine of formula (VII):

$$R^a\text{—}NH_2 \qquad (VII)$$

Process d) for Compounds of Formula (I); Reacting a Pyrimidine of Formula (VIII):

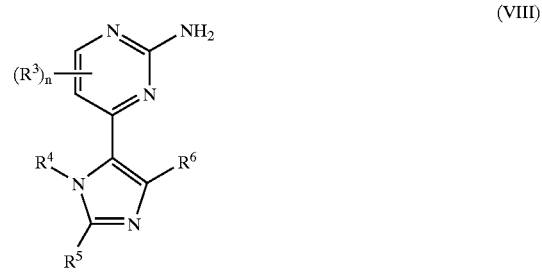
(VIII)

with a compound of formula (IX):

(IX)

where Y is a displaceable group;
and thereafter if necessary:
i) converting a compound of the formula (I) into another compound of the formula (I);
ii) removing any protecting groups;
iii) forming a pharmaceutically acceptable salt or in vivo hydrolysable ester.

L is a displaceable group, suitable values for L are for example, a halogeno or sulphonyloxy group, for example a chloro, bromo, methanesulphonyloxy or toluene-4-sulphonyloxy group.

X is a displaceable group, suitable values for X are for example, a fluoro or chloro group. Preferably X is fluoro.

Y is a displaceable group, suitable values for Y are for example, a halogeno or sulphonyloxy group, for example a bromo, iodo or trifluoromethanesulphonyloxy group. Preferably Y is iodo.

Specific reaction conditions for the above reactions are as follows.

Process a) Pyrimidines of Formula (II) and Anilines of Formula (III) may be Reacted Together:
i) in the presence of a suitable solvent for example a ketone such as acetone or an alcohol such as ethanol or butanol or an aromatic hydrocarbon such as toluene or N-methyl pyrrolidine, optionally in the presence of a suitable acid for example an inorganic acid such as hydrochloric acid or sulphuric acid, or an organic acid such as acetic acid or formic acid (or a suitable Lewis acid) and at a temperature in the range of 0° C. to reflux, preferably reflux; or ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) where L is chloro maybe prepared according to Scheme 1:

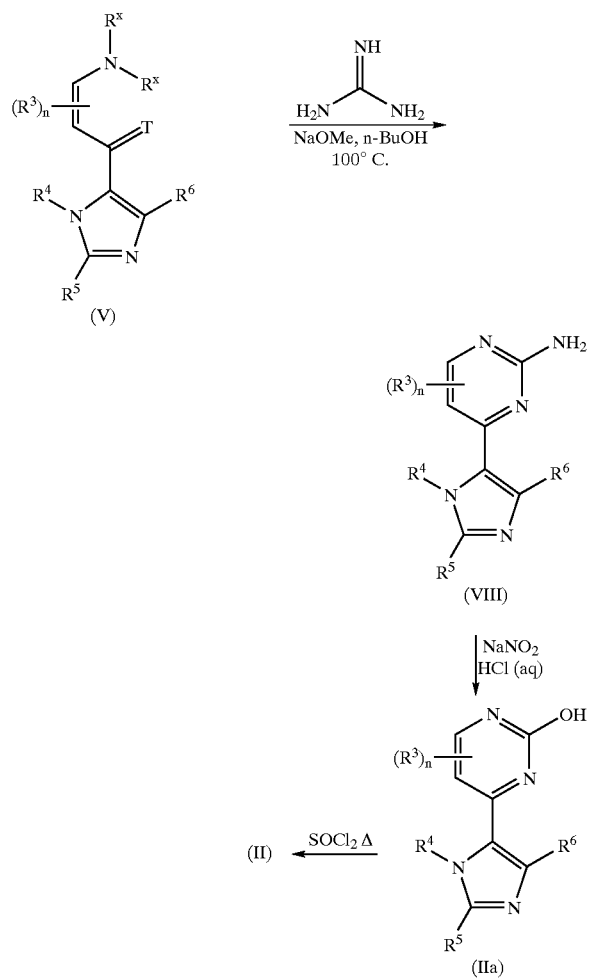

Anilines of formula (III) are commercially available compounds, or they are known in the literature, or they are prepared by standard processes known in the art.

Process b) Compounds of formula (IV) and compounds of formula (V) are reacted together in a suitable solvent such as N-methylpyrrolidinone or butanol at a temperature in the range of 100–200° C., preferably in the range of 150–170° C. The reaction is preferably conducted in the presence of a suitable base such as, for example, sodium hydride, sodium methoxide or potassium carbonate.

Compounds of formula (V) may be prepared according to Scheme 2:

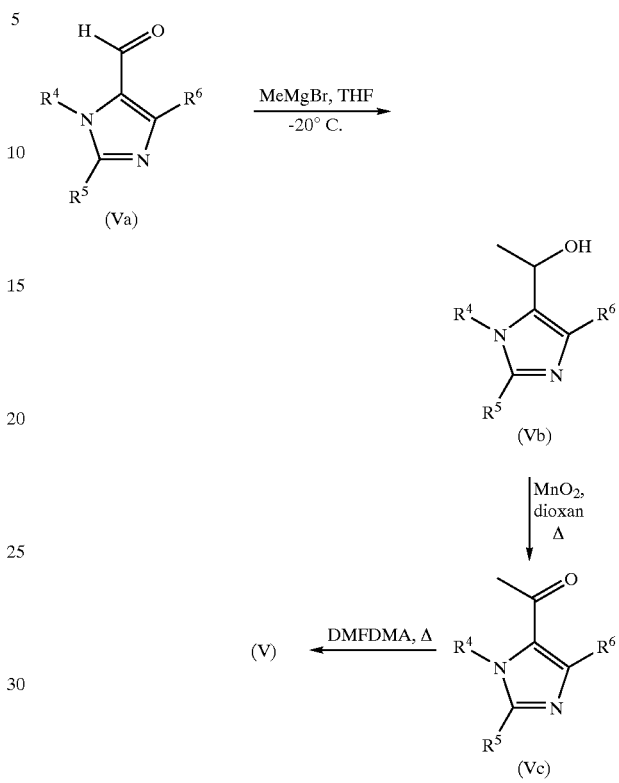

Compounds of formula (IV) and (Va) are commercially available compounds, or they are known in the literature, or they are prepared by standard processes known in the art.

Process c) Compounds of formula (VI) and amines of formula (VII) may be reacted together in the presence of an inert solvent such as N-methylpyrrolidinone or pyridine, in the presence of a base for example an inorganic base such as caesium carbonate or in the presence of an organic base such as excess (VII) and at a temperature in the range of 25 to 80° C.

Compounds of formula (VI) (wherein X is chloro) may be prepared according to Scheme 3:

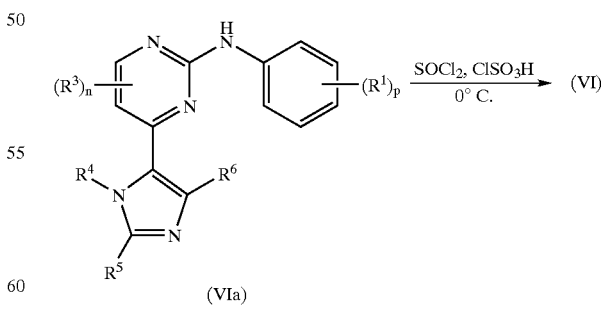

Compounds of formula (VIa) may be prepared according to Process a, Process b or Process d wherein q is 0.

Process d) Compounds of formula (VIII) and amines of formula (IX) may be reacted together under standard Buchwald conditions as described in Process a.

The synthesis of compounds of formula (VIII) is described in Scheme 1.

Compounds of formula (IX) are commercially available compounds, or they are known in the literature, or they are prepared by standard processes known in the art.

Amines of formula (VI) are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possesses anti-cell-proliferation activity such as anti-cancer activity which is believed to arise from the CDK inhibitory activity of the compound. These properties may be assessed, for example, using the procedure set out below:

Assay

The following abbreviations have been used:—

HEPES is N-[2-Hydroxyethyl]piperazine-N'-[2-ethanesulfonic acid]

DTT is Dithiothreitol

PMSF is Phenylmethylsulphonyl Fluoride

The compounds were tested in an in vitro kinase assay in 96 well format using Scintillation Proximity Assay (SPA—obtained from Amersham) for measuring incorporation of [γ-33-P]-Adenosine Triphosphate into a test substrate (GST-Retinoblastoma protein; GST-Rb). In each well was placed the compound to be tested (diluted in DMSO and water to correct concentrations) and in control wells either roscovitine as an inhibitor control or DMSO as a positive control.

Approximately 0.21 μl of CDK2/Cyclin E partially-purified enzyme (amount dependent on enzyme activity) diluted in 25 μl incubation buffer was added to each well then 20 μl of GST-Rb/ATP/ATP33 mixture (containing 0.5 μg GST-Rb and 0.2 μM ATP and 0.14 μCi [γ-33-P]-Adenosine Triphosphate in incubation buffer), and the resulting mixture shaken gently, then incubated at room temperature for 60 minutes.

To each well was then added 150 μL stop solution containing (0.8 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124×g., for 5 minutes. The plates were read on a Topcount for 30 seconds per well.

The incubation buffer used to dilute the enzyme and substrate mixes contained 50 mM HEPES pH 7.5, 10 mM $MnCl_2$, 1 mM DTT, 100 μM Sodium vanadate, 100 μM NaF, 10 mM Sodium Glycerophosphate, BSA (1 mg/ml final).

Test Substrate

In this assay only part of the retinoblastoma protein (Science 1987 Mar. 13;235(4794):1394–1399; Lee W. H., Bookstein R., Hong F., Young L. J., Shew J. Y., Lee E. Y.) was used, fused to a GST tag. PCR of retinoblastoma gene encoding amino acids 379–928 (obtained from retinoblastoma plasmid ATCC pLRbRNL) was performed, and the sequence cloned into pGEx 2T fusion vector (Smith D. B. and Johnson, K. S. Gene 67, 31 (1988); which contained a tac promoter for inducible expression, internal lac I$^q$ gene for use in any E. Coli host, and a coding region for thrombin cleavage—obtained from Pharmacia Biotech) which was used to amplify amino acids 792–928. This sequence was again cloned into pGEx 2T.

The refinoblastoma 792–928 sequence so obtained was expressed in E. Coli (BL21 (DE3) pLysS cells) using standard inducible expression techniques, and purified as follows.

E. coli paste was resuspended in 10 ml/g of NETN buffer (50 mM Tris pH 7.5, 120 mM NaCl, 1 mM EDTA, 0.5% v/v NP-40, 1 mM PMSF, 1 ug/ml leupeptin, 1 ug/ml aprotinin and 1 ug/ml pepstatin) and sonicated for 2×45 seconds per 100 ml homogenate. After centrifugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM DTT, 1 mM MgCl2, 1 mM PMSF, 1 ug/ml leupeptin, 1 ug/ml aprotinin and 1 ug/ml pepstatin) the protein was eluted with 50 mM reduced glutathione in kinase buffer. Fractions containing GST-Rb (792–927) were pooled and dialysed overnight against kinase buffer. The final product was analysed by Sodium Dodeca Sulfate (SDS) PAGE (Polyacrylamide gel) using 8–16% Tris-Glycine gels (Novex, San Diego, USA).

CDK2 and Cyclin E

The open reading frames of CDK2 and Cyclin E were isolated by reverse transcriptase-PCR using HeLa cell and activated T cell mRNA as a template and cloned into the insect expression vector pVL1393 (obtained from Invitrogen 1995 catalogue number: V1392-20). CDK2 and cyclin E were then dually expressed [using a standard virus Baculogold co-infection technique] in the insect SF21 cell system (Spodoptera Frugiperda cells derived from ovarian tissue of the Fall Army Worm—commercially available).

Example Production of Cyclin E/CDK2

The following Example provides details of the production of Cyclin E/CDK2 in SF21 cells (in TC100+10% FBS (TCS)+0.2% Pluronic) having dual infection MOI 3 for each virus of Cyclin E & CDK2.

SF21 cells grown in a roller bottle culture to 2.33×10$^6$ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

The viruses were mixed together before addition to the cultures, and the cultures returned to the roller rig 28° C.

After 2 days (48 hrs.) post infection the 5 Liters of culture was harvested. The total cell count at harvest was 1.58×10E6 cells/ml.(99% viable). The cells were spun out at 2500 rpm, 30 mins., 4° C. in Heraeus Omnifuge 2.0 RS in 250 ml. lots. The supernatant was discarded.

Partial Co-purification of Cdk2 and Cyclin E

Sf21 cells were resuspended in lysis buffer (50 mM Tris pH 8.2, 10 mM MgCl$_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homgeniser. After centrifugation, the supernatant was loaded onto a Poros HQ/M 1.4/100 anion exchange column (PE Biosystems, Hertford, UK). Cdk2 and Cyclin E were coeluted at the beginning of a 0–1M NaCl gradient (run in lysis buffer minus protease inhibitors) over 20 column volumes. Co-elution was checked by western blot using both anti-Cdk2 and anti-Cyclin E antibodies (Santa Cruz Biotechnology, California, US).

By analogy, assays designed to assess inhibition of CDK4 and CDK6 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

Although the pharmacological properties of the compounds of the formula (I) vary with structural change, in general activity possessed by compounds of the formula (I) may be demonstrated at IC$_{50}$ concentrations or doses in the range 250 µM to 1 nM.

When tested in the above in-vitro assay the CDK2 inhibitory activity of Example 14 was measured as IC$_{50}$=0.146 µM.

The in vivo activity of the compounds of the present invention may be assessed by standard techniques, for example by measuring inhibition of cell growth and assessing cytotoxicity.

Inhibition of cell growth may be measured by staining cells with Sulforhodamine B (SRB), a fluorescent dye that stains proteins and therefore gives an estimation of amount of protein (i.e. cells) in a well (see Boyd, M. R. (1989) Status of the NCI preclinical antitumour drug discovery screen. Prin. Prac Oncol 10:1–12). Thus, the following details are provided of measuring inhibition of cell growth:—

Cells were plated in appropriate medium in a volume of 100 µl in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DMSO (v/v). A control plate was assayed to give a value for cells before dosing. Cells were incubated at 37° C., (5% CO$_2$) for three days.

At the end of three days TCA was added to the plates to a final concentration of 16% (v/v). Plates were then incubated at 4° C. for 1 hour, the supernatant removed and the plates washed in tap water. After drying, 100 µl SRB dye (0.4% SRB in 1% acetic acid) was added for 30 minutes at 37° C. Excess SRB was removed and the plates washed in 1% acetic acid. The SRB bound to protein was solubilised in 10 mM Tris pH 7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical IC$_{50}$ values for compounds of the invention when tested in the SRB assay are in the range 1 mM to 1 nM.

According to a further aspect of the invention there is provided a pharmaceutical composition which comprises a pyrimidine derivative of the formula (I), or a pharmaceutically acceptable salt or in vivo hydrolysable ester thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt or in vivo hydrolysable ester thereof, as defined hereinbefore for use in a method of treatment of the human or animal body by therapy.

We have found that the compounds defined in the present invention, or a pharmaceutically acceptable salt or in vivo hydrolysable ester thereof, are effective cell cycle inhibitors (anti-cell proliferation agents), which property is believed to arise from their CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds maybe used to produce an anti-proliferative effect mediated alone or in part by the inhibition of CDKs. Such a compound of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a compound of the invention will possess anti-cancer activity against these cancers. It is in addition expected that a compound of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDKs, especially those tumours which are significantly dependent on CDKs for their growth and spread, including for example, certain tumours of the colon, breast, prostate, lung, vulva and skin.

It is further expected that a compound of the present invention will possess activity against other cell-proliferation diseases in a wide range of other disease states including leukaemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a compound of the formula (I), or a pharmaceutically acceptable salt or in vivo hydrolysable ester thereof, as defined hereinbefore for use as a medicament; and the use of a compound of the formula (I), or a pharmaceutically acceptable salt or in vivo hydrolysable ester thereof, as defined hereinbefore in the manufacture of a medicament for use in the production of a cell cycle inhibitory (anti-cell-proliferation) effect in a warm-blooded animal such as man. Particularly, an inhibitory effect is produced by preventing entry into or progression through the S phase by inhibition of CDK2, CDK4 and/or CDK6, especially CDK2.

According to a further feature of the invention, there is provided a compound of the formula (I), or a pharmaceutically acceptable salt or in vivo hydrolysable ester thereof, as defined herein before in the manufacture of a medicament for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, particularly in the treatment of cancers.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound as defined immediately above. Particularly, an inhibitory effect is produced by preventing entry into or progression through the S phase by inhibition of CDK2, CDK4 and/or CDK6, especially CDK2.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound of formula (I) or a pharmaceutically acceptable salt or in vivo hydrolysable ester thereof as defined herein before. Particularly, an inhibitory effect is produced by preventing entry into or progression through the S phase by inhibition of CDK2, CDK4 and/or CDK6, especially CDK2.

According to an additional feature of this aspect of the invention there is provided a method of treating cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal, such as man, in need of such treatment which comprises administering to said animal an effective amount of a compound of formula (I) or a pharmaceutically acceptable salt or in vivo hydrolysable ester thereof as defined herein before.

Particularly there is provided a method of treating cancer in a warm-blooded animal, such as man, in need of such treatment which comprises administering to said animal an effective amount of a compound of formula (I) or a pharmaceutically acceptable salt or in vivo hydrolysable ester thereof as defined herein before.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the production of a cell cycle inhibitory (anti-cell-proliferation) effect in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancer in a warm-blooded animal such as man.

Preventing cells from entering DNA synthesis by inhibition of essential S-phase initiating activities such as CDK2 initiation may also be useful in protecting normal cells of the body from toxicity of cycle-specific pharmaceutical agents. Inhibition of CDK2 or 4 will prevent progression into the cell cycle in normal cells which could limit the toxicity of cycle-specific pharmaceutical agents which act in S-phase, G2 or mitosis. Such protection may result in the prevention of hair loss normally associated with these agents.

Therefore in a further aspect of the invention there is provided a compound of formula (I) as defined above or a pharmaceutically acceptable salt or in vivo hydrolysable ester thereof for use as a cell protective agent.

Therefore in a further aspect of the invention there is provided a compound of formula (I) as defined above or a pharmaceutically acceptable salt or in vivo hydrolysable ester thereof for use in preventing hair loss arising from the treatment of malignant conditions with pharmaceutical agents.

Examples of pharmaceutical agents for treating malignant conditions that are known to cause hair loss include alkylating agents such as ifosfamide and cyclophosphamide; antimetabolites such as methotrexate, 5-fluorouracil, gemcitabine and cytarabine; vinca alkaloids and analogues such as vincristine, vincristine, vindesine, vinorelbine; taxanes such as paclitaxel and docetaxel; topoisomerase I inhibitors such as irintotecan and topotecan; cytotoxic antibiotics such as doxorubicin, daunorubicin, mitoxantrone, actinomycin-D and mitomycin; and others such as etoposide and tretinoin.

In another aspect of the invention, the compound of formula (I), or a pharmaceutically acceptable salt or in vivo hydrolysable ester thereof, may be administered in association with a one or more of the above pharmaceutical agents. In this instance the compound of formula (I) may be administered by systemic or non systemic means. Particularly the compound of formula (I) my may administered by non-systemic means, for example topical administration.

Therefore in an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof.

In an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof in simultaneous, sequential or separate administration with an effective amount of said pharmaceutical agent.

According to a further aspect of the invention there is provided a pharmaceutical composition for use In preventing hair loss arising from the treatment of malignant conditions with pharmaceutical agents which comprises a compound of formula (I), or a pharmaceutically acceptable salt or in vivo hydrolysable ester thereof, and said pharmaceutical agent, in association with a pharmaceutically acceptable diluent or carrier.

According to a further aspect of the present invention there is provided a kit comprising a compound of formula (I), or a pharmaceutically acceptable salt or in vivo hydrolysable ester thereof, and a pharmaceutical agent for treating malignant conditions that is known to cause hair loss.

According to a fixer aspect of the present invention there is provided a kit comprising:

a) a compound of formula (I), or a pharmaceutically acceptable salt or in vivo hydrolysable ester thereof, in a first unit dosage form;

b) a pharmaceutical agent for treating malignant conditions that is known to cause hair loss; in a second unit dosage form; and c) container means for containing said first and second dosage forms.

According to another feature of the invention there is provided the use of a compound of the formula (I), or a pharmaceutically acceptable salt or in vivo hydrolysable ester thereof, in the manufacture of a medicament for the prevention of hair loss during treatment of malignant conditions with pharmaceutical agents.

According to a further aspect of the present invention there is provided a combination treatment for the prevention of hair loss comprising the administration of an effective amount of a compound of the formula (I), or a pharmaceutically acceptable salt or in vivo hydrolysable ester thereof, optionally together with a pharmaceutically acceptable diluent or carrier, with the simultaneous, sequential or separate administration of an effective amount of a pharmaceutical agent for treatment of malignant conditions to a warm-blooded animal, such as man.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The CDK inhibitory activity defined hereinbefore may be applied as a sole therapy or may involve, in addition to a compound of the invention, one or more other substances and/or treatments. Such conjoint treatment maybe achieved by way of the simultaneous, sequential or separate administration of the individual components of the treatment. In the field of medical oncology it is normal practice to use a combination of different form of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan). According to this aspect of the invention there is provided a pharmaceutical product comprising a compound of the formula (I) as defined hereinbefore and an additional anti-tumour substance as defined hereinbefore for the conjoint treatment of cancer.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non limiting examples in which, unless stated otherwise:

(i) temperatures are given in degrees Celsius (° C.); operations were carried out at room or ambient temperature, that is, at a temperature in the range of 18–25° C.;

(ii) organic solutions were dried over anhydrous magnesium sulphate; evaporation of solvent was carried out using a rotary evaporator under reduced pressure (600–4000 Pascals; 4.5–30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated;

(viii) chemical symbols have their usual meanings; SI units and symbols are used;

(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is $(MH)^+$;

(xi) unless stated otherwise compounds containing an asymmetrically substituted carbon and/or sulphur atom have not been resolved;

(xii) where a synthesis is described as being analogous to that described in a previous example the amounts used are the millimolar ratio equivalents to those used in the previous example;

(xvi) the following abbreviations have been used:

| | |
|---|---|
| THF | tetrahydrofuran; |
| DMF | N,N-dimethylformamide; |
| DMFDMA | dimethylformamide dimethylacetal; |
| EtOAc | ethyl acetate; |
| MeOH | methanol; |
| EtOH | ethanol; |
| DCM | dichloromethane; and |
| DMSO | dimethylsulphoxide. | xvii) where an Isolute SCX-2 column is referred to, this means an "ion exchange" extraction cartridge for adsorption of basic compounds, i.e. a polypropylene tube containing a benzenesulphonic acid based strong cation exchange sorbent, used according to the manufacturers instructions obtained from International Sorbent Technologies Limited, Dyffryn Business Park, Hengeod, Mid Glamorgan, UK, CF82 7RJ;

xviii) where an Isolute amine column is referred to, this means an "ion exchange" extraction cartridge for adsorption of acidic compounds, i.e. a polypropylene tube containing a amino silane covalently bonded to a silica particle used according to the manufacturers instructions obtained from International Sorbent Technologies Limited, Dyffryn Business Park, Hengeod, Mid Glamorgan, UK, CF82 7RJ;

xix) where a Chemelut column is referred to, this means an extraction cartridge for removal of water, i.e. a polypropylene tube containing diatomaceous earth used according to the manufacturers instructions obtained from Varian, Harbor City, Calif., USA.

Example 1

2-(3-Chloroanilino)-4-(2-methylimidazol-5-yl)pyrimidin

Sodium hydride (45 mg of a 60% suspension in mineral oil, 1.12 mmol) was added to a stirred suspension of 5-(3-dimethylaminoprop-2-en-1-oyl)-2-methylimidazole (100 mg, 0.56 mmol) and 3-chlorophenylguanidine (95 mg, 0.56 mmol) in dry 1-butanol (4.0 ml) under nitrogen. The mixture was stirred at ambient temperature for 15 minutes then heated at 126° C. for 26 hours. The reaction mixture was allowed to cool and the volatiles were removed by evaporation. The residue was suspended in water (20 ml) and acetic acid (67 µl) was added and the solution extracted with DCM (3×20 ml). The extracts were combined, dried (NaSO$_4$) and the solvent removed by evaporation. The residue was purified by column chromatography eluting with DCM/MeOH (100:0 increasing in polarity to 92:8) to give the title compound 33 mg, (21%) as a solid. NMR: 2.35 (s, 3H), 6.95 (d, 1H), 7.23 (d, 1M, 7.30 (t, 1H), 7.67 (s, 1H), 7.72 (s, 1H), 8.05 (s, 1H), 8.43 (d, 1H), 9.62 (s, 1H), 12.15 (s, 1H); m/z: 286.

Example 2

2-(3-Chloroanilino)-4-(1,2-dimethylimidazol-5-yl)pyrimidine 5-(3-Dimethylaminoprop-2-en-1-oyl)-1,2-dimethylimidazole (Method 1; 111 mg, 0.58 mmol) and 3-chlorophenylguanidine (97 mg, 0.58 mmol) were treated as described in Example 1 to give the title compound 51 mg, (29%) as a solid. NMR: 2.40 (s, 3H), 3.97 (s, 3H), 6.98 (d, 1H), 7.15 (d, 1H), 7.30 (t, 1H), 7.58 (d, 1H), 7.67 (s, 1H), 7.97 (s, 1H), 8.40 (d, 1H), 9.68 (s, 1H); m/z: 300.

Example 3

2-Anilino-4-(2-methylimidazol-5-yl)pyrimidine

Sodium hydride (167 mg of a 60% suspension in mineral oil, 4.18 mmol) was added to a stirred suspension of 5-(3-dimethylaminoprop-2-en-1-oyl)-2-methylmidazole (250 mg, 1.39 mmol) and phenylguanidine hydrogen carbonate (275 mg, 1.39 mmol) was suspended in dry 1-butanol (10 ml) under nitrogen and the mixture stirred and heated under nitrogen at 126° C. for 18 hours. The reaction mixture was allowed to cool and further phenylguanidine hydrogen carbonate (275 mg, 1.39 mmol) and sodium hydride (111 mg of a 60% suspension in mineral oil, 2.78 mmol) added and the mixture stirred and heated at 126° C. for a further 20 hours. The reaction mixture was then worked-up as described in Example 1 to give the title compound 159 mg, (46%) as a solid. NMR: 2.33 (s, 3H), 6.92 (t, 1H), 7.18 (d, 1H), 7.27 (t, 2H), 7.67 (s, 1H), 7.80 (d, 2H), 8.36 (d, 1H), 9.37 (s, 1H), 12.12 (s, 1H); m/z: 252.

Example 4

4-(2-Methylimidazol-5-yl)-2-(4-sulphamoylanilino)pyrimidine

Thionyl chloride (2.0 ml) was added to 2-anilino-4-(2-methylimidazol-5-yl)pyrimidine (Example 3; 98 mg, 0.39 mmol) cooled at 0° C. under nitrogen. Chlorosulphonic acid (104 µl, 1.56 mmol) was added and the mixture was stirred at 0° C. for 30 minutes. Excess thionyl chloride was removed by evaporation and the residue treated with a mixture of THF (4.0 ml) and concentrated aqueous ammonia solution (1.0 ml). The mixture was stirred for 15 minutes and the volatiles were removed by evaporation. The residue was triturated with water, and the precipitated solid collected by filtration, washed with distilled water and dried under vacuum to give the title compound 62 mg, (48%). NMR: 2.33 (s, 3H), 7.10 (s, 2H), 7.24 (d, 1H), 7.72 (m, 3H), 7.95 (d, 2H), 8.43 (d, 1H), 9.83 (s, 1H); m/z: 331.

Example 5

2-Anilino-4-(1,2-dimethylimidazol-5-yl)pyrimidine 5-(3-Dimethylaminoprop-2-enoyl)-1,2-dimethylimidazole (Method 1; 314 mg, 1.62 mmol) and phenylguanidine hydrogen carbonate (321 mg, 1.62 mmol) were treated as described in Example 1 to give the title compound 113 mg, (26%) as a solid. NMR: 2.37 (s, 3H), 3.93 (s, 3H), 6.95 (t, 1H), 7.08 (d, 1H), 7.28 (t, 2H), 7.59 (s, 1H), 7.69 (d, 2H), 8.35 (d, 1H), 9.43 (s, 1H); m/z: 266.

Example 6

4-(1,2-Dimethylimidazol-5-yl)-2-(4-sulphamoylanilino)pyrimidine

Thionyl chloride (2.0 ml) was added to 2-anilino-4-(1,2-dimethylimidazol-5-yl)pyrimidine (Example 5; 94 mg, 0.36 mmol) cooled at 0° C. under nitrogen. Chlorosulphonic acid (94 µl, 1.56 mmol) was added and the mixture was stirred at 0° C. for 30 minutes, then allowed to warm and stirred for two hours at ambient temperature and then heated at 90° C. for one hour. Excess thionyl chloride was removed by evaporation and the residue azeotroped with toluene. The resulting crude sulphonyl chloride was treated with a mixture of THF (4.0 ml), water (2.0 ml), and concentrated aqueous ammonia solution (1.0 ml). The mixture was stirred for 15 minutes and the volatiles were removed by evaporation. The residue was triturated with water (5 ml), and the precipitated solid collected by filtration, washed with distilled water and dried under vacuum. The crude product was then suspended and stirred in DCM (10 ml) containing a few drops of MeOH. The solid product was collected by filtration, washed with DCM and dried under vacuum to give the tile compound 67 mg, (54%). NMR: 2.38 (s, 3H), 3.96 (s, 3H), 7.13 (s, 2H), 7.20 (d, 1H), 7.63 (s, 1H), 7.73 (d, 2H), 7.88 (d, 2H), 8.43 (d, 1H), 9.88 (s, 1H); m/z: 345.

Example 7

4-(1-Benzyl-2-methylimidazol-5-yl)-2-(3-chloroanilino)pyrimidine

Sodium methoxide (36.8 mg, 0.68 mmol) was added to a stirred suspension of 1-benzyl-5-(3-dimethylaminoprop-2-en-1-oyl)-2-methylimidazole (Method 5; 153 mg, 0.57 mmol) and 3-chlorophenylguanidine (106 mg, 0.62 mmol) in dry 1-butanol (1.0 ml) under nitrogen. The reaction mixture heated at reflux for 4 hours then allowed to cool. The volatiles were removed by evaporation and the residue partitioned between EtOAc and saturated aqueous sodium hydrogen carbonate solution. The organic phase was separated, dried and the solvent removed by evaporation. The residue was purified by column chromatography, eluting with DCM and 7M methanolic ammonia solution (97:3) to give the title compound 73 mg, (34%). NMR: 2.35 (s, 3H), 5.78 (s, 2H), 6.84–7.00 (m, 5H), 7.07 (t, 1H), 7.15–7.30 (m, 4H), 7.56–7.65 (m, 2H), 8.29 (d, 1H); m/z 374.

Example 8

2-(3-Chloroanilino)-4-[1-(2-methoxyethyl)imidazol-5-yl]pyrimidine hydrochloride Trifluoromethylsulphonic anhydride (0.16 ml, 0.93 mmol) was added to a solution of 2-methoxyethanol (73.7 ml, 0.88 mmol) and diisopropylethylamine (0.20 ml, 1.17 mmol) in DCM (1 ml) at −20° C. and the solution stirred for 30 minutes. This mixture was then added to a solution of 2-(3-chloroanilino)-4-(1-triphenylmethylimidazol-4-yl) pyrimidine Method 2; 300 mg, 0.58 mmol) in DCM (5 ml) at −20° C. and the reaction mixture allowed to warm and stirred for 2 hours at ambient temperature. The mixture was extracted between EtOAc and saturated aqueous sodium hydrogen carbonate solution. The organic phase was separated, dried and the volatiles removed by evaporation. The residue was purified by column chromatography, eluting with DCM and 7M methanolic ammonia solution (99.5:0.5 increasing in polarity to 96:4). The purified product was dissolved in either and treated with ethereal hydrogen chloride. The precipitate was collected by filtration washed with ether and dried to give the title compound 132 mg, (69%). NMR: 3.17 (s, 3H), 3.63 (t, 2H), 4.96 (t, 2H), 5.86 (br s, 1H), 7.04 (d, 1H), 7.28–7.44 (m, 2H), 7.60 (d, 1H), 7.88 (s, 1H), 8.56 (s, 1H), 8.64 (d, 1H), 9.28 (s, 1H), 10.0 (s, 1H); m/z: 330.

Example 9

2-(3-Chloroanilino)-4-(imidazol-5-yl)pyrimidine

A mixture of 2-(3-chloroanilino)-4-(1-triphenylmethylimidazol-4-yl)pyrimidine (Method 2; 256 mg, 0.5 mmol) in MeOH (3 ml) and 2M hydrochloric acid (1 ml) was stirred for 15 minutes. The volatiles were removed by evaporation and the residue partitioned between EtOAc and saturated aqueous sodium hydrogen carbonate solution. The organic layer was separated, dried and the solvent removed by evaporation. The residue was purified by column chromatography eluting with DCM and 7M methanolic ammonia solution (99.5:0.5 increasing in polarity to 93:7) to give the title compound 102 mg, (75%) as a solid. NMR: 6.95 (dd, 1H), 7.25–7.33 (m, 2H), 7.73 (dd, 1H), 7.81 (d, 2H), 8.06 (s, 1H), 8.46 (d, 1H), 9.68 (s, 1H), 12.48 (br s, 1H); m/z: 270.

Example 10

2-(3-Chloroanilino)-4-[1-(2-phthalimidoethyl) imidazol-5-yl]pyrimidine

2-Phthalimidoethyl triflate (660 mg, 2.04 mmol) was added to solution of the 2-(3-chloroanilino)-4-(1-triphenylmethylimidazol-4-yl)pyrimidine Method 2; 1.00 g, 1.95 mmol) in DCM (5 ml) and the reaction mixture stirred for 4 hours. The solvent was removed by evaporation and MeOH (6 ml) and 2M hydrochloric acid (1.5 ml) was added to the residue. The mixture was stirred for 5 minutes, the volatiles were removed by evaporation and the residue partitioned between EtOAc and saturated aqueous sodium hydrogen carbonate solution. The resulting precipitate was collected by filtration, washed with water and EtOAc and dried to give the title compound 350 mg, (40%) as a solid. NMR: 3.81–3.96 (m, 2H), 4.77–4.92 (m, 2H), 6.98 (d, 1H), 7.06 (d, 1H), 7.31 (t, 1H), 7.37 (d, 1H), 7.63–7.80 (m, 6H), 7.92 (s, 1H), 8.27 (d, 1H), 9.50 (s, 1H); m/z: 443.

Example 11–12

The following compounds were prepared by an analogous method to that described in Example 10 using with the appropriate starting materials[1], but in the work-up the organic layer was separated, dried, the solvent removed by evaporation and the residue purified by column chromatography eluting with DCM and 7M methanolic ammonia solution (99.5:0.5 increasing in polarity to 93:7).

| Ex | Compound | NMR | m/z |
|---|---|---|---|
| 11 | 2-(3-Chloroanilino)-4-(1-ethylimidazol-5-yl)pyrimidine | 1.26 (t, 3H), 4.56 (q, 2H), 7.00 (d, 1H), 7.21 (d, 1H), 7.30 (t, 1H), 7.57 (d, 1H), 7.87–7.91 (m, 1H), 8.44 (d, 1H), 9.62 (s, 1H) | 300 |
| 12 | 2-(3-Chloroanilino)-4-(1-methylimidazol-5-yl)pyrimidine | 4.03 (s, 3H), 6.95–7.10 (m, 2H), 7.15–7.38 (m, 3H), 7.45–7.60 (m, 2H), 7.65 (s, 1H), 7.87 (s, 1H), 8.38 (d, 1H) | 286 |

[1]In the case of Example 12, the triflate starting material used was trimethylsilymethyl triflate Example 13

4-[1-(2-Aminoethyl)imidazol-5-yl]-2-(3-chloroanilino)pyrimidine

Hydrazine hydrate (54 ml, 1.73 mmol) was added to a suspension of 2-(3-chloroanilino)-4-[1-(2-phthalimidoethyl) imidazol-5-yl]pyrimidine (Example 10; 163 mg, 0.37 mmol) in EtOH (5 ml) and the mixture was heated at reflux for 2 hours. The mixture was allowed to cool, the volatiles removed by evaporation and the residue purified by column chromatography eluting with DCM and 7M methanolic ammonia solution (90:10) to give the title compound 69 mg, (59%) as a solid product. NMR: 1.41 (brs, 2H), 2.99 (t, 2H), 4.55 (t, 2H), 7.00–7.09 (m, 2H), 7.22–7.35 (m, 3H), 7.65–7.70 (m, 2H), 7.73–7.78 (m, 1H), 8.39 (d, 1H); m/z: 315.

Example 14

2-Anilino-4-(1-methylimidazol-5-yl)pyrimidine

Sodium methoxide (2.63 g, 48.7 mmol) was added to a solution of 5-(3-dimethylaminoprop-2-en-1-oyl)-1-methylimidazole Method 4; 2.91 g, 16.2 mmol) and phenylguanidine hydrogen carbonate (3.52 g, 17.9 mmol) in 2-propanol (14 ml) and the reaction mixture heated at reflux for 3 hours. The reaction mixture was allowed to cool and partitioned between EtOAc and saturated aqueous sodium, hydrogen carbonate solution. The organic phase was separated, dried and the solvent removed by evaporation. The residue was purified by column chromatography eluting with DCM and 7M methanolic ammonia solution (97:3) to give the title compound 2.57 g, (64%) as a solid. M/z: 252.

Example 15

4-(1-Methylimidazol-5-yl)-2-(4-sulphamoylanilino) pyrimidine

Chlorosulphonic acid (0.48 ml, 7.16 mmol) was added to a suspension of 2-anilino-4-(1-methylimidazol-5-yl) pyrimidine (Example 14; 449 mg, 1.79 mmol) in thionyl chloride (9 ml) cooled at 0° C. The mixture was allowed to warm to ambient temperature then heated at reflux for 30 minutes. The volatiles were removed by evaporation and the residue dried under high vacuum. 7M methanolic ammonia (30 ml) was added to the residue and the mixture stirred for 10 minutes. The volatiles were removed by evaporation to give the title compound 360 mg, (61%) as a solid product. NMR: 4.04 (s, 3H), 7.15 (s, 2H), 7.27 (d, 1H), 7.73 (d, 2H), 7.84–7.91 (m, 3H), 8.06 (s, 1H), 8.50 (d, 1H), 9.92 (s, 1H); m/z: 331.

Example 16

2-{4-[N-(3-Methoxypropyl)sulphamoyl]anilino}-4-(1-methylimidazol-5-yl)pyrimidine Chlorosulphonic acid (0.22 ml, 3.18 mmol) was added to suspension of 2-anilino-4-(1-methylimidazol-5-yl)pyrimidine (Example 14; 200 mg, 0.80 mmol) in thionyl chloride (4 ml) cooled at 0° C. The mixture was allowed to warm to ambient temperature, stirred for 15 minutes then heated at reflux for 20 minutes. The volatiles were removed by evaporation and the solid residue dried under high vacuum. The residue was suspended in pyridine (3 ml), cooled to −20° C. and diisopropylethyl amine (0.56 ml, 3.98 mmol) followed by 3-methoxypropyl amine (0.16 ml, 1.60 mmol) was added. The reaction mixture was allowed to warm to ambient temperature and stirred for 30 minutes. EtOAc (15 ml) was added and the mixture washed with saturated aqueous sodium hydrogen carbonate solution (15 ml) and then brine (15 ml). The solvent was removed by evaporation and the residue purified by column chromatography eluting with DCM and 2M methanolic ammonia solution (100:0 increasing in polarity to 85:15) to give the title compound 89 mg, (28%) as a solid product. NMR: 1.75 (m, 2H), 2.76 (q, 2H), 3.14 (s, 3H), 3.22–3.30 (m, 2H), 4.01 (s, 3H), 7.25 (d, 1H), 7.34 (t, 1H), 7.70 (d, 2H), 7.77 (s, 1H), 7.83 (s, 1H), 7.91 (d, 2H), 8.47 (d, 1H), 9.92 (s, 1H); m/z 4.03.

Examples 17–25

The following compounds were prepared by an analogous method to that described in Example 15 using the appropriate intermediates.

| Ex | Compound | NMR | m/z |
|---|---|---|---|
| 17 | 4-(1-Methylimidazol-5-yl)-2-[4-(N-propylsulphamoyl)anilino]pyrimidine | 0.77 (t, 3H), 1.35 (m, 2H), 2.67 (q, 2H), 4.01 (s, 3H), 7.25 (d, 1H), 7.34 (t, 1H), 7.69 (d, 2H), 7.77 (s, 1H), 7.83 (s, 1H), 7.90 (d, 2H), 8.47 (d, 1H), 9.92 (s, 1H) | 373 |
| 18 | 2-{4-[N-(2,3-Dihydroxypropyl)sulphamoyl]anilino}-4-(1-methylimidazol-5-yl)pyrimidine | 2.53–2.64 (m, 1H), 2.79–2.90 (m, 1H), 3.25 (t, 2H), 3.39–3.50 (m, 1H), 4.02 (s, 3H), 4.49 (t, 1H), 4.71 (d, 1H), 7.22–7.29 (m, 2H), 7.70 (d, 2H), 7.77 (s, 1H), 7.83 (s, 1H), 7.91 (d, 2H), 8.47 (d, 1H), 9.93 (s, 1H) | 405 |
| 19 | 2-(4-{N-[2-(2-Hydroxyethoxy)ethyl]sulphamoyl}anilino)-4-(1-methylimidazol-5-yl)pyrimidine | 2.88 (q, 2H), 3.24–3.48 (m, 6H), 4.02 (s, 3H), 4.51 (t, 1H), 7.25 (d, 1H), 7.42 (t, 1H), 7.70 (d, 2H), 7.77 (s, 1H), 7.83 (s, 1H), 7.90 (d, 2H), 8.47 (d, 1H), 9.92 (s, 1H) | 419 |
| 20 | 2-{4-[N-(2-Furanylmethyl)sulphamoyl]anilino}-4-(1-methylimidazol-5-yl)pyrimidine | 3.97 (d, 2H), 4.02 (s, 3H), 6.16 (dd, 1H), 6.30 (dd, 1H), 7.25 (d, 1H), 7.47–7.50 (m, 1H), 7.68 (d, 2H), 7.77 (s, 1H), 7.83 (s, 1H), 7.85–7.94 (m, 3H), 8.48 (d, 1H), 9.91 (s, 1H) | 411 |
| 21 | 2-{4-[N-(2-Hydroxyethyl)sulphamoyl]anilino}-4-(1-methylimidazol-5-yl)pyrimidine | 2.77 (q, 2H), 3.55 (q, 2H), 4.02 (s, 3H), 4.61 (t, 1H), 7.25 (d, 1H), 7.33 (t, 1H), 7.70 (d, 2H), 7.77 (s, 1H), 7.83 (s, 1H), 7.90 (d, 2H), 8.47 (d, 1H), 9.91 (s, 1H) | 375 |
| 22 | 2-{4-[N-(Carbamoylmethyl)sulphamoyl]anilino}-4-(1-methylimidazol-5-yl)pyrimidine | 3.29–3.37 (m, 2H), 4.02 (s, 3H), 7.06 (br s, 1H), 7.20 (br s, 1H), 7.25 (d, 1H), 7.58 (t, 1H), 7.71 (d, 2H), 7.77 (s, 1H), 7.83 (s, 1H), 7.90 (d, 2H), 8.47 (d, 1H), 9.93 (s, 1H) | 388 |
| 23 | 4-(1,2-Dimethylimidazol-5-yl)-2-{4-[N-(3-methoxypropyl)sulphamoyl]anilino}pyrimidine | 1.75 (m, 2H), 2.37 (s, 3H), 2.76 (t, 2H), 3.14 (s, 3H), 3.26 (t, 2H), 3.96 (s, 3H), 7.19 (d, 1H), 7.33 (br s, 1H), 7.63 (s, 1H), 7.68 (d, 2H), 7.92 (d, 2H), 8.43 (d, 1H), 9.91 (s, 1H) | 417 |
| 24 | 4-(1,2-Dimethylimidazol-5-yl)-2-{4-[N-(4-fluorobenzyl)sulphamoyl]anilino}pyrimidine | 2.37 (s, 3H), 3.94 (s, 2H), 3.95 (s, 3H), 7.04–7.12 (m, 2H), 7.20 (d, 1H), 7.24–7.29 (m, 2H), 7.63 (s, 1H), 7.70 (d, 2H), 7.88–7.95 (m, 3H), 8.43 (d, 1H), 9.91 (s, 1H) | 453 |
| 25 | 2-{4-[N-(Cyclopropylmethyl)sulphamoyl]anilino}-4-(1,2-dimethylimidazol-5-yl)pyrimidine | 0.00–0.05 (m, 2H), 0.27–0.33 (m, 2H), 0.7–0.8 (m, 1H), 2.34 (s, 3H), 2.59 (t, 2H), 3.91 (s, 3H), 7.15 (d, 1H), 7.44 (t, 1H), 7.60 (s, 1H), 7.66 (d, 2H), 7.87 (d, 2H), 8.39 (d, 1H), 9.86 (s, 1H) | 399 |

Example 26

4-(1,2-Dimethylimidazol-5-yl)-2-(4-{N-[3-(pyrrolidin-2-on-1-yl)propyl]sulphamoyl}anilino)pyrimidine Ethereal hydrogen chloride (1 ml of a 1M solution, 1.0 mmol) was added to a solution of 4-{N-[3-(pyrrolidin-2-on-1-yl)propyl]sulphamoyl}aniline (Method 13, 300 mg, 1.0 mmol) in MeOH (minimum volume). The volatiles were removed by evaporation and cyanamide (50 mg, 1.2 mmol) followed by dimethylacetamide (0.5 ml) were added to the residue. The mixture was heated to 100° C. for 30 minutes. 5-(3-Dimethylaminoprop-2-enoyl)-1,2-dimethylimidazole Method 1; 180 mg, 0.93 mmol) and sodium methoxide (110 mg, 2.0 mmol) were added and the mixture heated at reflux for one hour. The mixture was allowed to cool and was partitioned between EtOAc and aqueous sodium hydrogen carbonate solution. The organic layer was separated, washed with brine, dried ($Na_2SO_4$) and the volatiles removed by evaporation. The residue was purified by column chromatography eluting with DCM and 7M methanolic ammonia solution (96:4) to give the title compound 220 mg, (50%). NMR: 1.48–1.58 (m, 2H), 1.79–1.89 (m, 2H), 2.14 (t, 2H), 2.37 (s, 3H), 2.68 (q, 2H), 3.10 (t, 2H), 3.21 (t, 2H), 3.95 (s, 3H), 7.19 (d, 1H), 7.34 (t, 1H), 7.63 (s, 1H) 7.69 (d, 2H), 7.92 (d, 2H), 8.43 (d, 1H), 9.92 (s, 1H); m/z: 470.

Example 27

The following compound was prepared by an analogous method to that described in Example 26 using the appropriate intermediates

| Ex | Compound | NMR, DMSO-d6, 300 MHZ @ 303.1k | m/z |
|---|---|---|---|
| 27 | 4-(1,2-Dimethyl-imidazol-5-yl)-2-{4-[N-(2-tetrahydrofuranyl-methyl)sulphamoyl]anilino}pyrimidine | 1.45–1.56 (m, 1H), 1.68–1.88 (m, 3H), 2.37 (s, 3H), 2.75 (t, 2H), 3.51–3.58 (m, 1H), 3.63–3.70 (m, 1H), 3.73–3.82 (m, 1H), 3.95 (s, 3H), 7.19 (d, 1H), 7.46 (t, 1H), 7.63 (s, 1H), 7.70 (d, 2H), 7.91 (d, 2H), 8.43 (d, 1H), 9.90 (s, 1H) | 429 |

Example 28

2-Anilino-4-(1-ethyl-2-methylimidazol-5-yl)pyrimidine 5-(3-Dimethylaminopropyl-2-en-1-oyl)-1-ethyl-2-methylimidazole (Method 16; 2.10 g, 10.1 mmol), phenylguanidine hydrogen carbonate (2.2 g, 11.1 mmol) and sodium methoxide (1.2 g, 22.2 mmol) were suspended in anhydrous DMA (15 ml) and the mixture heated at 110° C. for 18 hours. The reaction mixture was allowed to cool to ambient temperature and poured into water (50 ml). The solution was extracted EtOAc (2×50 ml). The combined extracts were washed with water (2×50 ml) and then brine (2×50 ml), dried and the volatiles removed by evaporation. The residue was triturated with ether, collected by filtration and air dried to give the title compound (1.48 g, 53%) as a reddish brown solid. NMR 1.17 (t, 3H), 2.38 (s, 3H), 4.52 (q, 2H), 6.93 (t, 1H), 7.08 (d, 1H), 7.27 (t, 2H), 7.60 (s, 1H), 7.62 (d, 2H), 8.35 (d, 1H), 9.35 (s, 1H); m/z 280.

Examples 29–33

The following compounds were synthesised in an analogous method to Example 28.

| Ex | Compound | NMR | m/z | SM |
|---|---|---|---|---|
| 29 | 2-Anilino-4-(1-methyl-2-ethylimidazol-5-yl)pyrimidine | 1.23 (t, 3H), 2.90 (q, 2H), 3.92 (s, 3H), 6.92 (t, 1H), 7.08 (d, 1H), 7.25 (t, 2H), 7.59 (s, 1H), 7.70 (d, 1H), 8.38 (d, 1H), 9.42 (s, 1H) | 280 | Meth 20 |
| 30 | 2-Anilino-4-[1-(2,2,2-trifluoroethyl)-2-methylimidazol-5-yl]pyrimidine | 2.41 (s, 3H), 5.76 (q, 2H), 6.98 (t, 1H), 7.13 (d, 1H), 7.29 (t, 3H), 7.60 (d, 2H), 7.71 (s, 1H), 8.38 (d, 1H), 8.56 (s, 1H) | 334 | Meth 21 |
| 31[1] | 2-Anilino-4-(1,2,4-trimethylimidazol-5-yl)pyrimidine | 2.26 (s, 3H), 2.32 (s, 3H), 3.72 (s, 3H), 6.85 (d, 1H), 6.94 (dd, 1H), 7.24 (dd, 1H), 7.73 (d, 2H), 8.42 (d, 1H), 9.45 (s, 1H) | 279 | Meth 24 |
| 32[2] | 2-Anilino-4-(1-isopropyl-2-methylimidazol-5-yl)pyrimidine | 1.44 (d, 6H), 2.51 (s, 3H), 5.72 (septuplet, 1H), 6.99 (t, 1H), 7.04 (d, 1H), 7.30 (t, 2H), 7.42 (s, 1H), 7.67 (d, 2H), 8.39 (d, 1H), 9.42 (s, 1H) | 294 | Meth 19 |
| 33[3] | 2-Anilino-4-(1-methyl-2-methoxymethylimidazol-5-yl)pyrimidine | 3.30 (s, 3H) 3.99 (s, 3H), 4.50 (s, 2H), 6.94 (t, 1H), 7.13 (d, 1H), 7.28 (t, 2H), 7.65 (s, 1H), 7.69 (d, 2H), 8.41 (d, 1H), 9.48 (s, 1H) | 296 | Meth 25 |

[1]Reaction heated at 150° C. for 18 hours. Water added, precipitated solid collected by filtration and purified by flash chromatography on silica gel eluting with DCM/MeOH (100:0 increasing in polarity to 95:5).
[2]Solid crystallised from EtOAc.
[3]Purified by flash chromatography on silica gel eluting with DCM/MeOH (100:0 increasing in polarity to 97:3).

Example 34

4-(1,2-Dimethylimidazol-5-yl)-2-(4-mesylaminoanilino)pyrimidine

Methanesulphonyl chloride (0.055 ml, 0.711 mmole) was added to a solution of 4-(1,2-dimethylimidazol-5-yl)-2-(4-aminoanilino)pyrimidine (Example 165; 0.18 g, 0.64 mmole) and pyridine (0.052 ml, 0.64 mmole) in DCM (2.0 mL) cooled at 4° C. The mixture was allowed to warm to ambient temperature. The mixture was partitioned between saturated aqueous sodium hydrogen carbonate solution and EtOAc. The organic layer was separated, the volatiles evaporated and the residue purified by column chromatography on silica gel eluting with DCM/7M methanolic ammonia (96:4) to give the title compound (0.15 g, 65%) as a solid. NMR: 2.36 (s, 3H), 2.90 (s, 3H), 3.91 (s, 3H), 7.06 (d, 1H), 7.14 (d, 2H), 7.57 (s, 1H), 7.64 (d, 2H), 8.33 (d, 1H), 9.37 (br s, 1H), 9.42 (s, 1H); m/z 359.

Example 35

4-(1,2-Dimethylimidazol-5-yl)-2-{4-[N(2-methoxyethyl)sulphamoyl]anilino}pyrimidine Sodium t-butoxide (1.04 g, 10.8 mmol) was added to a degassed solution of 2-amino-4-(1,2-dimethylimidazol-5-yl)pyrimidine (Method 26; 567 mg, 3 mmol), N-(2-methoxyethyl)-4-iodobenzenesulphonamide (Method 40; 1.54 g, 4.5 mmol), tris(dibenzylideneacetone) dipalladium (0) (72 mg, 0.15 mmol) and 2,2'-bis(diphenylphosphino)-1,1'-binaphthyl (102 mg, 0.15 mmol) in dioxane (36 ml) and the mixture heated at 80° C. overnight. The reaction was cooled to room temperature and MeOH (5 ml) was added and the mixture poured onto an Isolute SCX-2 column, eluted first with MeOH (10×30 ml) and the product was then eluted with 2% methanolic ammonia (10×30 ml). The solvent was removed by evaporation and the residue was dissolved in EtOAc (100 ml), washed with water (3×100 ml) and then brine (100 ml), dried and the solvent removed by evaporation to give the title compound (1.01 g, 84%) as a foam. NMR 2.40 (s, 3H), 3.07 (q, 2H), 3.20 (s, 3H), 3.38 (t, 2H), 3.86 (s, 3H), 5.00 (t, 1H), 6.95 (d, 1H), 7.47 (s, 2H), 7.71 (m, 4H), 8.36 (d, 1H); m/z 403.

Examples 36–72

The following compounds were synthesised in an analogous method to Example 35.

| Ex | Compound | NMR | m/z | SM |
|---|---|---|---|---|
| 36 | 4-(1,2-Dimethylimidazol-5-yl)-2-[4-(N-t-butoxycarbonylsulphamoyl)anilino]pyrimidine | 1.40 (s, 9H), 2.49 (s, 3H), 3.96 (s, 3H), 7.03 (d, 1H), 7.38 (s, 1H), 7.82 (d, 2H), 7.96 (d, 2H), 8.08 (s, 1H), 8.43 (d, 1H) | 445 | Meth 54, Meth 26 |
| 37 | 4-(1-Ethyl-2-methyl-imidazol-5-yl)-2-{4-[N-(2-methoxyethyl)sulphamoyl]anilino}pyrimidine | 1.25 (t, 3H), 2.40 (s, 3H), 3.05 (q, 2H), 3.20 (s, 3H), 3.36 (t, 2H), 4.43 (q, 2H), 4.92 (t, 1H), 6.95 (d, 1H), 7.32 (s, 1H), 7.50 (s, 1H), 7.72 (m, 4H), 8.35 (d, 1H) | 417 | Meth 40, Meth 27 |
| 38 | 4-(1,2-Dimethylimidazol-5-yl)-2-{4-[N-(2,2-dimethyl-1,3-dioxalon-4-ylmethyl)sulphamoyl]anilino}pyrimidine | 1.20 (s, 3H), 1.25 (s, 3H), 2.40 (s, 3H), 2.91 (m, 1H), 3.12 (m, 1H), 3.60 (m, 1H), 3.86 (s, 3H), 3.92 (m, 1H), 4.13 (m, 1H), 4.83 (t, 1H), 6.95 (d, 1H), 7.38 (s, 1H), 7.49 (s, 1H), 7.72 (m, 4H), 8.35 (d, 1H) | 459 | Meth 42, Meth 26 |
| 39 | 4-(1,2-Dimethylimidazol-5-yl)-2-{4-[N-(2-benzyloxyethyl)sulphamoyl]anilino}pyrimidine | 2.40 (s, 3H), 3.12 (q, 2H), 3.46 (t, 2H), 3.90 (s, 3H), 4.37 (s, 2H), 4.95 (t, 1H), 6.95 (d, 1H), 7.20 (m, 5H), 7.40 (s, 1H), 7.46 (s, 1H), 7.73 (m, 4H), 8.33 (d, 1H) | 479 | Meth 43, Meth 26 |
| 40 | 4-(1,2-Dimethylimidazol-5-yl)-2-{4-[N-(2,2-dimethoxy-ethyl)sulphamoyl]anilino}pyrimidine | 2.40 (s, 3H), 3.00 (t, 2H), 3.28 (s, 6H), 3.89 (s, 3H), 4.28 (t, 1H), 4.75 (t, 1H), 6.95 (d, 1H), 7.40 (s, 1H), 7.48 (s, 1H), 7.76 (m, 4H), 8.32 (d, 1H) | 433 | Meth 44, Meth 26 |
| 41 | 4-(1-Ethyl-2-methyl-imidazol-5-yl)-2-(4-{N-[2-(2-tetrahydrofur-2-yl)methyl]sulphamoyl}anilino)pyrimidine | 1.24 (t, 3H), 1.50 (m, 1H), 1.80 (m, 3H), 2.43 (s, 3H), 2.80 (t, 1H), 3.62 (q, 1H), 3.74 (m, 1H), 3.84 (m, 1H), 4.73 (q, 2H), 7.32 (d, 1H), 7.56 (t, 1H), 7.78 (d, 2H), 7.94 (d, 2H), 8.50 (d, 1H), 9.90 (s, 1H) | 441 | Meth 45, Meth 27 |
| 42[1] | 4-(1-Ethyl-2-methyl-imidazol-5-yl)-2-{4-[N-(3-methoxypropyl)sulphamoyl]anilino}pyrimidine | 1.18 (t, 3H), 1.58 (m, 2H), 2.40 (s, 3H), 2.78 (q, 2H), 3.16 (s, 3H), 3.30 (m, 2H), 4.58 (q, 2H), 7.20 (d, 1H), 7.36 (t, 1H), 7.70 (m, 3H), 7.90 (d, 2H), 8.41 (d, 1H), 9.80 (s, 1H) | 431 | Meth 46, Meth 27 |
| 43[1] | 4-(1-Ethyl-2-methyl-imidazol-5-yl)-2-{4-[N-(cyclopropylmethyl)sulphamoyl]anilino}pyrimidine | 0.01 (q, 2H), 0.40 (q, 2H), 0.81 (m, 1H), 1.24 (t, 3H), 2.40 (s, 3H), 2.78 (t, 2H), 4.42 (q, 2H), 4.56 (t, 1H), 6.96 (d, 1H), 7.30 (s, 1H), 7.50 (s, 1H), 7.68 (d, 2H), 7.76 (d, 2H), 8.36 (d, 1H) | 413 | Meth 41, Meth 27 |
| 44 | 4-(1,2-Dimethylimidazol-5-yl)-2-{4-[N-(2-methoxyethyl)-N-methylsulphamoyl]anilino}pyrimidine | 2.40 (s, 3H), 2.78 (s, 3H), 3.16 (t, 2H), 3.22 (s, 3H), 3.45 (t, 3H), 3.89 (s, 3H), 6.95 (d, 1H), 7.37 (s, 1H), 7.46 (s, 1H), 7.70 (m, 4H), 8.38 (d, 1H) | 417 | Meth 62, Meth 26 |
| 45[1] | 4-(1-Ethyl-2-methyl-imidazol-5-yl)-2-{4-[N-(2-methoxyethyl)-N-methyl-sulphamoyl]anilino}pyrimidine | 1.24 (t, 3H), 2.40 (s, 3H), 2.78 (s, 3H), 3.16 (t, 2H), 3.23 (s, 3H), 3.45 (t, 3H), 4.43 (q, 2H), 6.95 (d, 1H), 7.26 (s, 1H), 7.46 (s, 1H), 7.70 (m, 4H), 8.38 (d, 1H) | 431 | Meth 62, Meth 27 |
| 46[1] | 4-(1,2-Dimethylimidazol-5-yl)-2-(4-mesylanilino)pyrimidine | 2.40 (s, 3H), 2.98 (s, 3H), 3.86 (s, 3H), 6.96 (d, 1H), 7.40 (s, 1H), 7.51 (s, 1H), 7.80 (m, 4H), 8.38 (d, 1H) | 344 | Meth 65, Meth 26 |
| 47 | 4-(1,2-Dimethylimidazol-5-yl)-2-{4-[N-(3-morpholinopropyl)-N-methylsulphamoyl]anilino}pyrimidine | 1.76 (m, 2H), 2.40 (m, 6H), 2.46 (s, 3H), 2.73 (s, 3H), 3.10 (t, 3H), 7.71 (m, 4H), 3.97 (s, 3H), 7.03 (d, 1H), 7.37 (s, 1H), 7.53 (s, 1H), 7.77 (m, 4H), 8.40 (d, 1H) | 486 | Meth 63 |
| 48[1] | 4-(1,2-Dimethylimidazol-5-yl)-2-{4-[3-(N,N-dimethyl-amino)propylsulphonyl]anilino}pyrimidine | 1.87 (m, 2H), 2.16 (s, 6H), 2.33 (t, 2H), 2.50 (s, 3H), 3.16 (m, 2H), 3.96 (s, 3H), 7.02 (d, 1H), 7.45 (s, 1H), 7.57 (s, 1H), 7.83 (m, 4H), 8.41 (d, 1H) | 415 | Meth 70, Meth 26 |
| 49 | 4-(1,2-Dimethylimidazol-5-yl)-2-[4-(3,3,3-trifluoropropylsulphonyl)anilino]pyrimidine | 2.48 (s, 3H), 2.57 (m, 2H), 3.31 (m, 2H), 3.96 (s, 3H), 7.03 (d, 1H), 7.56 (s, 1H), 7.84 (m, 4H), 8.40 (d, 1H) | 426 | Meth 71, Meth 26 |
| 50[1] | 4-(1,2-Dimethylimidazol-5-yl)-2-(4-butylsulphonyl-anilino)pyrimidine | 0.80 (t, 3H), 1.31 (m, 2H), 1.51 (m, 2H), 2.38 (s, 3H), 3.19 (m, 2H), 3.96 (s, 3H), 7.20 (d, 1H), 7.61 (s, 1H), 7.76 (d, 2H), 7.98 (d, 2H), 8.43 (d, 1H), 10.05 (s, 1H) | 386 | Meth 72, Meth 26 |
| 51[1] | 4-(1,2-Dimethylimidazol-5-yl)-2-[4-(3-methoxy-propyl sulphonyl)anilino]pyrimidine | 2.02 (m, 2H), 2.48 (s, 3H), 3.20 (m, 2H), 3.27 (s, 3H), 3.45 (t, 2H), 3.95 (s, 3H), 7.03 (d 1H), 7.56 (s, 2H), 7.83 (s, 4H), 8.40 (d, 1H) | 402 | Meth 74, Meth 26 |
| 52[1] | 4-(1-Ethyl-2-methyl-imidazol-5-yl)-2-(4-{N-[2-(methoxy-methoxy)ethyl]sulphamoyl}anilino)pyrimidine | 1.34 (t, 3H), 2.50 (s, 3H), 3.17 (q, 2H), 3.31 (s, 3H), 3.59 (t, 2H), 4.53 (m, 4H), 5.09 (t, 1H), 7.03 (d, 1H), 4.39 (s, 1H), 7.56 (s, 1H), 7.80 (m, 4H), 8.39 (d, 1H) | 447 | Moth 39, Meth 27 |
| 53[1] | 4-(1-Ethyl-2-methyl-imidazol-5-yl)-2-[4-(N-cyclopropylsulphamoyl)anilino]pyrimidine | 0.33 (m, 2H), 0.45 (m, 2H), 1.12 (t, 3H), 2.08 (m, 1H), 2.40 (s, 3H), 4.59 (q, 2H), 7.16 (d, 1H), 7.68 (m, 3H), 7.86 (d, 2H), 8.41 (d, 1H), 9.80 (s, 1H) | 399 | Meth 47, Meth 27 |

-continued

| Ex | Compound | NMR | m/z | SM |
|---|---|---|---|---|
| 54[2] | 4-(1-Ethyl-2-methyl-imidazol-5-yl)-2-{4-[N-(4-methylthiazol-2-ylmethyl)sulphamoyl]anilino}pyrimidine | 1.24 (t, 3H), 2.23 (s, 3H), 2.70 (s, 3H), 4.10 (d, 2H), 4.70 (q, 2H), 7.12 (s, 1H), 7.38 (d, 1H), 7.73 (d, 2H), 7.86 (d, 2H), 8.40 (m, 2H), 8.65 (d, 1H), 10.11 (s, 1H) | 470 | Meth 48, Meth 27 |
| 55[2] | 4-(1-Ethyl-2-methyl-imidazol-5-yl)-2-{4-[N-(3-methylisoxazol-5-ylmethyl)sulphamoyl]anilino}pyrimidine | 1.24 (t, 3H), 2.10 (s, 3H), 2.68 (s, 3H), 4.10 (d, 2H), 4.70 (q, 2H), 6.03 (s, 1H), 7.37 (d, 1H), 7.69 (d, 2H), 7.84 (d, 2H), 8.20 (t, 1H), 8.36 (s, 1H), 8.63 (d, 1H), 10.09 (s, 1H) | 454 | Meth 49, Meth 27 |
| 56[2] | 4-(1-Ethyl-2-methyl-imidazol-5-yl)-2-{4-[N-(1,4-dioxan-2-ylmethyl)sulphamoyl]anilino}pyrimidine | 1.23 (t, 3H), 2.70 (s, 3H), 2.74 (t, 2H), 3.10 (m, 1H), 3.70 (m, 6H), 4.70 (q, 2H), 7.35 (d, 1H), 7.59 (t, 1H), 7.72 (d, 2H), 7.86 (d, 2H), 8.40 (s, 1H), 8.63 (d, 1H), 10.09 (brs, 1H) | 459 | Meth 50, Meth 27 |
| 57 | 5-Chloro-4-(1,2-dimethylimidazol-5-yl)-2-[4-(N-propylsulphamoyl)anilino]pyrimidine | 0.78 (t, 3H), 1.35 (m, 2H), 2.4 (s, 3H), 2.67 (m, 2H), 3.8 (s, 3H), 7.33 (t, 1H), 7.65 (s, 1H), 7.72 (d, 2H), 7.87 (d, 2H), 8.63 (s, 1H), 10.14 (s, 1H) | 419 M-H- | Meth 111, Meth 51 |
| 58 | 5-Chloro-4-(1,2-dimethylimidazol-5-yl)-2-{4-[N-(cyclopropylmethyl)sulphamoyl]anilino}pyrimidine | 0.0 (m, 2H), 0.27 (m, 2H), 0.72 (m, 1H), 2.35 (s, 3H), 2.57 (t, 2H), 3.73 (s, 3H), 7.43 (t, 1H), 7.6 (s, 1H), 7.66 (d, 2H), 7.8 (d, 2H), 8.55 (s, 1H), 10.08 (s, 1H). | 431 M-H- | Meth 111, Meth 41 |
| 59 | 5-Chloro-4-(1,2-dimethylimidazol-5-yl)-2-{4-[N-(3-methoxypropyl)sulphamoyl]anilino}pyrimidine | 1.57 (m, 2H), 2.42 (s, 3H), 2.75 (m, 2H), 3.13 (s, 3H), 3.25 (m, 2H), 3.78 (s, 3H), 7.35 (t, 1H), 7.63 (s, 1H), 7.7 (d, 2H), 7.87 (d, 2H), 8.6 (s, 1H), 10.15 (s, 1H). | 449 M-H- | Meth 111, Meth 46 |
| 60 | 5-Chloro-4-(1,2-dimethylimidazol-5-yl)-2-{4-[N-(t-butyl)sulphamoyl]anilino}pyrimidine | 1.07 (s, 9H), 2.4 (s, 3H), 3.78 (s, 3H), 7.27 (s, 1H), 7.65 (s, 1H), 7.73 (d, 2H), 7.83 (d, 2H), 8.6 (s, 1H), 10.12 | 433 M-H- | Meth 111, Meth 52 |
| 61[3] | 4-[1-(2-Methoxyethyl)-2-methylimidazol-5-yl]-2-{4-[N-(2-methoxyethyl)sulphamoyl]anilino}pyrimidine | 2.40 (s, 3H), 2.89 (s, 3H), 3.12 (s, 3h), 3.18 (s, 3H), 3.31 (t, 2H), 3.52 (t, 2H), 4.77 (t, 2H), 7.24 (d, 1H), 7.50 (brs, 1H), 7.71 (d, 3H), 7.88 (d, 2H), 8.42 (d, 1H), 9.81 (s, 1H) | 447 | Meth 28, Meth 40 |
| 62[4] | 4-[1-(1-Butene-4-yl)-2-methylimidazol-5-yl]-2-{4-[N-(2-methoxyethyl)sulphamoyl]anilino}pyrimidine | 2.29 (q, 2H), 2.39 (s, 3H), 2.88 (brq, 2H), 3.18 (s, 3H), 3.30 (t, 2H), 4.63 (t, 2H), 4.84 (d, 1H), 4.88 (s, 1H), 5.62 (m, 1H), 7.22 (d, 1H), 7.48 (brt, 1H), 7.67 (s, 1H), 7.71 (d, 2H), 7.87 (d, 2H), 8.44 (d, 1H), 9.82 (s, 1H) | 443 | Meth 29, Meth 40 |
| 63[5] | 2-Anilino-5-bromo-4-(1,2-dimethylimidazol-5-yl)pyrimidine | 2.39 (s, 3H), 3.70 (s, 3H), 6.99 (dd, 1H), 7.30 (dd, 1H), 7.60 (s, 1H), 7.64 (d, 2H), 8.60 (s, 1H), 9.70 (s, 1H) | 343 | Meth 61 |
| 64[6] | 4-(1-Methyl-2-ethylimidazol-5-yl)-2-{4-[N-(tetrahydrofur-2-ylmethyl)sulphamoyl]anilino}pyrimidine | 1.41 (t, 3H), 1.96 (m, 4H), 2.77 (q, 2H), 2.93 (m, 1H), 3.16 (m, 2H), 3.73 (m, 2H), 3.96 (s, 3H), 4.82 (m, 1H), 7.01 (d, 1H), 7.38 (s, 1H), 7.53 (s, 1H), 7.80 (m, 4H), 8.39 (d, 1H) | 443 | Meth 30, Meth 45 |
| 65[6] | 4-(1-Methyl-2-ethylimidazol-5-yl)-2-{4-[N-(2-methoxyethyl)sulphamoyl]anilino}pyrimidine | 1.39 (t, 3H), 2.78 (q, 2H), 3.13 (q, 2H), 3.28 (s, 3H), 3.45 (t, 2H), 3.95 (s, 3H), 4.92 (t, 1H), 7.03 (d, 1H), 7.40 (s, 1H), 7.58 (s, 1H), 7.80 (m, 4H), 8.39 (d, 1H) | 417 | Meth 30, Meth 40 |
| 66[7] | 4-(1-Methyl-2-isopropyl-imidazol-5-yl)-2-{4-[N-(2-methoxyethyl)sulphamoyl]anilino}pyrimidine | 1.40 (t, 3H), 3.15 (q, 2H), 3.30 (s, 3H), 3.42 (t, 2H), 3.96 (s, 3H), 4.98 (t, 1H), 7.03 (d, 1H), 7.49 (s, 1H), 7.58 (s, 1H), 7.80 (m, 4H), 8.40 (d, 1H) | 431 | Meth 31, Meth 40 |
| 67[7] | 4-(1-Methyl-2-isopropyl-imidazol-5-yl)-2-{4-[N-(cyclopropylmethyl)sulphamoyl]anilino}pyrimidine | 0.08 (m, 2H), 0.39 (m, 2H), 0.84 (m, 1H), 1.30 (d, 6H), 2.67 (m, 2H), 3.20 (m, 1H), 3.96 (s, 3H), 7.27 (d, 1H), 7.50 (t, 1H), 7.69 (s, 1H), 7.75 (d, 2H), 7.97 (d, 2H), 8.43 (d, 1H), 9.93 (s, 1H) | 427 | Meth 31, Meth 41 |
| 68[7] | 4-(1-Methyl-2-isopropyl-imidazol-5-yl)-2-{4-[N-(tetrahydrofur-2-ylmethyl)sulphamoyl]anilino}pyrimidine | 1.41 (d, 6H), 1.90 (m, 3H), 2.94 (m, 1H), 3.15 (m, 2H), 3.72 (q, 1H), 3.80 (q, 1H), 3.95 (m, 1H), 4.04 (s, 3H), 4.82 (t, 1H), 7.08 (d, 1H), 7.36 (s, 1H), 7.60 (s, 1H), 7.82 (m, 4H), 8.41 (d, 2H) | 457 | Meth 31, Meth 45 |
| 69[6] | 4-(1-Methyl-2-ethylimidazol-5-yl)-2-{4-[N-(cyclopropylmethyl)sulphamoyl]anilino}pyrimidine | 0.10 (m, 2H), 0.45 (m, 2H), 0.91 (m, 1H), 1.30 (t, 3H), 2.82 (m, 4H), 3.96 (s, 3H), 4.76 (m, 1H), 7.03 (d, 1H), 7.46 (s, 1H), 7.58 (s, 1H), 7.82 (m, 4H), 8.40 (d, 1H) | 413 | Meth 30, Meth 41 |
| 70[7] | 4-(1-Methyl-2-trifluoromethylimidazol-5-yl)-2-{4-[N-(tetrahydrofur-2-ylmethyl)sulphamoyl]anilino}pyrimidine | 1.51 (m, 1H), 1.78 (m, 3H), 2.74 (t, 2H), 3.56 (m, 1H), 3.65 (q, 1H), 3.76 (m, 1H), 4.16 (s, 3H), 7.36 (d, 1H), 7.49 (t, 1H), 7.73 (d, 2H), 7.90 (m, 3H), 8.60 (d, 1H), 10.10 (s, 1H) | 483 | Meth 32, Meth 45 |
| 71 | 5-Chloro-4-(1,2-dimethylimidazol-5-yl)-2-[4-(N-t-butyl-N-methylsulphamoyl)anilino]pyrimidine | 1.23 (s, 9H), 2.42 (s, 3H), 2.85 (s, 3H), 3.77 (s, 3H), 7.65 (s, 1H), 7.7 (d, 2H), 7.87 (d, 2H), 8.62 (s, 1H), 10.17 (s, 1H) | 447 M-H- | Meth 111, Meth 64 |
| 72 | 4-(1-Ethyl-2-methylimidazol-5-yl)-2-[4-(N-allylsulphamoyl)anilino]pyrimidine | 1.20 (t, 3H), 2.39 (s, 3H), 3.40 (m, 2H), 4.57 (q, 2H), 5.00 (d, 1H), 5.14 (d, 1H), 5.67 (m, 1H), 7.21 (d, | 399 | Meth 27, Meth 53 |

-continued

| Ex | Compound | NMR | m/z | SM |
|----|----------|-----|-----|-----|
| | | 1H), 7.59 (t, 1H), 7.68 (s, 1H), 7.70 (d, 2H), 7.89 (d, 2H), 8.43 (d, 1H), 9.82 (s, 1H) | | |

[1] Purified by flash chromatography on silica gel eluting with DCM/2% methanolic ammonia (100:0 increasing in polarity to 95:5).
[2] Purified by preparative HPLC (gradient of $H_2O:CH_3CN$ (5:95 increasing in polarity to 95:5) containing 0.2% TFA over 8 min on a 21 × 100 mm RPB base deactivated C18 column).
[3] Reaction mixture evaporated before aqueous work-up with EtOAc extraction. The crude product was purified by flash chromatography on silica gel eluting with DCM/2% methanolic ammonia (100:0 increasing in polarity to 92:8).
[4] Reaction mixture evaporated before aqueous work-up with EtOAc extraction. The crude product was purified by flash chromatography on silica gel eluting with DCM/MeOH (98:2 increasing in polarity to 92:8).
[5] Purified by flash chromatography eluting with DCM/MeOH (100:0 increasing in polarity to 95:5).
[6] Purified by flash chromatography eluting with EtOAc/MeOH (100:0 increasing in polarity to 80:20).
[7] Purified by flash chromatography eluting with EtOAc/MeOH (100:0 increasing in polarity to 90:10).

Example 73

4-(1,2-Dimethylimidazol-5-yl)-2-(4-{N-[2-(2-methoxyethoxy)ethyl]sulphamoyl}anilino)pyrimidine hydrochloride 1M Ethereal hydrogen chloride (4 ml) was added to solution of 4-(1,2-dimethylimidazol-5-yl)-2-(4-(N-t-butoxycarbonyl)-N-[2-(2-methoxyethoxy)ethyl]sulphamoyl)anilino)pyrimidine (Method 55; 77 mg, 0.14 mmol) in anhydrous dioxane (2 ml) and the mixture stirred at ambient temperature for 5 days. The volatiles were removed by evaporation and the residue triturated with ether, collected by filtration, washed with ether (2×10 ml) and dried to give the title compound (65 mg (96%) as a yellow solid. NMR 2.70 (s, 3H), 2.86 (m, 2H), 3.18 (s, 3H), 3.36 (m, 4H), 3.42 (m, 2H), 4.08 (s, 3H), 7.38 (d, 1H), 7.58 (s, 1H), 7.74 (d, 2H), 7.93 (d, 2H), 8.40 (s, 1H), 8.69 (d, 1H), 10.25 (s, 1H); m/z 447.

Examples 74–75

The following compounds were synthesised in an analogous method to Example 73.

| Ex | Compound | NMR | m/z | SM |
|----|----------|-----|-----|-----|
| 74 | 4-(1,2-Dimethylimidazol-5-yl)-2-[4-(N-{2-[2-(2-methoxyethoxy)ethoxy]ethyl}sulphamoyl)anilino]pyrimidine hydrochloride | 2.63 (s, 3H), 2.84 (m, 2H), 3.20 (s, 3H), 3.40 (m, 10H), 4.08 (s, 3H), 7.38 (d, 1H), 7.48 (m, 1H), 7.73 (d, 2H), 7.90 (d, 2H), 8.38 (s, 1H), 8.66 (d, 1H), 10.22 (s, 1H) | 491 | Meth 56 |
| 75 | 4-(1,2-Dimethylimidazol-5-yl)-2-{4-[N-(2-{2-[2-(2-methoxyethoxy)ethoxy]ethyl}sulphamoyl]anilino}pyrimidine hydrochloride | 2.68 (s, 3H), 2.85 (m, 2H), 3.20 (s, 3H), 3.40 (m, 14H), 4.08 (s, 3H), 7.32 (d, 1H), 7.46 (m, 1H), 7.73 (d, 2H), 7.89 (d, 2H), 8.40 (s, 1H), 8.62 (d, 1H), 10.22 (s, 1H) | 535 | Meth 57 |

Example 76

4-(1,2-Dimethylimidazol-5-yl-2-{4-[N-(2-mesylethyl)sulphamoyl]anilino}pyrimidine 4-Dimethylaminopyridine (3 mg, 0.025 mmol) and 3-methyoxypropylamine (200 μl, 2 mmol) were added to a solution of 4-(1,2-dimethylimidazol-5-yl)-2-(4-(fluorosulphonyl)anilino)pyrimidine (Method 59; 87 mg, 0.25 mmol) in NMP (1 mL) and the mixture heated at 100° C. for 18 hours. The mixture was allowed to cool to ambient temperature and the solvent removed by evaporation. The residue was purified by preparative LCMS (constant flow of 5% v/v (35% $NH_3$ in MeOH) with a gradient of $H_2O:CH_3CN$ (5:95 increasing in polarity to 95:5) over 7.5 min) to give the title compound (91 mg, 81%) as a solid. NMR 2.38 (s, 3H), 2.97 (s, 3H), 3.11 (m, 2H), 3.21 (m, 2H), 3.95 (s, 3H), 7.20 (d, 1H), 7.61 (s, 1H), 7.75 (m, 3H), 7.95 (d, 2H), 8.43 (d, 1H), 9.95 (s, 1H); m/z 451.

Examples 77–79

The following compounds were synthesised in an analogous method to Example 76.

| Ex | Compound | NMR | m/z |
|----|----------|-----|-----|
| 77 | 4-(1,2-Dimethylimidazol-5-yl)-2-{4-[N-(3-morpholinopropyl)sulphamoyl]anilino}pyrimidine | 1.58 (m, 2H), 2.33 (m, 9H), 3.02 (t, 2H), 3.64 (m, 5H), 3.90 (s, 3H), 6.95 (d, 1H), 7.45 (m, 2H), 7.72 (m, 4H), 8.35 (d, 1H) | 472 |
| 78 | 4-(1,2-Dimethylimidazol-5-yl)-2-(4-{N-[2-(N,N-dimethylamino)ethyl]sulphamoyl}anilino)pyrimidine | 2.01 (s, 6H), 2.24 (t, 2H), 2.40 (s, 3H), 2.91 (t, 2H), 3.93 (s, 3H), 6.95 (d, 1H), 7.42 (m, 2H), 7.72 (m, 4H), 8.34 (d, 1H) | 416 |
| 79 | 4-(1,2-Dimethylimidazol-5-yl)-2-{4-[N-(2-piperidin-1-ylethyl)sulphamoyl]anilino}pyrimidine | 1.40 (m, 6H), 2.13 (m, 3H), 2.30 (m, 6H), 2.89 (t, 2H), 3.90 (s, 3H), 6.95 (d, 1H), 7.45 (m, 2H), 7.72 (m, 4H), 8.35 (d, 1H) | 456 |

Example 80

4-[1-(2-Methoxyethyl)-2-methylimidazol-5-yl]-2-{4-[N-(tetrahydrofur-2-ylmethyl)sulphamoyl]anilino}pyrimidine A mixture of 4-[1-(2-methoxyethyl)-2-methylimidazol-5-yl]-2-N-(4-fluorosulphonylanilino)pyrimidine (Method 60; 200 mg, 0.51 mmole) and polystyrene supported dimethylaminopyridine (800 mg: 1.6 mmol/g resin) in 1-methyl-2-pyrrolidone (4 ml) was stirred for 10 minutes at ambient temperature. Tetrahydrofurfurylamine (258 mg, 2.55 mmol) was added and the reaction mixture heated at 90° C. for 40 hours then at 100° C. for 48 hours. The volatiles were removed by evaporation and the residue purified by column chromatography on silica gel eluting with DCM/MeOH (99:1 increasing in polarity to 96:4) to give a purified product (120 mg) was triturated with ether, collected by filtration and dried at 80° C. under vacuum to give the title compound (55 mg, 23%). NMR 1.52 (m, 1H), 1.70–1.88 (m, 3H), 2.39 (s, 3H), 2.75 (m, 2H), 3.10 (s, 3H), 3.49 (t, 2H), 3.55 (m, 1H), 3.67 (m, 1H), 3.78 (m, 1H), 4.74 (t, 2H), 7.23 (d, 1H), 7.49 (t, 1H), 7.70 (d, 3H), 7.85 (d, 2H), 8.42 (d, 1H), 9.79 (s, 1H); m/z 473.

Examples 81–82

The following compounds were synthesised in an analogous to Example 80.

| Ex | Compound | NMR | m/z |
|---|---|---|---|
| 81[1] | 4-[1-(2-Methoxyethyl)-2-methylimidazol-5-yl]-2-{4-[N-(cyclopropylmethyl)sulphamoyl]anilino}pyrimidine | 0.06 (m, 2H), 0.34 (m, 2H), 0.79 (m, 1H), 2.40 (s, 3H), 2.62 (t, 2H), 3.11 (s, 3H), 3.50 (t, 2H), 4.76 (t, 2H), 7.24 (d, 1H), 7.50 (t, 1H), 7.69 (s, 1H), 7.70 (d, 2H), 7.87 (d, 2H), 8.42 (d, 1H), 9.79 (s, 1H) | 443 |
| 82[2] | 4-[1-(2-Methoxyethyl)-2-methylimidazol-5-yl]-2-{4-[N-(3-methoxypropyl)sulphamoyl]anilino}pyrimidine | 1.60 (m, 2H), 2.40 (s, 3H), 2.77 (brt, 2H), 3.12 (s, 3H), 3.15 (s, 3H), 3.28 (m, 2H), 3.52 (t, 2H), 4.74 (t, 2H), 7.24 (d, 1H), 7.36 (brs, 1H), 7.70 (d, 3H), 7.88 (d, 2H), 8.40 (d, 1H), 9.80 (s, 1H) | 461 |

[1]Purified by column chromatography eluting with DCM/MeOH (98:2 increasing in polarity to 90:10).
[2]Purified by column chromatography eluting with DCM/MeOH (98:2 increasing in polarity to 95:5).

Example 83

4-(1-Ethyl-2-methylimidazol-5-yl)-2-(4-(N-(hydroxyethyl)sulphamoyl)anilino)pyrimidine Chlorosulphonic acid (150 μL, 2.16 mmol) was added dropwise to solution of 2-anilino-4-(1-ethyl-2-methylimidazol-5-yl)pyrimidine (Example 28; 150 mg, 0.54 mmol) in thionyl chloride (3 ml) cooled at 0° C. and the mixture stirred at 0° C. for 10 minutes then heated at 90° C. for 90 minutes. The volatiles were removed by evaporation and the residue was dried under high vacuum (<2 mmHg) for 1 hour. The resulting solid was placed under nitrogen and a solution of ethanolamine (494 mg, 8.1 mmol) in MeOH (3 ml) added. The mixture was stirred for 30 minutes and the volatiles were evaporated in vacuo. Water (20 ml) was added and the precipitated solid was collected by filtration, washed with water (2×10 ml) and ether (2×10 ml) and and dried under vacuum at 60° C. to yield the title compound (177 mg, 81%) as a beige solid. NMR 1.22 (t, 3H), 2.41 (s, 3H), 2.80 (s, 2H), 3.38 (q, 2H), 4.63 (m, 3H), 7.20 (d, 1H), 7.36 (s, 1H), 7.77 (s, 1H), 7.82 (d, 2H), 7.91 (d, 2H), 8.34 (d, 1H), 9.85, (s, 1H); m/z 403.

Examples 84–125

The following compounds were synthesised in an analogous method to Example 83.

| Ex | Compound | NMR | m/z | SM |
|---|---|---|---|---|
| 84 | 4-(1-Ethyl-2-methyl-imidazol-5-yl)-2-{4-[N-(3-hydroxy-2,2-dimethyl-propyl)sulphamoyl]anilinopyrimidine | 0.76 (s, 6H), 1.20 (t, 3H), 2.40 (s, 3H), 2.57 (m, 2H), 3.06 (d, 2H), 4.40 (t, 1H), 4.55 (q, 2H), 7.20 (m, 2H), 7.68 (m, 3H), 7.84 (d, 2H), 8.40 (d, 1H), 9.80 (s, 1H) | 445 | Ex 28 |
| 85 | 4-(1-Ethyl-2-methylimidazol-5-yl)-2-{4-[N-(3-hydroxypropyl)sulphamoyl]anilino}pyrimidine | 1.18 (t, 3H), 1.50 (m, 2H), 2.38 (s, 3H), 2.78 (t, 2H), 3.38 (q, 2H), 4.38 (t, 1H), 4.58 (q, 2H), 7.20 (d, 1H), 7.28 (s, 1H), 7.68 (m, 3H), 7.84 (d, 2H), 8.41 (d, 1H), 9.80 (s, 1H) | 417 | Ex 28 |
| 86 | 4-(1,2-Dimethylimidazol-5-yl)-2-[4-(N-allyl-sulphamoyl)anilino]pyrimidine | 2.38 (s, 3H), 3.4 (t, 2H), 3.96 (s, 3H), 5.0 (d, 1H), 5.13 (d, 1H), 5.65 (m, 1H), 7.2 (d, 1H), 7.55 (t, 1H), 7.63 (s, 1H), 7.68 (d, 2H), 7.9 (d, 2H), 8.43 (d, 1H), 9.93 (s, 1H) | 383 (M-H)- | Ex 5 |
| 87 | 4-(1,2-Dimethylimidazol-5-yl)-2-{4-[N-(1-propyn-3-yl)sulphamoyl]anilino}pyrimidine | 2.50 (s, 3H) + DMSO peak), 3.02 (s, 1H), 3.63 (m, 2H), 4.03 (s, 3H), 7.25 (d, 1H), 7.72 (d, 2H), 7.93 (m, 3H), 8.0 (d, 2H), 8.55 (d, 1H), 10.07 (s, 1H) | 381 (M-H)- | Ex 5 |
| 88 | 4-(1,2-Dimethylimidazol-5-yl)-2-{4-[N-(2,2-dimethyl-3-hydroxy-propyl)sulphamoyl]anilino}pyrimidine | 0.73 (s, 6H), 2.38 (s, 3H), 2.55 (d, 2H), 3.07 (d, 2H), 3.95 (s, 3H), 4.4 (t, 1H), 7.15 (s, 1H), 7.2 (d, 1H), 7.63 (s, 1H), 7.68 (d, 2H), 7.9 (d, 2H), 8.43 (d, 1H), 9.97 (s, 1H) | 429 (M-H)- | Ex 5 |
| 89 | 4-(1,2-Dimethylimidazol-5-yl)-2-{4-[N-(3-hydroxy propyl)sulphamoyl]anilino}pyrimidine | 1.5 (m, 2H), 2.37 (s, 3H), 2.76 (m, 2H), 3.33 (m, 2H), 3.95 (s, 3H), 4.36 (t, 1H), 7.2 (d, 1H), 7.27 (t, 1H), 7.63 (s, 1H), 7.67 (d, 2H), 7.9 (d, 2H), 8.43 (d, 1H), 9.92 (s, 1H) | 401 (M-H)- | Ex 5 |

-continued

| Ex | Compound | NMR | m/z | SM |
|---|---|---|---|---|
| 90 | 4-(1,2-Dimethylimidazol-5-yl)-2-[4-(N-ethyl-sulphamoyl)anilino]pyrimidine | 0.97 (t, 3H), 2.38 (s, 3H), 2.77 (m, 2H), 3.96 (s, 3H), 7.2 (d, 1H), 7.3 (t, 1H), 7.63 (s, 1H), 7.68 (s, 2H), 7.92 (d, 2H), 8.43 (d, 1H), 9.93 (s, 1H) | 371 (M-H)⁻ | Ex 5 |
| 91 | 4-(1,2-Dimethylimidazol-5-yl)-2-{4-[N-(2-hydroxyethyl)sulphamoyl]anilino}pyrimidine | 2.37 (s, 3H), 2.77 (t, 2H), 3.33 (m, 2H), 3.93 (s, 3H), 4.62 (t, 1H), 7.18 (d, 1H), 7.3 (s, 1H), 7.63 (s, 1H), 7.7 (d, 2H), 7.9 (d, 2H), 8.43 (d, 1H), 9.93 (s, 1H) | 387 (M-H)⁻ | Ex 5 |
| 92 | 4-(1,2-Dimethylimidazol-5-yl)-2-(4-{N-[2-(2-hydroxyethoxy)ethyl]sulphamoyl}anilino)pyrimidine | 2.37 (s, 3H), 2.9 (m, 2H), 2.33 (m, 4H), 3.43 (m, 2H), 3.96 (s, 3H), 4.5 (t, 1H), 7.2 (d, 1H), 7.42 (t, 1H), 7.63 (s, 1H), 7.7 (d, 2H), 7.92 (d, 2H), 8.43 (d, 1H), 9.93 (s, 1H) | 431 (M-H)⁻ | Ex 5 |
| 93 | 4-(1,2-Dimethylimidazol-5-yl)-2-{4-[N-(pyrid-2-ylmethyl)sulphamoyl]anilino}pyrimidine | 2.4 (s, 3H), 3.95 (s, 3H), 4.07 (s, 2H), 7.2 (m, 2H), 7.35 (d, 1H), 7.63 (s 1H), 7.7 (m, 3H), 7.88 (d, 2H), 8.0 (s, 1H), 8.43 (m, 2H), 9.93 (s, 1H) | 434 (M-H)⁻ | Ex 5 |
| 94 | 4-(1,2-Dimethylimiciazol-5-yl)-2-{4-[N-(pyrid-3-ylmethyl)suilphamoyl]anilino}pyrimidine | 2.4 (s, 3H), 3.96 (s, 3H), 4.02 (d, 2H), 7.2 (d, 1H), 7.27 (m, 1H), 7.63 (m, 2H), 7.7 (d, 2H), 7.9 (d, 2H), 8.03 (t, 1H), 8.4 (m, 3H), 9.93 (s, 1H) | 434 (M-H)⁻ | Ex 5 |
| 95 | 4-(1,2-Dimethylimidazol-5-yl)-2-{4-(N-pentyl-sulphamoyl)anilino]pyrimidine | 0.8 (t, 3H), 1.2 (m, 4H), 1.35 (m, 2H), 2.38 (s, 3H), 2.7 (m, 2H), 3.95 (s, 3H), 7.2 (d, 1H), 7.3 (t, 1H), 7.63 (s, 1H), 7.67 (d, 2H), 7.92 (d, 2H), 8.43 (d, 1H), 9.93 (s, 1H) | 413 (M-H)⁻ | Ex 5 |
| 96 | 4-(1,2-Dimethylimidazol-5-yl)-2-{4-[N-(5-hydroxy-pentyl)sulphamoyl]anilino}pyrimidine | 1.27 (m, 6H), 2.36 (s, 3H), 2.7 (m, 2H), 3.27 (m, 2H), 3.96 (s, 3H), 4.27 (t, 1H), 7.2 (d, 1H), 7.3 (t, 1H), 7.63 (s, 1H), 7.67 (d, 2H), 7.9 (d, 2H), 8.43 (d, 1H), 9.92 (s, 1H) | 429 (M-H)⁻ | Ex 5 |
| 97 | 4-(1,2-Dimethylimidazol-5-yl)-2-{4-[N-(3-ethoxypropyl)sulphamoyl]anilino}pyrimidine | 1.03 (t, 3H), 1.57 (m, 2H), 2.37 (s, 3H), 2.77 (m, 2H), 3.27 (m, 4H), 3.95 (s, 3H), 7.2 (d, 1H), 7.33 (t, 1H), 7.63 (s, 1H), 7.67 (d, 2H), 7.93 (d, 2H), 8.43 (d, 1H), 9.93 (s, 1H) | 429 (M-H)⁻ | Ex 5 |
| 98 | 4-(1,2-Dimethylimidazol-5-yl)-2-(4-[N-(2-hydroxy-propyl)sulphamoyl]anilino}pyrimidine | 1.02 (d, 3H), 2.4 (s, 3H), 2.65 (m, 2H), 3.57 (m, 1H), 3.98 (s, 3H), 4.63 (d, 1H), 7.22 (d, 1H), 7.32 (t, 1H), 7.67 (s, 1H), 7.7 (d, 2H), 7.92 (d, 2H), 8.43 (d, 1H), 9.92 (s, 1H) | 401 (M-H)⁻ | Ex 5 |
| 99 | 4-(1,2-Dimethylimidazol-5-yl)-2-{4-[N-(3-isopropoxypropyl)sulphamoyl]anilino}pyrimidine | 1.0 (d, 6H), 1.55 (m, 2H), 2.38 (s, 3H), 2.76 (m, 2H), 3.27 (m, 2H), 3.4 (m, 1H), 3.95 (s, 3H), 7.18 (d, 1H), 7.3 (t, 1H), 7.63 (s, 1H), 7.68 (d, 2H), 7.92 (d, 2H), 8.43 (d, 1H), 9.93 (s, 1H) | 443 (M-H)⁻ | Ex 5 |
| 100 | 4-(1,2-Dimethylimidazol-5-yl)-2-{4-[N-(2-hydroxybutyl)sulphamoyl]anilino}pyrimidine | 0.8 (t, 3H), 1.22 (m, 1H), 1.4 (m, 1H), 2.37 (s, 3H), 2.65 (m, 2H), 3.27 (m, 1H), 3.95 (s, 3H), 4.55 (d, 1H), 7.2 (d, 1H), 7.25 (t, 1H), 7.63 (s, 1H), 7.7 (d, 2H), 7.92 (d, 2H), 8.43 (d, 1H), 9.92 (s, 1H) | 415 (M-H)⁻ | Ex 5 |
| 101 | 4-(1,2-Dimethylimidazol-5-yl)-2-{4-[N-(2-pyrid-2-ylethyl)sulphamoyl]anilino}pyrimidine | 2.38 (s, 3H), 2.83 (t, 2H), 3.07 (m, 2H), 3.95 (s, 3H), 7.18 (m, 3H), 7.47 (t, 1H), 7.63 (s 1H), 7.67 (m, 3H), 7.9 (d, 2H), 8.42 (d, 2H), 9.93 (s, 1H) | 448 (M-H)⁻ | Ex 5 |
| 102 | 4-(1,2-Dimethylimidazol-5-yl)-2-{4-[N-(2-pyrid-4-ylethyl)sulphamoyl]anilino}pyrimidine | 2.37 (s, 3H), 2.7 (t, 2H), 3.0 (m, 2H), 3.95 (s, 3H), 7.17 (m, 3H), 7.5 (t, 1H), 7.63 (s 1H), 7.67 (d, 2H), 7.9 (d, 2H), 8.42 (m, 3H), 9.93 (s, 1H) | 448 (M-H)⁻ | Ex 5 |
| 103 | 4-(1-Methyl-2-ethyl-imidazol-5-yl)-2-[4-(N-cyclopropylsulphamoyl)anilino]pyrimidine | 0.30 (m, 2H), 0.44 (m, 2H), 1.23 (t, 3H), 2.06 (m, 1H), 2.73 (q, 2H), 3.95 (s, 3H), 7.20 (d, 1H), 7.69 (m, 4H), 7.90 (d, 2H), 8.43 (d, 1H), 9.80 (s, 1H) | 399 | Ex 29 |
| 104¹ | 4-[1-(2,2,2-Trifluoroethyl)-2-methyl-imidazol-5-yl]-2-{4-[N- | 0.02 (m, 2H), 0.30 (m, 2H), 0.78 (m, 1H), | 467 | Ex 30 |

-continued

| Ex | Compound | NMR | m/z | SM |
|---|---|---|---|---|
|  | (cyclopropylmethyl)sulphamoyl]anilino}pyrimidine | 2.40 (s, 3H), 2.59 (t, 2H), 5.76 (q, 2H), 7.21 (d, 1H), 7.46 (t, 1H), 7.65 (d, 2H), 7.73 (s, 1H), 7.81 (d, 2H), 8.42 (d, 1H), 9.93 (s, 1H) |  |  |
| 105[1] | 4-[1-(2,2,2-Trifluoroethyl)-2-methyl-imidazol-5-yl]-2-{4-[N-(2-methoxyethyl)sulphamoyl]anilino}pyrimidine | 2.50 (s, 3H), 3.13 (m, 2H), 3.29 (s, 3H), 3.41 (T, 2H), 5.05 (brs, 1H), 5.38 (q, 2H), 7.03 (d, 1H), 7.48 (s, 1H), 7.57 (s, 1H), 7.70 (d, 2H), 7.81 (d, 2H), 8.41 (d, 1H) | 471 | Ex 30 |
| 106[1] | 4-[1-(2,2,2-Trifluoroethyl)-2-methyl-imidazol-5-yl]-2-(4-(N-cyclopropylsulphamoyl)anilino)pyrimidine | 0.30 (m, 2H), 0.47 (m, 2H), 2.03 (m, 1H), 2.40 (s, 3H), 5.77 (q, 2H), 7.20 (d, 1H), 7.73 (m, 4H), 7.81 (d, 2H), 8.42 (d, 1H), 9.96 (s, 1H) | 453 | Ex 30 |
| 107[5] | 4-(1-Isopropyl-2-methylimidazol-5-yl)-2-{4-[N-(2-methoxyethyl)sulphamoyl]anilino}pyrimidine | 1.48 (d, 6H), 2.51 (s, 3H), 2.86 (m, 2H), 3.16 (s, 3H), 3.29 (t, 2H), 5.66 (sept, 1H), 7.14 (d, 1H), 7.46 (s, 1H), 7.49 (t, 1H), 7.69 (d, 2H), 7.89 (d, 2H), 8.45 (d, 1H), 9.88 (s, 1H) | 431 | Ex 32 |
| 108[3] | 4-(1,2,4-Trimethyl-imidazol-5-yl)-2-{4-[N-(2-methoxyethyl)sulphamoyl]anilino}pyrimidine | 2.28 (s, 3H), 2.35 (s, 3H), 2.90 (q, 2H), 3.18 (s, 3H), 3.75 (s, 3H), 6.98 (d, 1H), 7.44 (t, 1H), 7.70 (d, 2H), 7.95 (d, 2H), 8,52 (d, 1H), 9.95 (s, 1H) | 416 | Ex 31 |
| 109 | 5-Bromo-4-(1,2-dimethyllinidazol-5-yl)-2-(4-sulphamoylanilino)pyrimidine | 2.44 (s, 3H), 3.75 (s, 3H), 7.15 (s, 2H), 7.65 (s, 1H), 7.75 (d, 2H), 7.85 (d, 2H), 8.70 (s, 1H), 10.15 (s, 1H) | 424 | Ex 63 |
| 110 | 5-Bromo-4-(1,2-dimethylimidazol-5-yl)-2-[4-(N-propylsulphamoyl)anilino]pyrimidine | 0.78 (t, 3H), 1.39 (q, 2H), 2.41 (s, 3H), 2.68 (q, 2H), 3.75 (s, 3H), 7.35 (t, 1H), 7.64 (s, 1H), 7.70 (d, 2H), 7.88 (d, 2H), 8.70 (s, 1H) | 466 | Ex 63 |
| 111[4] | 5-Bromo-4-(1,2-dimethylimidazol-5-yl)-2-{4-[N-(3-methoxypropyl)sulphamoyl]anilino}pyrimidine | 1.58 (q, 2H), 2.40 (s, 3H), 2.76 (q, 2H), 3.14 (s, 3H), 3.28 (m, 2H), 3.73 (s, 3H), 7.36 (t, 1H), 7.64 (s, 1H), 7.71 (d, 2H), 7.87 (d, 2H), 8.70 (s, 1H) | 498 | Ex 63 |
| 112[4] | 5-Bromo-4-(1,2-dimethylimidazol-5-yl)-2-[4-(N-methylsulphamoyl)anilino]pyrimidine | 2.38 (s, 6H), 3.75 (s, 3H), 7.10 (m, 1H), 7.62 (s, 1H), 7.70 (d, 2H), 7.87 (d, 2H), 8.70 (s, 1H) | 438 | Ex 63 |
| 113[4] | 5-Bromo-4-(1,2-dimethylimidazol-5-yl)-2-{4-[N-(cyclopropylmethyl)sulphamoyl]anilino}pyrimidine | 0.05 (q, 2H), 0.31 (q, 2H), 0.78 (m, 1H), 2.39 (s, 3H), 2.60 (t, 2H), 3.72 (s, 3H), 7.45 (t, 1H), 7.60 (s, 1H), 7.70 (d, 2H), 7.82 (d, 2H), 8.70 (s, 1H) | 476 | Ex 63 |
| 114[3] | 4-(1,2,4-Trimethyl-imidazol-5-yl)-2-(4-sulphamoylanilino)pyrimidine | 2.26 (s, 3H), 2.34 (s, 3H), 3.76 (s, 3H), 6.95 (s, 1H), 7.14 (s, 2H), 7.72 (d, 2H), 7.90 (s, 2H), 8.50 (s, 1H), 9.90 (s, 1H) | 358 | Ex 31 |
| 115[3] | 4-(1,2,4-Trimethyl-imidazol-5-yl)-2-[4-(N-methylsulphamoyl)anilino]pyrimidine | 2.23 (s, 3H), 2.32 (s, 3H), 2.38 (d, 3H), 3.75 (s, 3H), 6.98 (s, 1H), 7.18 (m, 1H), 7.67 (d, 2H) 7.95 (d, 2H), 8.50 (d, 1H), 9.98 (s, 1H) | 372 | Ex 31 |
| 116[5] | 4-(1,2,4-Trimethyl-imidazol-5-yl)-2-{4-[N-(3-N,N-dimethylamino-propyl)sulphamoyl]anilino}pyrimidine | 1.45 (q, 2H), 2.05 (s, 3H), 2.12 (t, 2H), 2.15 (s, 3H), 2.35 (s, 3H), 2.75 (q, 2H), 3.72 (s, 3H), 6.95 (d, 1H), 7.32 (t, 1H), 7.68 (d, 2H), 7.93 (d, 2H), 8.50 (d, 1H), 9.95 (s, 1H) | 444 | Ex 31 |
| 117[3] | 4-(1,2,4-Trimethyl-imidazol-5-yl)-2-[4-(N-t-butylsulphamoyl)anilino]pyrimidine | 1.08 (s, 9H), 2.27 (s, 3H), 2.34 (s, 3H), 3.72 (s, 3H), 6.95 (d, 1H), 7.25 (s, 1H), 7.70 (d, 2H), 7.90 (d, 2H), 8.50 (d, 1H), 9.90 (s, 1H) | 414 | Ex 31 |
| 118[3] | 4-(1,2,4-Trimethyl-imidazol-5-yl)-2-{4-[N-(1,1-dimethylpropyl)sulphamoyl]anilino}pyrimidine | 0.71 (t, 3H), 1.01 (s, 3H), 1.21 (q, 2H), 2.30 (s, 3H), 2.40 (s, 3H), 3.77 (s, 3H), 7.0 (d, 1H), 7.14 (s, 1H), 7.70 (d, 2H), 7.89 (d, 2H), 8.58 (d, 1H), 9.98 (s, 1H) | 428 | Ex 31 |
| 119[3] | 4-(1,2,4-Trimethyl-imidazol-5-yl)-2-[4-(N-cyclopropylsulphamoyl)anilino]pyrimidine | 0.04 (m, 2H), 0.15 (m, 2H), 1.78 (m, 1H), 3.40 (s, 3H), 6.64 (d, 2H), 7.32 (s, 1H), 7.38 (d, 2H), 7.62 (d, 2H), 8.20 (d, 1H), 9.63 (s, 1H) | 398 | Ex 31 |
| 120 | 4-(1,2-Dimethylimidazol-5-yl)-2-[4-(N-propylsulphamoyl)anilino]pyrimidine | 0.75–0.80 (t, 3H), 1.29–1.41 (m, 2H), 2.37 (s, 3H), 2.64–2.70 (q, 2H), 3.95 (s, 3H), 7.18 (d, 1H), 7.32 (t, 1H), 7.62 (s, 1H), 7.68 (d, 2H), | 387 | Ex 5 |

| Ex | Compound | NMR | m/z | SM |
|---|---|---|---|---|
| | | 7.90 (d, 2H), 8.42 (d, 1H), 9.89 (s, 1H) | | |
| 121 | 4-(1,2-Dimethylimidazol-5-yl)-2-[4-(N-cyclopropylsulphamoyl)anilino]pyrimidine | 0.00–0.06 (m, 2H), 0.08–0.17 (m, 2H), 1.74–1.80 (m, 1H), 2.05 (s, 3H), (m, 3.63 (s, 3H), 6.87 (d, 1H), 7.31 (s, 1H), 7.33 (brs, 1H), 7.38 (d, 2H), 7.61 (d, 2H), 8.11 (d, 1H), 9.60 (s, 1H) | 385 | Ex 5 |
| 122 | 4-(1,2-Dimethylimidazol-5-yl)-2-[4-(N-cyclobutylsulphamoyl)anilino]pyrimidine | 1.4–1.50 (m, 2H), 1.65–1.78 (m, 2H), 1.84–1.93 (m, 2H), 2.37 (s, 3H), 3.52–3.66 (m, 1H), 3.94 (s, 3H), 7.19 (d, 1H), 7.63–7.71 (m, 4H), 7.89 (d, 2H), 8.43 (d, 1H), 9.89 (s, 1H) | 399 | Ex 5 |
| 123 | 4-(1,2-Dimethylimidazol-5-yl)-2-{4-[N-(2,2,2-trifluoroethyl)sulphamoyl]anilino}pyrimidine | 2.38 (s, 3H), 3.63 (q, 2H), 3.95 (s, 3H), 7.20 (d, 1H), 7.63 (s, 1H), 7.73 (d, 2H), 7.93 (d, 2H), 8.35 (brs, 1H), 8.43 (d, 1H), 9.94 (s, 1H) | 427 | Ex 5 |
| 124 | 4-(1,2-Dimethylimidazol-5-yl)-2-{4-[N-(3-trifluoromethylphenyl)sulphamoyl]anilino}pyrimidine | 2.36 (s, 3H), 3.89 (s, 3H), 7.19 (d, 1H), 7.32–7.37 (m, 3H), 7.44 (d, 1H), 7.62 (s, 1H), 7.69 (d, 2H), 7.87 (d, 2H), 8.40 (d, 1H), 9.93 (s, 1H), 10.50 (brs, 1H) | 489 | Ex 5 |
| 125 | 4-(1-Ethyl-2-methylimidazol-5-yl)-2-[4-(N-methylsulphamoyl)anilino]pyrimidine | 9.81 (s, 1H), 8.43 (d, 1H), 7.91 (d, 2H), 7.75–7.65 (m, 3H), 7.27–7.18 (m, 2H), 4.60 (q, 2H), 2.42–2.37 (m, 6H), 1.19 (t, 3H) | 373 | Ex 28 |

[1]Purified by flash chromatography eluting with DCM/2% methanolic ammonia (100:0 increasing in polarity to 95:5).
[2]Purified by passing through an Isolute amine column.
[3]Purified by flash chromatography eluting with DCM/MeOH (100:0 increasing in polarity to 95:5).
[4]Purified by flash chromatography eluting with DCM/MeOH (100:0 increasing in polarity to 98:2).
[5]Product isolated by aqueous work-up and extraction with EtOAc. Extracts washed with 1 M aqueous acetic acid and aqueous sodium bicarbonate solution.

Example 126

4-(1-Ethyl-2-methylimidazol-5-yl)-2-(4-{N-[2-(2-hydroxyethoxy)ethyl]sulphamoyl}anilino)pyrimidine Chlorosulphonic acid (150 μl, 2.16 mmol) was added dropwise to a solution of 2-anilino-4-(1-ethyl-2-methylimidazol-5-yl)pyrimidine (Example 28; 150 mg, 0.54 mmol) in thionyl chloride (3 ml) cooled to 0° C. and the mixture stirred for 10 minutes at 0° C. then heated at 90° C. for 90 minutes. The volatiles were removed by evaporation and the resultant solid placed under high vacuum (<2 mmHg) for 1 hr. The resulting solid was placed under nitrogen and a solution of 2-(2-aminoethyl)ethanol (114 mg, 1.00 mmol) and diethylmethylamine in MeOH (3 ml) was cautiously added. The solution was stirred for 30 minutes and the volatiles were evaporated. Water (20 ml) was added and the precipitated solid was collected by filtration and washed with water (2×10 ml). The residue was dissolved in MeOH (5 ml) and loaded on to an Isolute amine column, eluted with MeOH (30 ml) and the fractions containing product were evaporated to give the title compound (190 mg, 79%) as a beige solid. NMR 1.18 (t, 3H), 2.39 (s, 3H), 2.89 (t, 2H), 3.15 (m, 7H), 4.38 (q, 2H), 7.21 (d, 1H), 7.71 (m, 3H), 7.89 (d, 2H), 8.41 (d, 1H), 9.82 (s, 1H); m/z 447.

Examples 127–144

The following compounds were synthesised in an analogous method to Example 126.

| Ex | Compound | NMR | m/z | SM |
|---|---|---|---|---|
| 127 | 4-(1-Ethyl-2-methylimidazol-5-yl)-2-{4-[N-(3-isopropoxy-2-hydroxypropyl)sulphamoyl]anilino}pyrimidine | 1.01 (d, 6H), 1.20 (t, 3H), 2.40 (s, 3H), 2.62 (m, 1H), 2.81 (m, 1H), 3.23 (d, 2H), 3.50 (m, 2H), 4.48 (q, 2H), 4.76 (s, 1H), 7.20 (d, 1H), 7.70 (m, 3H), 7.84 (d, 2H), 8.40 (d, 1H), 9.81 (s, 1H) | 475 | Ex 28 |
| 128 | 4-(1-Ethyl-2-methylimidazol-5-yl)-2-{4-[N-(2-isoxazol-3-yloxyethyl)sulphamoyl]anilino}pyrimidine | 1.19 (t, 3H), 2.40 (s, 3H), 3.13 (t, 2H), 4.17 (t, 2H), 4.54 (q, 2H), 6.12 (d, 1H), 7.20 (d, 1H), 7.70 (m, 4H), 7.86 (d, 2H), 8.40 (d, 1H), 8.60 (d, 1H), 9.80 (s, 1H) | 470 | Meth 85, Ex 28 |
| 129[1] | 4-(1-Ethyl-2-methylimidazol-5-yl)-2-{4-[N-(2-isothiazol-3-yloxyethyl)sulphamoyl]anilino}pyrimidine | 1.19 (t, 3H), 2.39 (s, 3H), 3.13 (q, 2H), 4.26 (t, 2H), 4.55 (q, 2H), 6.67 (d, 1H), 7.20 (d, 1H), 7.70 (m, 4H), 7.84 (d, 2H), 8.40 (d, 1H), 8.81 (d, 1H), 9.80 (s, 1H) | 486 | Meth 86, Ex 28 |
| 130 | 4-(1-Ethyl-2-methylimidazol-5-yl)-2-(4-{N-[2-(1,2,5-thiadiazol-3-yloxy)ethyl]sulphamoyl}anilino)pyrimidine | 1.19 (t, 3H), 2.39 (s, 3H), 3.18 (q, 2H), 4.34 (t, 2H), 4.56 (q, 2H), 7.20 (d, 1H), 7.70 (m, 4H), 7.86 (d, 2H), 8.25 (s, 1H), 8.40 (d, 1H), 9.80 (s, 1H) | 487 | Meth 87, Ex 28 |
| 131[1] | 4-(1-Ethyl-2-methylimidazol-5-yl)-2-{4-[N-(3-isoxazol-3-yloxypropyl)sulphamoyl]anilino}pyrimidine | 1.18 (t, 3H), 1.80 (m, 2H), 2.38 (s, 3H), 2.84 (q, 2H), 4.16 (t, 2H), 4.56 (q, 2H), 6.25 (s, | 484 | Meth 88, Ex 28 |

-continued

| Ex | Compound | NMR | m/z | SM |
|---|---|---|---|---|
|  |  | 1H), 7.20 (d, 1H), 7.49 (t, 1H), 7.68 (m, 3H), 7.87 (d, 2H), 8.40 (d, 1H), 8.59 (s, 1H), 9.80 (s, 1H) |  |  |
| 132[1] | 4-(1-Ethyl-2-methylimidazol-5-yl)-2-{4-[N-(3-isothiazol-3-yloxypropyl)sulphamoyl]anilino}pyrimidine | 1.18 (t, 3H), 1.80 (m, 2H), 2.38 (s, 3H), 2.84 (q, 2H), 4.26 (t, 2H), 4.56 (q, 2H), 6.69 (d, 1H), 7.20 (d, 1H), 7.45 (t, 1H), 7.68 (m, 3H), 7.87 (d, 2H), 8.40 (d, 1H), 8.80 (d, 1H), 9.80 (s, 1H) | 500 | Meth 89, Ex 28 |
| 133[1] | 4-(1-Ethyl-2-methylimidazol-5-yl)-2-(4-{N-[3-(1,2,5-thiadiazol-3-yloxy)propyl]sulphamoyl}anilino)pyrimidine | 1.18 (t, 3H), 1.85 (m, 2H), 2.38 (s, 3H), 2.91 (q, 2H), 4.36 (t, 2H), 4.56 (q, 2H), 7.20 (d, 1H), 7.45 (t, 1H), 7.68 (m, 3H), 7.87 (d, 2H), 8.30 (s, 1H), 8.40 (d, 1H), 9.80 (s, 1H) | 501 | Meth 90, Ex 28 |
| 134 | 4-(1-Methyl-2-ethylimidazol-5-yl)-2-[4-(N-cyclobutyl-sulphamoyl)anilino]pyrimidine | 1.23 (t, 3H), 1.45 (m, 2H), 1.70 (m, 2H), 1.87 (m, 2H), 2.93 (q, 2H), 3.58 (m, 1H), 3.95 (s, 3H), 7.20 (d, 1H), 7.69 (m, 4H), 7.90 (d, 2H), 8.43 (d, 1H), 9.86 (s, 1H) | 413 | Ex 29 |
| 135[1] | 4-[1-(2,2,2-Trifluoroethyl)-2-methylimidazol-5-yl]-2-[4-(N-cyclobutylsulphamoyl)anilino]pyrimidine | 1.45 (m, 2H), 1.70 (m, 2H), 1.87 (m, 2H), 2.40 (s, 3H), 3.58 (m, 1H), 5.80 (q, 2H), 7.23 (d, 1H), 7.69 (m, 4H), 7.90 (d, 2H), 8.44 (d, 1H), 9.96 (s, 1H) | 467 | Ex 30 |
| 136[2] | 4-(1-Isopropyl-2-methylimidazol-5-yl)-2-[4-(N-cyclobutylsulphamoyl)anilino]pyrimidine | 1.45 (m, 8H), 1.72 (m, 2H), 1.88 (m, 2H), 3.30 (s, 3H), 3.60 (m, 1H), 5.60 (sept, 1H), 7.16 (d, 1H), 7.48 (s, 1H), 7.68 (d, 2H), 7.74 (d, 1H), 7.88 (d, 2H), 8.48 (d, 1H), 9.90 (s, 1H) | 427 | Ex 32 |
| 137[3] | 4-(1-Isopropyl-2-methylimidazol-5-yl)-2-[4-[N-cyclopropylsulphamoyl)anilino]pyrimidine | 0.40 (m, 2H), 0.50 (m, 2H), 1.50 (d, 6H), 2.12 (m, 1H), 2.52 (s, 3H), 5.70 (m, 1H), 7.17 (d, 1H), 7.48 (s, 1H), 7.71 (s, 1H), 7.75 (d, 2H), 7.93 (d, 2H), 8.49 (d, 1H), 9.93 (s, 1H) | 413 | Ex 32 |
| 138[4] | 4-(1-Isopropyl-2-methylimidaxol-5-yl)-2-{4-[N-(cyclopropylmethyl)sulphamoyl]anilino}pyrimidine | 0.09 (m, 2H), 0.36 (m, 2H), 0.81 (m, 1H), 1.49 (d, 6H), 2.60 (s, 3H), 2.65 (t, 2H), 5.70 (m, 1H), 7.17 (d, 1H), 7.48 (s, 1H), 7.53 (t, 1H), 7.72 (d, 2H), 7.90 (d, 2H), 8.48 (d, 1H), 9.90 (s, 1H) | 427 | Ex 32 |
| 139[4] | 4-(1-Isopropyl-2-methylimidazol-5-yl)-2-{4-[N-(cyanomethyl)sulphamoyl]anilino}pyrimidine | 1.46 (d, 6H), 2.48 (s, 3H), 4.04 (d, 2H), 5.66 (sept, 1H), 7.15 (d, 1H), 7.46 (s, 1H), 7.71 (d, 2H), 7.92 (d, 2H), 8.32 (t, 1H), 8.48 (d, 1H), 9.95 (s, 1H) | 412 | Ex 32 |
| 140[6] | 4-(1-Isopropyl-2-methylimidazol-5-yl)-2-{4-[N-(pyrid-2-ylmethyl)sulphamoyl]anilino}pyrimidine | 1.46 (d, 6H), 3.29 (s, 3H), 4.05 (b d, 2H), 5.67 (sept, 1H), 7.13 (d, 1H), 7.21 (m, 1H), 7.36 (d, 1H), 7.43 (s, 1H), 7.69 (m, 3H), 7.86 (d, 2H), 8.02 (b t, 1H), 8.42 (d, 1H), 8.46 (d, 1H), 9.88 (s, 1H) | 464 | Ex 32 |
| 141 | 4-(1-Ethyl-2-methylimidazol-5-yl)-2-{4-[N-(5-methylpyrazin-2-ylmethyl)sulphamoyl]anilino}pyrimidine | 1.20 (t, 3H), 2.40 (s, 6H), 4.11 (s, 2H), 4.60 (q, 2H), 7.24 (d, 1H), 7.68 (m, 3H), 7.85 (d, 2H), 8.10 (s, 1H), 8.36 (s, 1H), 8.42 (s, 1H) 8.45 (d, 1H), 9.82 (s, 1H) | 465 | Ex 28 |
| 142 | 4-(1-Methyl-2-methoxymethylimidazol-5-yl)-2-{4-[N-(2-methoxyethyl)sulphamoyl]anilino}pyrimidine | 2.88 (t, 2H), 3.17 (s, 3H), 3.30 (m, 5H), 4.05 (s, 3H), 4.55 (s, 2H), 7.28 (d, 1H), 7.49 (t, 1H), 7.74 (d, 3H), 7.92 (d, 2H), 8.50 (d, 1H), 9.98 (s, 1H) | 433 | Ex 33 |
| 143 | 4-(1,2-Dimethylimidazol-5-yl)-2-{4-[N-(3-isothiazol-3-yloxypropyl)sulphamoyl]anilino}pyrimidine | 1.81 (m, 2H), 2.36 (s, 3H), 2.87 (q, 2H), 3.96 (s, 3H), 4.13 (t, 2H), 6.68 (d, 1H), 7.20 (d, 1H), 7.43 (t, 1H), 7.62 (s, 1H), 7.68 (d, 2H), 7.89 (d, 2H), 8.42 (d, 1H), 8.80 (d, 1H), 9.89 (s, 1H) | 486 | Ex 5, Meth 89 |

-continued

| Ex | Compound | NMR | m/z | SM |
|---|---|---|---|---|
| 144 | 4-(1-Ethyl-2-methylimidazol-5-yl)-2-{4-[N-(2-propynyl)sulphamoyl]anilino}pyrimidine | 1.20 (t, 3H), 2.40 (s, 3H), 3.05 (s, 1H), 3.65 (s, 2H), 4.60 (q, 2H), 7.21 (d, 1H), 7.68 (s, 1H), 7.71 (d, 2H), 7.90 (d, 3H), 8.45 (d, 1H), 9.85 (s, 1H); m/z 397 | 399 | Ex 28 |

[1]Purified by flash chromatography eluting with DCM/2% methanolic ammonia (100:0 increasing in polarity to 95:5).
[2]Reacted with 4 equivalents of cyclobutylamine/12 equivalents of dimethylethylamine. Purified by flash chromatography eluting with DCM/MeOH (98:2 increasing in polarity to 95:5).
[3]Reacted with 4 equivalents of cyclopropylamine/12 equivalents of dimethylethylamine. Purified by flash chromatography eluting with DCM/MeOH (98:2 increasing in polarity to 94:6).
[4]Reacted with 4 equivalents of cyclopropylmethylamine/12 equivalents of dimethylethylamine. Purified by flash chromatography eluting with DCM/MeOH (98:2 increasing in polarity to 94:6).
[5]Reacted with 5.75 equivalents of aminoacetonitrile/9 equivalents of dimethylethylamine. Product extracted from aqueous sodium bicarbonate solution with DCM.
[6]Reacted with 4 equivalents of 2-aminomethylpyridine/9 equivalents of dimethylethylamine. Purified by flash chromatography eluting with DCM/MeOH (98:2 increasing in polarity to 90:10).

Example 145

5-Bromo-4-(1,2-dimethylimidazol-5-yl)-2-{4-[N-(2-methoxyethyl)sulphamoyl]anilino}pyrimidine Bromine (8 μl, 0.14 mmol) was added to a solution of 4-(1,2-dimethylimidazol-5-yl)-2-{4-[N-(2-methoxyethyl)sulphamoyl]anilino}pyrimidine (Example 35; 52 mg, 0.13 mmol) in glacial acetic acid (2 ml) heated at 60° C. The mixture was heated at 60° C. for 4 hours, then the solvent was removed by evaporated. The residue was dissolved in DCM (20 ml), washed with saturated aqueous sodium hydrogen carbonate solution (20 ml), dried (Chemelut column 1005) and purified by flash chromatography eluting with DCM/2% methanolic ammonia (100:0 increasing in polarity to 97:3) to yield the title compound (37 mg, 60%) as a white foam NMR 2.40 (s, 3H), 3.06 (q, 2H), 3.20 (s, 3H), 3.36 (t, 2H), 3.68 (s, 3H), 5.00 (t, 1H), 7.56 (s, 1H), 7.67 (d, 2H), 7.73 (d, 2H), 7.80 (s, 1H), 8.53 (s, 1H); m/z 483.

Examples 146–148

The following compounds were synthesised in an analogous method to Example 145.

| Ex | Compound | NMR | m/z | SM |
|---|---|---|---|---|
| 146 | 5-Bromo-4-(l-ethyl-2-methylimidazol-5-yl)-2-{4-[N-(2-methoxyethyl)sulphamoyl]anilino}pyrimidine | 1.25 (t, 3H), 2.50 (s, 3H), 3.15 (q, 2H), 3.26 (s, 3H), 3.42 (t, 2H), 4.33 (q, 2H), 4.92 (t, 1H), 7.40 (s, 1H), 7.71 (d, 2H), 7.82 (m, 3H), 8.61 (s, 1H) | 497 | Ex 37 |
| 147[1] | 5-Bromo-4-[1-(2-methoxyethyl)-2-methylimidazol-5-yl]-2-{4-[N-(2-methoxyethyl)sulphamoyl]anilino}pyrimidine | 2.42 (s, 3H), 2.89 (m, 2H), 3.02 (s, 3H), 3.16 (s, 3H), 3.29 (m, 2H), 3.36 (t, 2H), 4.51 (t, 2H), 7.49 (t, 1H), 7.58 (s, 1H), 7.72 (d, 2H), 7.85 (d, 2H), 8.74 (s, 1H), 10.15 (s, 1H) | 525 | Ex 61 |
| 148[2] | 5-Bromo-4-[1-(2-methoxyethyl)-2-methylimidazol-5-yl]-2-{4-[N-(3-methoxypropyl)sulphamoyl]anilino}pyrimidine | 1.59 (quin, 2H), 2.44 (s, 3H), 2.78 (q, 2H), 3.05 (s, 3H), 3.17 (s, 3H), 3.28 (t, 2H), 3.39 (t, 2H), 4.55 (t, 2H), 7.39 (t, 1H), 7.61 (s, 1H), 7.73 (d, 2H), 7.88 (d, 2H), 8.77 (s, 1H), 10.19 (s, 1H) | 539 | Ex 82 |

[1]Extracted into EtOAc. Purified by column chromatography eluting with DCM/MeOH (96:4 increasing in polarity to 90:10).
[2]Extracted into EtOAc. Purified by column chromatography eluting with DCM/2% methanolic ammonia (98:2 increasing in polarity to 94:6).

Example 149

5-Chloro-4-(1-ethyl-2-methylimidazol-5-yl)-2-{4-[N-(2-methoxyethyl)sulphamoyl]anilino}pyrimidine N-Chlorosuccinimide (80 mg, 0.6 mmol) was added to a solution of 4-(1-ethyl-2-methylimidazol-5-yl)-2-{[N-(2-methoxyethyl)sulphamoyl]anilino}pyrimidine (Example 37; 208 mg, 0.5 mmol) in glacial acetic acid (5 ml) and the mixture heated at 60° C. for 3 hours. The solvent was evaporated and the residue dissolved in DCM (30 ml), washed with saturated aqueous sodium hydrogen carbonate solution (20 ml), the aqueous layer was extracted with DCM (20 ml). The DCM extracts were combined, dried (Chemelut column 1005) and the solvent evaporated. The residue was purified by flash chromatography on silica gel eluting with DCM/2% methanolic ammonia (100:0 increasing in polarity to 97:3) to give the title compound (110 mg, 44%) as a white foam. NMR 1.24 (t, 3H), 2.45 (s, 3H), 3.09 (q, 2H), 3.28 (s, 3H), 3.40 (t, 2H), 4.32 (t, 2H), 4.92 (t, 1H), 7.40 (s, 1H), 7.72 (d, 2H), 7.83 (d, 2H), 7.88 (s, 1H), 8.49 (s, 1H); m/z 451.

Examples 150–153

The following compounds were synthesised in an analogous method to Example 149.

| Ex | Compound | NMR | m/z | SM |
|---|---|---|---|---|
| 150 | 5-Chloro-4-(1,2-dimethylimidazol-5-yl)-2-{4-[N-(2-methoxyethyl)sulphamoyl]anilino}pyrimidine | 2.50 (s, 3H), 3.15 (q, 2H), 3.26 (s, 3H), 3.42 (t, 2H), 3.78 (s, 3H), 4.92 (t, 1H), 7.43 (s, 1H), | 437 | Ex 35 |

-continued

| Ex | Compound | NMR | m/z | SM |
|---|---|---|---|---|
| | | 7.71 (d, 2H), 8.01 (d, 3H), 8.07 (s, 1H), 8.61 (s, 1H) | | |
| 151[1] | 5-Chloro-4-(1-ethyl-2-methylimidazol-5-yl)-2-{4-[N-(tetrahydrofur-2-ylmethyl)sulphamoyl]anilino}pyrimidine | 1.24 (t, 3H), 1.50 (m, 1H), 1.84 (m, 3H), 2.48 (s, 3H), 2.90 (m, 1H), 3.12 (m, 1H), 3.73 (m, 2H), 3.94 (m, 1H), 4.37, (q, 2H), 4.83 (t, 1H), 7.36 (s, 1H), 7.70 (d, 2H), 7.81 (d, 2H), 7.89 (s, 1H), 8.44 (s, 1H) | 477 | Ex 41 |
| 152[1] | 5-Chloro-4-(1-ethyl-2-methylimidazol-5-yl)-2-[4-(N-cyclopropylsulphamoyl)anilino]pyrimidine | 0.60 (m, 4H), 1.25 (t, 3H), 2.31 (m, 1H), 2.53 (s, 3H), 4.39 (q, 2H), 4.96 (brs, 1H), 7.37 (s, 1H), 7.71 (d, 2H), 7.85 (m, 3H), 8.45 (s, 1H) | 433 | Ex 53 |
| 153[1] | 5-Chloro-4-[1-(2-methoxyethyl)-2-methylimidazol-5-yl]-2-{4-[N-(2-methoxyethyl)sulphamoyl]anilino}pyrimidine | 2.44 (s, 3H), 2.87 (q, 2H), 3.03 (s, 3H), 3.15 (s, 3H), 3.29 (m, 2H), 3.38 (m, 2H), 4.60 (m, 2H), 7.50 (br t, 1H), 7.64 (s, 1H), 7.72 (d, 2H), 7.83 (d, 2H), 8.63 (s, 1H), 10.10 (s, 1H) | 481 | Ex 61 |

[1]Purified by column chromatography eluting with DCM/MeOH (98:2 increasing in polarity to 96:4).

Example 154

4-(1,2-Dimethylimidazol-5-yl)-2-{4-[N-(2,3-dihydroxypropyl)sulphamoyl]anilino}pyrimidine Water (0.5 ml) followed by TFA (2.5 ml) was added to a solution of 4-(1,2-dimethylimidazol-5-yl)-2-{4-[N-(2,2-dimethyl-1,3-dioxalon-4-ylmethyl)sulphamoyl]anilino}pyrimidine (Example 38, 119 mg, 0.26 mmol) in DCM (2 ml) and the mixture stirred at ambient temperature for 1 hour. The solvent was evaporated and 1M ethereal hydrogen chloride (5 ml) and ether (20 ml) added to the residue. The resulting precipitate was collected by filtration and dried under vacuum. The solid was suspended in MeOH (2 ml) and 1M aqueous lithium hydroxide solution (2 ml) was added and the mixture stirred for 1 hour at ambient temperature. The reaction mixture was poured onto an Isolute SCX-2 column, washed with MeOH (10×15 ml) and the product eluted with 2% methanolic ammonia (5×15 ml). The solvent was removed by evaporation to give the title compound (66 mg, 61%) as a white solid. NMR 2.38 (s, 3H), 2.60 (m, 1H), 2.83 (m, 1H), 3.25 (m, 2H), 3.43 (m, 1H), 3.95 (s, 3H), 4.48 (t, 1H), 4.70 (d, 1H), 7.20 (m, 2H), 7.62 (s, 1H), 7.69 (d, 2H), 7.90 (d, 2H), 8.41 (d, 1H), 9.90 (s, 1H); m/z 419.

Example 155

5-Chloro-4-(1,2-dimethylimidazol-5-yl)-2-(4-sulphamoylanilino)pyrimidine

A mixture of 5-chloro-4-(1,2-dimethylimidazol-5-yl)-2-{4-[N-(t-butyl)sulphamoyl]anilino}pyrimidine (Example 60; 116 mg, 0.267 mmol), trifluoroacetic acid (2.7 ml), water (0.3 ml) and anisole (145 μl, 1.34 mmol) was stirred at ambient temperature for 72 hours. The mixture was then concentrated by evaporation and the residue treated with water and ether. The precipitated solid was collected by filtration, washed with water and ether, and dried to give the title compound (87 mg, 86%) as a white solid. NMR: 2.4 (s, 3H), 3.78 (s, 3H), 7.15 (s, 2H), 7.65 (s, 1H), 7.73 (d, 2H), 7.83 (d, 2H), 8.6 (s, 1H), 10.11 (s, 1H); m/z 3.78 (M−H)⁻.

Example 156

The following compounds were synthesised in an analogous method to Example 155.

| Ex | Compound | NMR | m/z | SM |
|---|---|---|---|---|
| 156 | 5-Chloro-4-(1,2-dimethylimidazol-5-yl)-2-[4-(N-methylsulphamoyl)anilino]pyrimidine | 2.38 (d, 3H), 2.43 (s, 3H), 3.78 (s, 3H), 7.2 (1H, q), 7.67 (m, 3H), 7.87 (d, 2H), 8.63 (s, 1H), 10.17 (s, 1H) | 391 (M-H)⁻ | Ex 71 |

Example 157

5-Bromo-4-(1-methylimidazol-5-yl)-2-(4-sulphamoylanilino)pyrimidine

Bromine (75.5 mg, 0.47 mmol) was added to a solution of 4-(1-methylimidazol-5-yl)-2-(4-sulphamoylanilino)pyrimidine (Example 15; 0.14 g, 0.42 mmol) and sodium acetate (41.7 mg, 0.51 mmol) in acetic acid (4 ml) and the mixture stirred for 1 hour. The volatiles were evaporated and the residue partitioned between EtOAc and saturated aqueous potassium hydrogen carbonate solution. The organic phase was separated and dried. The residue was pre-absorbed on to silica gel and purified by column chromatography on silica gel eluting with DCM/2% methanolic ammonia (9:1) to give the title compound (91 mg, 52%). NMR 10.14 (s, 1H), 8.75 (s, 1H), 7.90–7.69 (m, 4H), 7.17 (s, 2H), 3.84 (s, 3H); m/z 409.

Example 158

2-(3-Chloroanilino)-4-[1-(2-acetamidoethyl)imidazol-5-yl]pyrimidine

Acetic anhydride (0.58 μl, 1.0 mmol) was added to solution of 2-(3-chloroanilino)-4-[1-(2-aminoethyl)imidazol-5-yl]pyrimidine (Example 13; 0.30 g, 0.63 mmol) in pyridine (2 ml) at 0° C. The mixture was allowed to warm to ambient temperature and stirred for 2 hours. 7M Methanolic ammonia (0.5 ml) was added and the mixture diluted with EtOAc (10 ml). The precipitate was removed by filtration and the filtrate pre-absorbed on to silica gel and purified by column chromatography on silica gel eluting with DCM/2% methanolic ammonia (11:1) to give the title compound (88 mg, 39%) as a white solid. NMR 9.68 (s, 1H), 8.43 (d, 1H), 8.03–7.96 (m, 2H), 7.81 (s, 1H), 7.79 (s, 1H), 7.60 (dd, 1H), 7.33 (t, 1H), 7.12 (d, 1H), 6.98 (dd, 1H), 4.56–4.46 (m, 2H), 3.44–3.37 (m, 2H), 1.80 (s, 3H); m/z 357.

Examples 159

The following compound was synthesised in an analogous method to Example 158 using the appropriate sulphonyl chloride in place of acetic anhydride.

| Ex | Compound | NMR | m/z | SM |
|----|----------|-----|-----|----|
| 159 | 2-(3-Chloroanilino)-4-[1-(2-mesylaminoethyl)imidazol-5-yl]pyrimidine | 9.41 (s, 1H), 8.43 (d, 1H), 7.93 (m, 1H), 7.83 (s, 2H), 7.57 (dd, 1H), 7.33 (t, 1H), 7.24 (d, 1H), 7.22–7.17 (m, 1H), 7.00 (dd, 1H), 4.64–4.57 (m, 2H), 3.29–3.22 (m, 2H), 2.78 (s, 3H) | 393, 395 | Ex 13 |

Example 160

4-(1,2-Dimethylimidazol-5-yl)-2-[4-(N-methylsulphamoyl)anilino]pyrimidine

N-Methyl-4-aminobenzenesulphonamide (Method 110; 250 mg, 1.3 mmol) was dissolved in MeOH (3 ml) and 1M HCl in ether (1.3 ml, 1.3 mmol) added. Cyanamide (68 mg, 1.6 mmol) was added along with DMA (0.5 ml). The mixture was heated to 100° C. for 30 min. To this was added 5-(3-dimethylaminoprop-2-en-1-oyl)-1,2-dimethylimidazole (Method 15; 230 mg, 1.2 mmol) and sodium methoxide (150 mg, 2.6 mmol) and heated to 180° C. for 1 hr. The reaction mixture was poured into sat. sodium hydrogen carbonate solution and the resultant solid collected. The solid was triturated with hot DMF and filtered. The filtrate was evaporated in vacuo and purified by flash chromatography on silica gel eluting with DCM/2% methanolic ammonia (100:0 increasing in polarity to 85:15) to yield a white solid which was digested with acetonitrile to yield the title compound as a solid (84 mg, 20%). NMR: 2.38 (d, 6H), 3.95 (s, 3H), 7.19 (d, 2H), 7.63 (s, 1H), 7.68 (d, 2H), 7.93 (d, 2H), 8.43 (d, 1H), 9.91 (s, 1H); m/z 359.

Examples 161–164

The following compounds were synthesised in an analogous method to Example 160.

| Ex | Compound | NMR | m/z | SM |
|----|----------|-----|-----|----|
| 161 | 4-(1,2-Dimethylimidazol-5-yl)-2-[2-methoxy-4-(N-methylsulphamoyl)-5-methylanilino]pyrimidine | 2.36 (s, 3H), 2.41 (d, 3H), 3.88 (s, 3H), 3.90 (s, 3H), 7.20 (d, 1H), 7.30 (br q, 1H), 7.37 (s, 1H), 7.64 (s, 1H), 8.16 (s, 1H), 8.27 (s, 1H), 8.40 (d, 1H) | 403 | Meth 15 |
| 162 | 4-(1,2-Dimethylimidazol-5-yl)-2-{4-[N-(4,5-dimethyloxazol-2-yl)sulphamoyl]anilino}pyrimidine | 1.91 (s, 3H), 2.02 (s, 3H), 2.37 (s, 3H), 3.94 (s, 3H), 7.16 (d, 1H), 7.62 (s, 1H), 7.75 (d, 2H), 7.83 (d, 2H), 8.41 (d, 1H), 9.82 (s, 1H) | 440 | Meth 15 |
| 163 | 4-(1,2-Dimethylimidazol-5-yl)-2-[4-(N-methylcarbamoyl)anilino]pyrimidine | 2.36 (s, 3H), 2.76 (d, 3H), 3.95 (s, 3H), 7.14 (d, 1H), 7.61 (s, 1H), 7.77 (s, 4H), 8.20 (brq, 1H), 8.40 (d, 1H), 9.71 (s, 1H) | 323 | Meth 15 |
| 164 | 4-(1,2-Dimethylimidazol-5-yl)-2-(4-acetamidoanilino)pyrimidine | 2.00 (s, 3H), 2.35 (s, 3H), 3.90 (s, 3H), 7.02 (d, 1H), 7.47 (d, 2H), 7.57 (m, 3H), 8.31 (d, 1H), 9.33 (s, 1H), 9.77 (s, 1H) | 323 | Meth 15 |

Example 165

4-(1,2-Dimethylimidazol-5-yl)-2-(4-aminoanilino)pyrimidine

Sodium hydroxide (1.2 g, 3.0 mmole) was added to a solution of 4-(1,2-dimethyl-imidazol-5-yl)-2-(4-acetamidoanilino)pyrimidine (Example 164; 1.25 g, 3.88 mmole) in isopropanol (12 mL) and water (0.5 mL) and the mixture heated under reflux for 90 minutes. The mixture was allowed to cool and was partitioned between saturated aqueous sodium hydrogen carbonate solution and EtOAc. The organic layer was separated and the volatiles evaporated. The residue was purified by column chromatography on silica gel eluting with DCM/7M methanolic ammonia (96:4) to give the title compound (0.75 g, 69%) as a brown solid. NMR: 2.33 (s, 3H), 3.85 (s, 3H), 4.75 (brs, 2H), 6.51 (d, 2H), 6.92 (d, 1H), 7.22 (d, 2H), 7.51 (s, 1H), 8.22 (d, 1H), 8.90 (s, 1H); m/z 281.

Preparation of Starting Materials

The starting materials for the examples above are either commercially available or are readily prepared by standard methods from known materials. For example, the following reactions are an illustration, but not a limitation, of some of the starting materials used in the above reactions.

Method 1

5-(3-Dimethylaminoprop-2-enoyl)-1,2-dimethylimidazole 5-(3-Dimethylaminoprop-2-enoyl)-2-methylimidazole (350 mg, 1.95 mmol) was suspended in DMFDMA (14 ml) and the mixture stirred and heated at 100° C. for 56 hours. The excess DMFDMA was removed by evaporation and the residue purified by chromatography eluting with DCM/MeOH (94:6) to give the title compound 111 mg, (29%) as a solid. NMR (CDCl$_3$): 2.40 (s, 3H), 3.00 (s, 6H), 3.88 (s, 3H), 5.50 (d, 1H), 7.47 (s, 1H), 7.65 (d, 1H); m/z 194.

Method 2

2-(3-Chloroanilino)-4-(1-triphenylmethylimidazol-4-yl)pyrimidine 4-(3-Dimethylaminoprop-2-en-1-oyl)-1-triphenylmethylimidazole (Method 3) was treated with 3-chlorophenylguanidine under conditions analogous to those described in Example 7 to give the title compound; m/z: 514.

Method 3

4-(3-Dimethylaminoprop-2-en-1-oyl)-1-triphenylmethylimidazole

A suspension of 4-acetyl-1-triphenylmethylimidazole (Method 6; 11.9 g, 33.9 mmol) in DMFDMA (30 ml) was heated at reflux for 24 hours. The solution was allowed to cool and the precipitate collected by filtration to give the title compound 10.7 g, (78%). M/z: 408.

Methods 4–5

The following compounds were prepared by the procedure of Method 3.

| Meth | Compound | M/z |
|---|---|---|
| 4 | 5-(3-Dimethylaminoprop-2-en-1-oyl)-1-methylimidazole | 180 |
| 5 | 1-Benzyl-5-(3-dimethylaminoprop-2-en-1-oyl)-2-methylimidazole | 270 |

Method 6

4-Acetyl-1-triphenylmethylimidazole

A solution of 4-(1-hydroxyethyl)-1-triphenylmethylimidazole (Method 10; 30.5 g, 86 mmol) in dioxane (500 ml) was heated to 100° C. Manganese dioxide (63.6 g, 0.73 mol) was added in portions so that a gentle reflux was maintained. The mixture was allowed to cool slightly and the inorganic solids were removed by filtration. The volatiles were removed from the filtrate by evaporation to give the title compound 30.3 g, (99%) as a solid product. NMR: 2.55 (s, 3H), 7.04–7.40 (m, 15H), 7.43 (s, 1H), 7.57 (s, 1H).

Methods 7–8

The following compounds were prepared by the procedure of Method 6.

| Meth | Compound | DATA |
|---|---|---|
| 7 | 5-Acetyl-1-methylimidazole | M/z: 125 |
| 8 | 5-Acetyl-1-benzyl-2-methylimidazole | NMR: 2.38 (s, 3H), 2.44 (s, 3H), 5.60 (s, 2H), 6.99 (d, 2H), 7.22–7.31 (m, 3H), 7.77 (s, 1H) |

Method 9

5-(1-Hydroxyethyl)-1-methylimidazole

Methyl magnesium bromide (100 ml of a 3M solution in diethyl ether, 0.30 mol) was added dropwise to a solution of 5-formyl-1-methylimidazole (14.5 g, 0.13 mol) in THF (750 ml) cooled to −20° C. such that the reaction temperature was kept below 3° C. The mixture was allowed to warm to ambient temperature and water (150 ml) was carefully added. The aqueous mixture was continuously extracted with EtOAc. The EtOAc extract was dried, and the volatiles removed by evaporation to give the title compound 14.4 g, (88%) as a solid product. NMR: 1.41 (d, 3H), 4.65–4.77 (m, 1H), 4.96–5.11 (m, 1H), 6.72 (s, 1H), 7.47 (s, 1H).

Methods 10–11

The following compounds were prepared by the procedure of Method 9.

| Meth | Compound | DATA |
|---|---|---|
| 10 | 4-(1-Hydroxyethyl)-1-triphenylmethylimidazole | NMR: 1.28 (d, 3H), 4.58 (m, 1H), 4.83 (d, 1H), 6.65 (s, 1H), 7.03–7.10 (m, 6H), 7.23 (d, 1H), 7.33–7.43 (m, 9H) |
| 11 | 1-Benzyl-5-(1-hydroxyethyl)-2-methylimidazole | M/z: 217 |

Method 12

1-Benzyl-5-formyl-2-methylimidazole

Benzyl bromide (21.4 ml, 0.18 mol) was added carefully to a mixture of 4-formyl-2-methylimidazole (18.1 g, 0.16 mol) and potassium carbonate (45.0 g, 0.33 mol) in DMF (100 ml) at 0° C. and the reaction mixture allowed to warm to ambient temperature. The mixture was then partitioned between EtOAc and saturated aqueous sodium hydrogen carbonate solution, the organic phase separated and dried. The volatiles were removed by evaporation to give the title compound as crude mixture of regioisomers 32.0 g, (99%). M/z: 201.

Method 13

4-{N-[3-(Pyrrolidin-2-on-1-yl)propyl]sulphamoyl}aniline

Sulphanilyl fluoride (6.5 g, 37.1 mmol), 3-(pyrrolidin-2-on-1-yl)propylamine (5.79 g, 40.8 mmol) and triethylamine (5.69 ml, 40.8 mmol) in n-butanol (15 ml) was heated at reflux for 10 hours. The mixture was allowed to cool, silica was added and the volatiles were evaporated. The residue was purified by chromatography eluting with DCM/MeOH (100:0) increasing in polarity to (90:10) to give the title compound m/z: 297.

Method 14

The following compound was prepared using the procedure of Method 13.

| Meth | Compound | m/z |
|---|---|---|
| 14 | 4-[N-(2-Tetrahydrofuranylmethyl)sulphamoyl]aniline | 257 |

Method 15

5-(3-Dimethylaminoprop-2-en-1-oyl)-1,2-dimethylimidazole

2-Methyl-4-acetylimidazole (129 g, 1.04 mol) was dissolved in a mixture of DMF (900 ml) and DMF.DMA (1.51) and the mixture heated under reflux, under an atmosphere of nitrogen, for 18 hours. The reaction mixture was allowed to cool to ambient temperature the product crystallised. The solid product was collected by filtration, washed with DMFDMA and then ether and dried under vacuum at 40° C. to give the title compound (115 g, 57%) as a pale brown crystalline solid. NMR 2.13 (s, 3H), 2.95 (s, 6H), 3.78 (s, 3H), 5.56 (d, 1H), 7.50 (d, 1H), 7.53 (s, 1H); m/z 194.

Methods 16–25

The following compounds were synthesised in an analogous method to Method 15.

| Ex | Compound | NMR | m/z | SM |
|---|---|---|---|---|
| 16[1] | 5-(3-Dimethylaminoprop-2-en-1-oyl)-1-ethyl-2-methylimidazole | 1.17 (t, 3H), 2.16 (s, 3H), 2.95 (s, 6H), 4.27 (q, 2H), 5.57 (d, 1H), 7.50 (d, 1H), 7.53 (s, 1H) | 208 | Meth 35 |
| 17[2] | 5-(3-Dimethylaminoprop-2-en-1-oyl)-1-(2-methoxyethyl)-2-methylimidazole | 2.29 (s, 3H), 2.95 (brs, 6H), 3.15 (s, 3H), 3.52 (t, 2H), 4.41 (t, 2H), 5.58 (d, 1H), 7.51 (d, 1H), 7.58 (s, 1H) | 238 | Meth 36 |
| 18[3] | 1-(1-Butene-4-yl)-5-(3-dimethylaminoprop-2-en-1-oyl)-2-methylimidazole | (CDCl$_3$) 2.41 (s, 3H), 2.49 (q, 2H), 2.99 (brs, 6H), 4.39 (t, 2H), 5.02 (s, 1H), 5.07 (d, 1H), 5.52 (d, 1H), 5.79 (m, 1H), 7.49 (s, 1H), 7.66 (d, 1H) | 234 | Meth 37 |
| 19[7] | 5-(3-Dimethylaminoprop-2-en-1-oyl)-1-(isopropyl)-2-methylimidazole | 1.43 (d, 6H), 2.40 (s, 3H), 2.95 (brs, 6H), 3.31 (s, 3H), 5.22 (sept, 1H), 5.54 (d, 1H), 7.48 (s, 1H), 7.52 (d, 1H) | 222 | Meth 101 |
| 20[1] | 5-(3-Dimethylaminoprop-2-en-1-oyl)-1-methyl-2-ethylimidazole | 1.20 (t, 3H), 2.62 (q, 2H), 2.95 (s, 6H), 3.78 (s, 3H), 5.56 (d, 1H), 7.51 (m, 2H) | 208 | Meth 96 |
| 21[1] | 5-(3-Dimethylaminoprop-2-en-1-oyl)-1-(2,2,2-trifluoroethyl)-2-methylimidazole | 2.34 (s, 3H), 2.85 (s, 3H), 3.10 (s, 3H), 5.46 (q, 2H), 5.57 (d, 1H), 7.56 (d, 1H), 7.62 (s, 1H) | 262 | Meth 109 |
| 22[5] | 5-(3-Dimethylaminoprop-2-en-1-oyl)-1-methyl-2-isopropylimidazole | 1.20 (d, 6H), 3.05 (m, 1H), 3.80 (s, 3H), 5.53 (d, 1H), 7.50 (m, 2H) | 222 | Meth 98 |
| 23[6] | 5-(3-Dimethylaminoprop-2-en-1-oyl)-1-methyl-2-trifluoromethylimidazole | 2.95 (s, 3H), 3.15 (s, 3H), 4.11 (s, 3H), 5.49 (d, 1H), 7.53 (s, 1H), 7.73 (d, 1H) | 248 | Meth 92 |
| 24[4] | 5-(3-dimethylaminoprop-2-en-1-oyl)-1,2,4-trimethylimidazole | 2.21 (s, 3H), 2.22 (s, 3H), 2, 90 (s, 3H), 3.05 (s, 3H), 3.58 (s, 3H), 5.28 (d, 1H), 7.51 (d, 1H) | 207 | Meth 107 |
| 25[5] | 5-(3-Dimethylaminoprop-2-en-1-oyl)-1-methyl-2-methoxymethyllimidazole | 2.87 (s, 3H), 3.05 (s, 3H), 3.20 (s, 3H), 3.83 (s, 3H), 4.45 (s, 2H), 5.58 (d, 1H), 7.55 (d, 1H), 7.59 (s, 1H) | 224 | Meth 93 |

[1]Only DMF.DMA used as solvent.
[2]Reaction was worked up by evaporation. The resulting gum suspended in ether (60 ml), the insolubles were removed by filtration and the filtrate was evaporated to give the product as a solid.
[3]Reaction heated 96 hours. Reaction evaporated and residue purified by flash chromatography on silica gel eluting with DCM/MeOH (100:0 increasing in polarity to 95:5).
[4]Reaction was heated under reflux in neat DMF.DMA for 72 hrs. Reaction mixture was evaporated and the residue triturated with ether and the solid product collected filtration.
[5]Purified by flash chromatography on silica gel eluting with DCM/2% methanolic ammonia (100:0 increasing in polarity to 95:5).
[6]Purified by flash chromatography on silica gel eluting with EtOAc/MeOH (100:0 increasing in polarity to 70:30).
[7]Purified by flash chromatography on silica gel eluting with DCM/MeOH (98:2 increasing in polarity to 92.5:7.5)

Method 26

2-Amino-4-(1,2-dimethylimidazol-5-yl)pyrimidine 5-(3-Dimethylaminoprop-2-en-1-oyl)-1,2-dimethylimidazole (Method 15; 2.8 g, 14.5 mmol) and guanidine hydrochloride (3.5 g, 36.3 mmol) were suspended in 1-butanol (30 ml). Sodium methoxide (3.1 g, 58 mmol) was added in one portion and the mixture heated under reflux, under an atmosphere of nitrogen, for 18 hours. The reaction mixture was allowed to cool to ambient temperature and was pre-absorbed on to silica gel and purified by column chromatography on silica gel eluting with DCM/2% methanolic ammonia (100:0 increasing in polarity to 95:5) to give the title compound (2.3 g, 84%). NMR 2.16 (s, 3H), 3.93 (s, 3H) 6.52 (s, 2H), 6.80 (d, 1H), 7.47 (s, 1H), 8.17 (d, 1H); m/z 190.

Methods 27–32

The following compounds were synthesised in an analogous method to Method 26.

| Ex | Compound | NMR | m/z | SM |
|---|---|---|---|---|
| 27 | 2-Amino-4-(1-ethyl-2-methylimidazol-5-yl)pyrimidine | 1.24 (t, 3H), 2.40 (s, 3H), 4.40 (q, 2H), 4.88 (s, 2H), 6.78 (d, 1H), 7.41 (s, 1H), 8.14 (d, 1H) | 204 | Meth 16 |
| 28[1] | 2-Amino-4-[1-(2-methoxyethyl)-2-methylimidazol-5-yl]pyrimidine | 2.35 (s, 3H), 3.14 (s, 3H), 3.58 (t, 2H), 4.64 (t, 2H), 6.49 (brs, 2H), 6.83 (d, 1H), 7.51 (s, 1H), 8.11 (d, 1H) | 234 | Meth 17 |
| 29[2] | 2-Amino-4-[1-(1-buten-4-yl)-2-methylimidazol-5-yl]pyrimidine | 2.50 (s, 5H), 4.54 (t, 2H), 4.94 (d, 1H), 4.99 (d, 1H), 5.80 (m, 1H), 6.49 (brs, 2H), 6.84 (d, 1H), | 230 | Meth 18 |

-continued

| Ex | Compound | NMR | m/z | SM |
|---|---|---|---|---|
| 30[3] | 2-Amino-4-(1-methyl-2-ethylimidazol-5-yl)pyrimidine | 7.51 (s, 1H), 8.13 (d, 1H) 1.38 (t, 3H), 2.76 (d, 2H), 3.94 (s, 3H), 5.00 (s, 2H), 6.83 (d, 1H), 7.51 (s, 1H), 8.12 (d, 1H) | 204 | Meth 20 |
| 31[3] | 2-Amino-4-(1-methyl-2-isopropylimidazol-5-yl)pyrimidine | 1.40 (d, 6H), 3.13 (m, 1H), 3.98 (s, 3H), 5.00 (s, 2H), 6.83 (d, 1H), 7.50 (s, 1H), 8.22 (d, 1H) | 218 | Meth 22 |
| 32[4] | 2-Amino-4-(1-methyl-2-trifluoromethylimidazol-5-yl)pyrimidine | 4.16 (s, 3H), 5.13 (s, 2H), 6.87 (d, 1H), 7.53 (s, 1H), 8.35 (d, 1H) | 244 | Meth 23 |

[1]Reaction refluxed for 2 hrs 40 mins. Reaction mixture was evaporated, water added and the mixture was extracted with EtOAc. The extract was washed with brine, dried and evaporated.
[2]Reaction evaporated under vacuum. Added water and extracted into EtOAc. Extract washed with brine, dried and evaporated.
[3]Purified by column chromatography on silica gel eluting with EtOAc/MeOH (100:0 increasing in polarity to 50:50).
[4]Purified by column chromatography on silica gel eluting with EtOAc/MeOH (100:0 increasing in polarity to 70:30).

Method 33

1-(Triphenylmethyl)-2-methyl-4-(2-hydroxyethyl)imidazole

Triphenylmethyl chloride (24.5 g, 88 mmol) in DMF (100 ml) was added dropwise over 1 hr to a solution of 2-methyl-4-(2-hydroxyethyl)imidazole (10 g, 80 mmol) and triethylamine in DMF (100 ml). The reaction mixture was stirred at ambient temperature for 18 hours and then the volatiles were removed by evaporation. The resultant solid was triturated with water (3×500 ml) and ether (200 ml), collected by filtration and dried under vacuum at 60° C. to give the title compound (23.7 g, 80%) as a pale yellow solid. NMR 1.43 (d, 3H), 1.62 (s, 3H), 2.53 (s, 1H), 4.80 (q, 1H), 6.59 (s, 1H), 7.13 (m, 6H), 7.37 (m, 9H); m/z 369.

Method 34

1-(Triphenylmethyl)-2-methyl-4-acetylimidazole 1-(Triphenylmethyl)-2-methyl-4-(2-hydroxyethyl)imidazole Method 33; 23.7 g, 64 mmol) was suspended in chloroform (180 ml) under nitrogen. Activated manganese (IV)oxide (27.8 g, 320 mol) was added in one portion and the mixture heated at reflux for 3 hours. The reaction mixture was allowed to cool then filtered through a pad of diatomaceous earth and the pad washed thoroughly with chloroform. The filtrate was evaporated to give the title compound (23.4 g, 100%) as a pale yellow powder. NMR 1.71 (s, 3H), 2.53 (s, 3H), 7.13 (m, 6H), 7.37 (m, 9H), 7.52 (s, 1H); m/z 367.

Method 35

1-Ethyl-2-methyl-5-acetylimidazole

Ethyl triflate (11 ml, 83.2 mmol) was added dropwise over 15 minutes to a solution of 1-(triphenylmethyl)-2-methyl-4-acetylimidazole (Method 34; 23.4 g, 64 mmol) in DCM (300 ml) and the mixture stirred for 5 hours at ambient temperature. The solution was diluted with DCM (100 ml) and extracted with 1M aqueous citric acid solution (5×75 ml). The aqueous extracts were combined, basified with solid sodium hydrogen carbonate and the extracted with DCM (5×75 ml). The organic extracts were combined, dried and evaporated to give the title compound (8.59 g, 88%) as a pale yellow oil. NMR 1.32 (t, 3H), 2.41 (s, 6H), 4.29 (q, 2H), 7.68 (s, 1H); m/z 153.

Method 36

1-(2-Methoxyethyl)-2-methyl-5-acetylimidazole

A solution of 2-methoxyethyl triflate (prepared on a 6 mmole scale from 2-methoxyethanol and trifluoromethanesulphonic anhydride by the method published in Synthesis 1982 85) in DCM (20 ml) was added dropwise to a solution of 1-(triphenylmethyl)-2-methyl-4-acetylimidazole (Method 34; 1.5 g, 4 mmol) in DCM (5 ml) and the mixture was stirred for 40 hours at ambient temperature. The volatiles were removed by evaporation to give a solid (2.4 g) which was purified by flash chromatography on silica gel eluting with DCM/MeOH (100:0 increasing in polarity to 95:5) to yield the title compound (660 mg, 88%) as a solid NMR (CDCl$_3$) 1.31 (s, 3H), 1.49 (s, 3H), 2.02 (s, 3H), 2.43 (m, 2H), 3.31 (m, 2H), 6.87 (s, 1H); m/z 183.

Method 37

1-(1-Buten-4-yl)-2-methyl-5-acetylimidazole

The title compound was synthesised in an analogous method to Method 36, using the triflate derived from cyclopropanemethanol. The title compound was obtained as an oil after flash chromatography on silica gel eluting with DCM/MeOH (100:0 increasing in polarity to 96:4). NMR (CDCl$_3$) 2.43 (m, 8H), 4.32 (t, 2H), 5.02 (m, 1H), 5.08 (s, 1H), 5.74 (m, 1H), 7.69 (s, 1H); m/z 179.

Method 38

{N-[2-(Methoxymethoxyethyl)]carbamoyloxymethyl}phenyl

Chloromethyl methyl ether (5 ml, 65 mmol) added cautiously to a solution of [N-(2-hydroxyethyl)carbamoyloxymethyl]phenyl (6.45 g, 33 mmol) and diisopropylethylamine (12 ml, 70 mmol) in DCM (50 ml) and the reaction was stirred at ambient temperature for 4 hours. The volatiles were removed by evaporation and the residue dissolved in EtOAc (100 ml), washed 1M aqueous citric acid solution (2×50 ml), saturated aqueous sodium hydrogen carbonate solution (50 ml), and then brine (50 ml), dried and evaporated to give the title compound (7.64 g, 97%) as a colourless oil. NMR 3.34 (s, 3H), 3.42 (q, 2H), 3.61 (t, 2H), 4.60 (s, 3H), 5.14 (m, 3H), 7.34 (m, 5H); m/z 262 (M+Na)$^+$.

Method 39

N-[2-(Methoxymethoxy)ethyl]-4-iodobenzenesulphonamide

A suspension of {N-[2-(methoxymethoxy)ethyl]carbamoyloxymethyl}phenyl (Method 38, 2.4 g, 10 mmol) and 10% palladium on carbon (300 mg) in THF (20 ml) was stirred under an atmosphere of hydrogen at ambient temperature for 18 hours. The catalyst was removed by filtration and the filtrate was placed under nitrogen. Triethylamine (1 ml, 7.5 mmol) and 4-iodophenylsulphonyl chloride (1.82 g, 6 mmol) were added and the mixture was stirred at ambient temperature for 2 hours. The reaction mixture was poured into a mixture of EtOAc (30 ml) and 1M aqueous citric acid solution (30 ml). The phases were separated and the aqueous phase washed with EtOAc (30 ml). The organic extracts were combined, washed 1M aqueous citric acid solution (2×30 ml), brine (30 ml), dried and the volatiles removed by evaporation to yield the title compound (2.18 g, 98%) as a waxy solid. NMR 3.15 (q, 2H), 3.31 (s, 3H), 3.59 (t, 2H), 4.53 (s, 2H), 4.96 (t, 1H), 7.58 (d, 2H), 7.90 (d, 2H); m/z 370 (M–H)–.

Method 40

N-(2-Methoxyethyl)-4-iodobenzenesulphonamide

A solution of 4-iodophenylsulphonyl chloride (3.64 g, 12 mmol) in DCM (30 ml) was added dropwise to a solution of 2-methoxyethylamine (1.3 ml, 15 mmol) and triethylamine (2 ml, 15 mmol) in DCM (60 ml) cooled by an ice bath to 0° C. The mixture was then allowed to warm to ambient temperature and stirred for 1 hour. The solvent was removed by evaporation and the resulting oil dissolved EtOAc (100 ml) and washed with 1N aqueous citric acid solution (2×100 ml), brine (100 ml) and dried. The volatiles were removed by evaporation to give the title compound (4.1 g, 100%) as a clear oil. NMR 3.12 (2H, q), 3.28 (3H, s), 3.44 (2H, t), 4.90 (1H, t), 7.57 (2H, d), 7.81 (2H, d); m/z: 342.

Methods 41–53

The following compounds were synthesised in an analogous method to Method 40.

| Ex | Compound | NMR | m/z |
|----|----------|-----|-----|
| 41 | N-(Cyclopropylmethyl)-4-iodobenzenesulphonamide | 0.01 (m, 2H), 0.32 (m, 2H), 0.76 (m, 1H), 2.60 (t, 2H), 7.47 (d, 2H), 7.72 (t, 3H), 7.91 (d, 2H) | 336 |
| 42 | N-(2,2-Dimethyl-1,3-dioxolan-4-ylmethyl)-4-iodobenzenesulphonamde | 1.20 (s, 3H), 1.25 (s, 3H), 2.91 (m, 1H), 3.12 (m, 1H), 3.60 (m, 1H), 3.92 (m, 1H), 4.13 (m, 1H), 4.71 (t, 1H), 7.52 (d, 2H), 7.80 (d, 2H) | 396 |
| 43[1] | N-(2-Benzyloxyethyl)-4-iodobenzenesulphonamide | 3.12 (q, 2H), 3.42 (m, 2H), 4.35 (s, 2H), 4.80 (m, 1H), 7.25 (m, 5H), 7.48 (d, 2H), 7.79 (d, 2H) | 418 |
| 44 | N-(2,2-Dimethoxyethyl)-4-iodobenzenesulphonamide | 3.00 (t, 2H), 3.28 (s, 6H), 4.24 (t, 1H), 4.64 (t, 1H), 7.51 (d, 2H), 7.80 (d, 2H) | 370 |
| 45 | N-(Tetrahydrofur-2-ylmethyl)-4-iodobenzenesulphonamide | 1.50 (m, 1H), 1.80 (m, 3H), 2.81 (m, 1H), 3.10 (m, 1H), 3.65 (m, 2H), 3.84 (m, 1H), 4.89 (t, 1H), 7.49 (d, 2H), 7.80 (d, 2H) | 368 |
| 46 | N-(3-Methoxypropyl)-4-iodobenzenesulphonamide | 1.68 (m, 2H), 3.02 (q, 2H), 3.21 (s, 3H), 3.38 (t, 2H), 5.10 (s, 1H), 7.51 (d, 2H), 7.80 (d, 2H) | 356 |
| 47 | N-(Cyclopropyl)-4-iodobenzenesulphonamide | 0.60 (4H, d), 2.27 (1H, m), 4.85 (1H, s), 7.60 (2H, d), 7.90 (2H, d) | 322 (M–H)– |
| 48 | N-(4-Methylthiazol-2-ylmethyl)-4-iodobenzenesulphonamide | 2.22 (s, 3H), 4.26 (d, 2H), 7.11 (s, 1H), 7.53 (d, 2H), 7.94 (d, 2H), 8.60 (t, 1H) | 395 |
| 49 | N-(3-Methylisoxazol-5-ylmethyl)-4-iodobenzenesulphonamide | 2.11 (s, 3H), 4.16 (d, 2H), 6.02 (s, 1H), 7.48 (d, 2H), 7.93 (d, 2H), 8.43 (t, 1H) | 377 (M–H)– |
| 50 | N-(1,4-Dioxan-2-ylmethyl)-4-iodobenzene sulphonamide | 2.82 (m, 1H), 3.02 (m, 1H), 3.60 (m, 7H), 4.83 (t, 1H), 7.51 (d, 2H), 7.83 (d, 2H) | 382 (M–H)– |
| 51[2] | N-Propyl-4-iodobenzenesulphonamide | 0.9 (t, 3H), 1.5 (q, 2H), 2.93 (q, 2H), 4.45 (t, 1H), 7.57 (d, 2H), 7.87 (d, 2H) | 324 (M–H)– |
| 52[2] | N-(t-Butyl)-4-iodobenzenesulphonamide | 1.07 (s, 9H), 7.55 (m, 3H), 7.93 (d, 2H) | 338 (M–H)– |
| 53 | N-Allyl-4-iodobenzenesulphonamide | 3.20 (t, 2H), 5.00 (d, 1H), 5.10 (d, 1H), 5.66 (m, 1H), 7.52 (d, 2H), 7.85 (t, 1H) 7.96 (d, 2H) | 322 |

[1]Starting material prepared according to JACS 1966; vol 88, 2302.
[2]Triethylamine was replaced by excess of the reacting amine.

Method 54

N-t-Butoxycarbonyl-4-iodobenzenesulphonamide

A solution of di-t-butyl dicarbonate (10 g, 46 mmol) in DCM (80 ml) was added dropwise over 15 min to a stirred solution of 4-iodobenzenesulphonamide (11.3 g, 40 mmol), 4-dimethylaminopyridine (488 mg, 4 mmol) and triethylamine (6.2 ml, 44 mmol) in DCM (50 ml). The reaction was stirred at ambient temperature for 2 hours and the solvent was then removed by evaporation. The residue was dissolved in EtOAc (240 ml), washed 1M aqueous citric acid solution (2×160 ml), brine (160 ml), dried and the solvent removed by evaporation to yield an orange solid. The crude product was recrystallized from EtOAc/isohexane, collected by filtration, washed twice with isohexane and dried to give the title compound (10.25 g, 67%) as off white crystals. NMR 1.40 (s, 9H), 7.71 (d, 2H), 7.90 (d, 2H); m/z 382 (M–H)–.

Method 55

4-(1,2-Dimethylimidazol-5-yl)-2-(4-{N-(t-butoxycarbonyl)-N-[2-(2-methoxyethoxy)ethyl]sulphamoyl}anilino)pyrimidine 2-(2-Methoxyethoxy)ethanol (50 μl, 0.4 mmol) followed by diisopropyl azodicarboxylate (0.1 ml, 0.4 mmol) was added to a stirred solution of 4-(1,2-dimethylimidazol-5-yl)-2-{4-[N-(t-butoxycarbonyl)sulphamoyl]anilino}pyrimidine (Example 36; 90 mg, 0.2 mmol) and triphenylphosphine (105 mg, 0.4 mmol) in anhydrous THF (4 ml) under nitrogen at 0° C. The reaction was allowed to warm to ambient temperature and stirred for 1 hour. The mixture was poured directly on to an Isolute SCX-2 column, eluted first with MeOH (8×15 ml) and then the product was eluted with 2% methanolic ammonia (6×15 ml). The solvent was evaporated and the residue dissolved in EtOAc (25 ml), washed with saturated aqueous sodium hydrogen carbonate solution (2×25 ml), dried and the solvent evaporated to give the title compound (77 mg, 71%) as a yellow oil. NMR 1.38 (s, 9H), 2.49 (s, 3H), 3.38 (s, 3H), 3.56 (m, 2H), 3.68 (m, 2H), 3.76 (t, 2H), 3.96 (s, 3H), 4.06 (t, 2H), 7.03 (d, 1H), 7.49 (s, 1H), 7.58 (s, 1H), 7.78 (d, 2H), 7.93 (d, 2H), 8.40 (d, 1H); m/z 547.

Methods 56–57

The following compounds were synthesised in an analogous method to Method 55.

| Ex | Compound | NMR | m/z | SM |
|---|---|---|---|---|
| 56 | 4-(1,2-Dimethylimidazol-5-yl)-2-[4-(N-(t-butoxycarbonyl)-N-{2-[2-(2-methoxyethoxy)ethoxy]ethyl}sulphamoyl)anilino]pyrimidine | 1.38 (s, 9H), 2.48 (s, 3H), 3.37 (s, 3H), 3.56 (m, 2H), 3.65 (m, 8H), 3.79 (t, 2H), 3.96 (s, 3H), 4.04 (t, 2H), 7.01 (d, 1H), 7.41 (s, 1H), 7.56 (s, 1H), 7.79 (d, 2H), 7.92 (d, 2H), 8.40 (d, 1H) | 591 | Ex 36 |
| 57 | 4-(1,2-Dimethylimidazol-5-yl)-2-{4-[N-(t-butoxycarbonyl)-N-(2-{2-[2-(2-methoxyethoxy)ethoxy[9 ethoxy}ethyl)sulphamoyl]anilino}pyrimidine | 1.38 (s, 9H), 2.48 (s, 3H), 3.37 (s, 3H), 3.56 (m, 2H), 3.65 (m, 12H), 3.79 (t, 2H), 3.96 (s, 3H), 4.04 (t, 2H), 7.01 (d, 1H), 7.41 (s, 1H), 7.56 (s, 1H), 7.79 (d, 2H), 7.92 (d, 2H), 8.40 (d, 1H) | 635 | Ex 36 |

Method 58

4-Iodobenzenesulphonyl fluoride

18-Crown-6 (0.5 g) and potassium fluoride (11.6 g, 200 mmol) were added to a solution of iodobenzenesulphonyl chloride (30.3 g, 100 mmol) in acetonitrile (100 ml) and the suspension was stirred for 18 hours at ambient temperature. The insolubles were removed by filtration and the solvent removed from the filtrate by evaporation. The residue was dissolved in EtOAc (300 ml), washed with water (2×150 ml), brine (100 ml), dried and the solvent evaporated to give the title compound (27.54 g, 96%) as a white solid. NMR 7.70 (d, 2H), 8.01 (d, 2H); m/z 286.

Method 59

4-(1,2-Dimethylimidazol-5-yl)-2-[4-(fluorosulphonyl)anilino]pyrimidine

Caesium carbonate (2.3 g, 7.2 mmol) was added to a degassed solution of 2-amino-4-(1,2-dimethylimidazol-5-yl)pyrimidine (Method 26; 756 mg, 4 mmol), 4-iodosulphonyl fluoride (Method 58; 1.50 g, 5.2 mmol), tris(dibenzylideneacetone)dipalladium (0) (92 mg, 0.18 mmol) and 2,2'-bis(diphenylphosphino)-1,1'-binaphthyl (124 mg, 0.18 mmol) in dioxane (36 ml) under nitrogen. The mixture was heated at 80° C. for 18 hours and then allowed to cool to ambient temperature. The mixture was poured into water (50 ml) and extracted with DCM (2×50 ml). The organic extracts were combined, washed with brine (50 ml), dried and the solvent evaporated. The residue was pre-absorbed on to silica gel and purified by column chromatography on silica gel eluting with DCM/2% methanolic ammonia (100:0 increasing in polarity to 97:3) to give the title compound (984 mg, 71%) as a pale yellow solid. NMR 2.38 (s, 3H), 3.96 (s, 3H), 7.28 (d, 1H), 7.65 (s, 1H), 8.00 (d, 2H), 8.13 (s, 2H), 8.47 (d, 1H), 10.32 (s, 1H); m/z 348.

Method 60

4-[1-(2-Methoxyethyl)-2-methylimidazol-5-yl]-2-N-(4-fluorosulphonylanilino)pyrimidine The title compound was synthesised from Method 28 in an analogous method to Method 59 except that the reaction was evaporated before aqueous work-up and extraction was with EtOAc. The crude product purified by column chromatography on silica gel eluting with DCM/MeOH (98:2 increasing in polarity to 96:4). NMR: (CDCl$_3$) 2.52 (s, 3H), 3.27 (s, 3H), 3.61 (t, 2H), 4.68 (t, 2H), 7.11 (d, 1H), 7.52 (s, 1H, 7.61 (s, 1H), 7.89 (d, 2H), 7.96 (d, 2H), 8.41 (d, 1H); m/z 392.

Method 61

2-Amino-5-bromo-4-(1,2-dimethylimidazol-5-yl)pyrimidine

The title compounds was synthesised from Method 26 in an analogous method to Example 145 except that the reaction was heated at 60° C. for 1.5 hrs, diluted with water and basified 2M aqueous sodium hydroxide solution. The resultant solid was collected by filtration and dried in vac oven at 60° C. NMR: 2.38 (s, 3H), 3.72 (s, 31), 6.84 (s, 2H), 7.55 (s, 1H), 8.38 (s, 1H); m/z 269.

Method 62

N-(2-Methoxyethyl)-N-methyl-4-iodobenzenesulphonamide

Sodium hydride (144 mg, 3.6 mmol) was added in portions to a solution of N-(2-methoxyethyl)-4-iodobenzenesulphonamide (Method 40, 1 g, 3 mmol) in THF (10 ml) and the mixture stirred at ambient temperature for 15 minutes. Iodomethane (230 μl, 3.6 mmol) was added and the reaction stirred for 18 hours. Water (30 ml) was added cautiously and the mixture extracted with ether (40 ml). The combined organics were washed with brine (50 ml), dried and the volatiles evaporated. The residue was purified by flash chromatography on silica gel eluting with iso-hexane/EtOAc (100:0 increasing in polarity to 10:1) to give the title compound (730 mg, 69%) as a clear oil. NMR 2.78 (s, 3H), 3.16 (t, 2H), 3.22 (s, 3H), 3.45 (t, 3H), 7.42 (d, 2H), 7.80 (d, 2H); m/z 356.

Methods 63–64

The following compounds were synthesised in an analogous method to Method 62.

| Ex | Compound | NMR | m/z | SM |
|---|---|---|---|---|
| 63 | N-(3-Morpholinopropyl)-N-methyl-4-iodobenzene sulphonamide | 1.77 (m, 2H), 2.41 (m, 6H), 2.75 (s, 3H), 3.11 (t, 2H), 3.69 (m, 4H), 7.48 (d, 2H), 7.87 (d, 2H) | 425 | Meth 66 |
| 64 | N-(t-Butyl)-N-methyl-4-iodobenzenesulphonamide | (CDCl$_3$): 1.35 (s, 9H), 2.96 (s, 3H), 7.53 (d, 2H), 7.83 (d, 2H) | n/a | Meth 52 |

Method 65

4-Mesylbromobenzene

To a solution of 4-bromothioanisole (22.3 g, 11 mmol) in DCM (250 ml) was added m-chloroperoxybenzoic acid (40 g, 23 mmol) in 10 g portions. The precipitate was removed by filtration and washed with DCM. The filtrate was evaporated in vacuo and the resultant solid recrystallized from EtOH (c.a. 180 ml) to yield the title compound as colourless crystals 11.7 g (45%). Mp 103–106° C.

Method 66

N-(3-Morpholinopropyl)-4-iodobenzenesulphonamide

4-Iodophenylsulphonyl chloride (3.03 g, 10 mmol) in DCM (30 ml) was added dropwise over 15 minutes to a solution of 4-(3-aminopropyl)morpholine (1.75 ml, 12 mmol) and triethylamine (1.7 ml, 12 mmol) in DCM (50 ml) cooled in an ice bath. The mixture was allowed to warm to ambient temperature and stirred for 15 minutes. Water (50 ml) was added and the phases separated. The organic layer was washed with water (50 ml) and brine (50 ml), dried (Chemelut column 1010) and evaporated to give the title compound (4.10 g, 100%) as a beige solid. NMR 1.70 (m, 2H), 2.43 (m, 6), 3.14 (t, 2H), 3.71 (m, 4H), 7.08 (s, 1H), 7.58 (d, 2H), 7.85 (d, 2H); m/z 411.

Method 67

1-[3-(N,N-Dimethylamino)propylthio]-4-bromobenzene 3-(Dimethylamino)propyl chloride hydrochloride (3.48 g, 22 mmol) was added in portions to a suspension of 4-bromothiophenol (3.78 g, 20 mmol) and potassium carbonate (5.52 g, 40 mmol) in DMF (40 ml) and the reaction mixture heated to 60° C. for 15 minutes. The mixture was allowed to cool to ambient temperature and poured into water (100 ml) and extracted with EtOAc (2×100 ml). The extracts were combined, washed with brine (3×100 ml), dried (Chemelut column 1010) and evaporated to give the title compound (5.25 g, 96%) as a pale yellow oil. NMR 1.76 (m, 2H), 2.20 (s, 6H, 2.35 (t, 2H, 2.93 (t, 2H), 7.18 (d, 2H, 7.38 (d, 2H); m/z 276.

Method 68

1-(3,3,3-Trifluoropropylthio)-4-bromobenzene

3-Bromo-1,1,1-trifluoropropane (640 µL, 6 mmol) was added to a mixture of 4-bromothiophenol (945 mg, 5 mmol) and potassium carbonate (760 mg, 5.5 mmol) in DMF (5 ml) and the reaction mixture heated at 40° C. for 1 hour. The mixture was allowed to cool to ambient temperature and poured into water (50 ml) and extracted with EtOAc (2×30 ml). The extracts were combined, washed with brine (3×30 ml), dried (Chemelut column 1010) and evaporated to give the title compound (1.36 g, 95%) as a pale yellow oil. NMR 2.56 (m, 2H), 3.13 (t, 2H, 7.31 (d, 2H), 7.51 (d, 2H), m/z 285 ($M^+$).

Method 69

1-(1-Butylthio)-4-bromobenzene

The title compounds was synthesised in an analogous method to Method 68. NMR 0.85 (t, 3H), 1.38 (m, 2H), 1.51 (m, 2H), 2.96 (t, 2H), 7.23 (d, 2H), 7.46 (d, 2H); m/z 244 ($M^+$).

Method 70

1-[3-(N,N-Dimethylamino)propylsulphonyl]-4-bromobenzene

Oxone (14 g, 23 mmol) was added to a solution of 1-[3-(N,N-dimethylamino)propylthio]-4-bromobenzene (Method 67; 5.24 g, 19.1 mmol) in MeOH (150 ml) and water (30 ml) and the mixture was stirred at ambient temperature for 90 minutes. The reaction mixture was poured onto an Isolute SCX-2 column, washed MeOH (6×40 ml) and the product eluted with 2% methanolic ammonia (10×40 ml). The solvent was evaporated and residue purified by flash chromatography on silica gel eluting with DCM/2% methanolic ammonia (100:0 increasing in polarity to 94:6) to yield the title compound (4.68 g, 80%) as a pale yellow oil. NMR 1.62 (m, 2H), 2.03 (s, 6H), 2.19 (t, 2H), 3.32 (m, 2H), 7.81 (m, 4H); m/z 306.

Method 71

1-(3,3,3-Trifluoropropylsulphonyl)-4-bromobenzene

Oxone (3.7 g, 6 mmol) was added to a solution of 1-(3,3,3-trifluoropropylthio)-4-bromobenzene (Method 68 1.36, 4.75 mmol) in MeOH (25 ml) and water (5 ml) and the mixture was stirred at ambient temperature for 18 hours. The MeOH evaporated and water (20 ml) added and the mixture extracted with DCM. The extracts were dried (Chemelut column CE1005) and solvent removed by evaporation to give the title compound (1.43 g, 95%) as a white solid. NMR 2.62 (m, 2H), 3.67 (m, 2H), 7.86 (s, 4H); m/z 316 ($M^+$).

Method 72

1-(1-Butylsulphonyl)-4-bromobenzene

The title compound was synthesised from Method 69 in an analogous method to Method 71. NMR: 0.80 (t, 3H), 1.31 (m, 2H), 1.47 (m, 2H), 3.29 (t, 2H), 7.78 (d, 2H), 7.86 (d, 2H); m/z 276 ($M^+$).

Method 73

3-Methoxy-1-propanol methanesulphonate

Methanesulphonyl chloride (1.75 ml, 22 mmol) was added to a solution of 3-methoxy-1-propanol (1.81 g, 20 mmol) and triethylamine (3.35 ml, 24 mmol) in DCM (40 ml) cooled in an ice bath and the mixture stirred at ambient temperature for 18 hours. DCM (25 ml) and water (50 ml) were added and the phases separated and the aqueous layer was extracted with DCM (25 ml). The extracts were combined, washed with water (50 ml) and brine (50 ml), dried (Chemelut column CE1010) and evaporated to give the title compound 3.25 g (97%) as a pale yellow oil. NMR 2.00 (m, 2H), 3.01 (s, 3H), 3.35 (s, 3H), 3.49 (t, 2H), 4.38 (t, 2H).

Method 74

1-(3-Methoxypropylsulphonyl)-4-bromobenzene

Potassium carbonate (2.8 g, 20 mmol) was added to a solution of 3-methoxypropan-1-yl methansulphonate (Method 73; 3.25 g, 19.3 mmol) and 4-bromothiophenol (3.48 g, 18.4 mmol) in DMF (30 ml) and the mixture heated at 40° C. for 4 hours. The mixture was allowed to cool to ambient temperature, poured into water (100 ml) and extracted with EtOAc (2×50 ml). The extracts were combined, washed with saturated aqueous sodium hydrogen carbonate solution (50 ml) and brine (2×50 ml), dried (Chemelut column CE1010) and the volatiles removed by evaporation. The residue was dissolved in MeOH (150 ml) and water (30 ml) and oxone (13.4 g, 21.6 mmol) was added in portions. The mixture was stirred at ambient temperature for 18 hours. The MeOH was evaporated, water (50 ml) added and the solution extracted with DCM (3×50 ml). The extracts were combined, washed with brine (50 ml), dried (Chemelut column CE1010), and evaporated. The residue was purified by flash chromatography on silica gel eluting with iso-hexane:EtOAc (100:0 increasing in polarity to 90:10) to give the title compound (3.32 g, 62%) as a colourless oil. NMR 1.95 (m, 2), 3.19 (m, 2H), 3.26 (s, 3H), 3.41 (t, 2H), 7.70 (d, 2H), 7.78 (d, 2H).

Method 75

3-Hydroxyisoxazole

Hydroxylamine hydrochloride (35 g, 0.5 mol) was added to a solution of sodium hydroxide (58 g, 1.45 mol) in water (580 ml). MeOH (600 ml) followed by ethyl propiolate (38 ml, 0.37 mol) in portions was then added and the resulting solution stirred at ambient temperature for 6 days. The mixture was acidified to pH2 with concentrated hydrochloric acid and then saturated with sodium chloride. The solution was extracted with DCM (8×500 ml), the extracts combined, dried and the solvent evaporated. The solid residue was washed with hot iso-hexane (3×300 ml) and the final suspension was allowed to cool and the resulting solid was collected by filtration, dried under vacuum to give the title compound (11.16 g, 35%) as a white solid crystallised. NMR 6.04 (s, 1H), 8.43 (s, 1H), 11.16 (s, 1H) m/z 85 (M+).

Method 76

3-Oxo-2,3-dihydroisothiazole

Glycinamide.HCl (1 mol) was suspended in DMF (500 ml) and $SO_2Cl_2$ (300 ml) was added dropwise over 1.5 hours with cooling keeping the reaction temperature between 5–10° C. The reaction was stirred at 10–15° C. for 6 hours when water (500 ml) was added cautiously. The solid was removed by filtration and the filtrate extracted with ether (2l). The Ethereal solution was washed brine (200 ml) and evaporated in vacuo to yield a pale yellow solid (132 g)—A. The aqueous layer was extracted with DCM (2×600 ml). The DCM portions were combined and washed with ether and water. The organic layer was washed brine and evaporated in vacuo to yield a cream solid (18 g)—B. A & B were combined, dissolved in ether, dried and charcoal was added. The solution was filtered and the filtrate evaporated in vacuo to yield a pale yellow solid (104.3 g). This solid was triturated with isohexane to yield the title compound (91.3 g, 90%). Mpt: 102–5° C.

Method 77

Ethynylcarbamoyl

To liquid ammonia (300 ml) was added methyl propiolate (52.4 g, 0.62 mol) over 2 hours keeping the temperature at −70° C. The ammonia was left to evaporate and the reaction mixture evaporated in vacuo to yield the title compound (43 g) which was used without any further purification. Mpt: 5455° C.

Method 78

3-Oxo-2,3-dihydro-1,2,5-thiadiazole

To a stirred solution of ethynylcarbamoyl (Method 77; 43 g, 0.62 mol) in water (310 ml) cooled in ice bath was added ammonium thiosulphate (92.35 g, 0.62 mol) in one portion. The reaction was allowed to warm to room temperature over 5 hours. To the reaction mixture was added a solution of iodine (79.2 g, 0.31 mol) in MeOH (1 l) rapidly over 10 minutes to yield a dark solution. Ammonium thiosuphate was added until a yellow solution was obtained. The solvent was evaporated to approximately 400 ml and extracted ether (3×300 ml). The ethereal solution was washed brine (100 ml), passed through phase separation paper and evaporated in vacuo to yield the title compound as a pale orange solid (32.8 g, 52%). Mpt: 70–71° C.

Method 79

3-[2-(t-Butoxycarbonylamino)ethoxy]isoxazole

Diisopropyl azodicarboxylate (1.1 ml, 5.5 mmol) was added dropwise to a solution of 2-(t-butoxycarbonylamino) ethanol (850 μl, 5.5 mmol), 3-hydroxyisoxazole (Method 75; 425 mg, 5 mmol) and triphenylphosphine (1.44 g, 5.5 mmol) in THF (20 ml) and the mixture was stirred at ambient temperature for 18 hours. The solvent was evaporated and the residue purified by flash chromatography on silica gel eluting with iso-hexane:EtOAc (100:0 increasing in polarity to 4:1) to give the title compound (506 mg, 44%) as a white solid. NMR 1.43 (s, 9H), 3.56 (m, 2H), 4.32 (m, 2H), 4.90 (s, 1H), 5.98 (s, 1H), 8.16 (s, 1H); m/z 229.

Methods 80–84

The following compounds were synthesised in an analogous method to Method 79 the appropriate amine and heterocycle as starting materials.

| Ex | Compound | NMR | m/z | SM |
|---|---|---|---|---|
| 80 | 3-[2-(t-Butoxycarbonylamino)ethoxy]isothiazole | 1.38 (s, 9H), 3.30 (m, 2H), 4.24 (t, 2H), 6.71 (d, 1H), 6.93 (m, 1H), 8.81 (d, 1H) | 245 | Meth 76 |
| 81 | 3-[2-(t-Butoxycarbonylamino)ethoxy]-1,2,5-thiadiazole | 1.38 (s, 9H), 3.31 (m, 2H), 4.16 (t, 2H), 6.96 (m, 1H), 8.35 (s, 1H) | 246 | Meth 78 |
| 82 | 3-[3-(t-Butoxycarbonylamino)propoxy]isoxazole | 1.36 (s, 9H), 1.80 (m, 2H), 3.04 (q, 2H), 4.17 (t, 2H), 6.24 (s, 1H), 6.83 | 243 | Meth 75 |
| 83 | 3-[3-(t-Butoxycarbonylamino)propoxy]isothiazole | 1.36 (s, 9H), 1.80 (m, 2H), 3.04 (q, 2H), 4.17 (t, 2H), 6.71 (d, 1H), 6.80 (m, 1H), 8.82 (d, 1H) | 259 | Meth 76 |
| 84 | 3-[3-(t-Butoxycarbonylamino)propoxy]-1,2,5-thiadiazole | 1.36 (s, 9H), 1.80 (m, 2H), 3.04 (q, 2H), 4.17 (t, 2H), 6.80 (m, 1H), 8.36 (s, 1H) | 260 | Meth 78 |

Method 85

3-(2-Aminoethoxy)isoxazole hydrochloride

4M Hydrogen chloride in dioxane (10 ml) was added to a solution of 3-[2-(t-butoxycarbonylamino)ethoxy]isoxazole (Method 79; 500 mg, 2.2 mmol) in dioxane (10 ml) and the mixture was stirred at ambient temperature for 3 days. The resulting solid was collected by filtration, washed with ether and dried to give the title compound (298 mg, 83%) as a white solid NMR 3.20 (m, 2H), 4.39 (t, 2H), 6.13 (s, 1H), 8.30 (s, 3H), 8.69 (s, 1H); m/z 129.

Methods 86–90

The following compounds were synthesised in an analogous method to Method 85.

| Ex | Compound | NMR | m/z | SM |
|---|---|---|---|---|
| 86 | 3-(2-Aminoethoxy)isothiazole hydrochloride | 3.19 (m, 2H), 4.46 (t, 2H), 6.76 (d, 1H), 7.28 (s, 1H), 8.40 (s, 3H), 8.87 (d, 1H) | 145 | Meth 80 |
| 87 | 3-(2-Aminoethoxy)-1,2,5-thiadiazole hydrochloride | 3.20 (m, 2H), 4.58 (t, 2H), 8.36 (m, 4H) | 146 | Meth 81 |
| 88 | 3-(3-Aminopropoxy)isoxazole hydrochloride | 2.02 (m, 2H), 2.83 (m, 2H), 4.24 (t, 2H), 6.29 (s, 1H), 8.20 (s, 3H), 8.61 (s, 1H) | 143 | Meth 82 |

-continued

| Ex | Compound | NMR | m/z | SM |
|---|---|---|---|---|
| 89 | 3-(3-Aminopropoxy)isothiazole hydrochloride | 2.02 (m, 2H), 2.83 (m, 2H), 4.36 (t, 2H), 6.78 (d, 1H), 8.10 (s, 3H), 8.81 (d, 1H) | 159 | Meth 83 |
| 90 | 3-(3-Aminopropoxy)-1,2,5-thiadiazole hydrochloride | 2.02 (m, 2H), 2.83 (m, 2H), 4.43 (t, 2H), 8.10 (s, 3H), 8.39 (s, 1H) | 160 | Meth 84 |

Methods 91–94

The following compounds were synthesised by the procedure as described in JOC 1987, 2714–2716.

| Method | Compound |
|---|---|
| 91 | 5-Methyl-4-(methylamino)isoxazole hydrochloride |
| 92 | 5-Acetyl-2-(trifluoromethyl)imidazole |
| 93 | 5-Acetyl-2-(methoxymethyl)imidazole |
| 94 | N-(5-Methyl-4-isoxazolyl)-2,2,2-trifluoroacetamide |

Methods 95–109

The following compounds were prepared using procedures analogous to those described in JOC 1987, 2714–2726.

| Ex | Compound | NMR | m/z | SM |
|---|---|---|---|---|
| 95 | 5-Methyl-4-(N-methyl-N-propionylamino)isoxazole | 1.09 (t, 3H), 2.08 (q, 2H), 2.38 (s, 3H), 3.16 (s, 3H), 8.16 (s, 1H) | 169 | Meth 91 |
| 96 | 1-Methyl-2-ethyl-5-acetylimidazole | 1.36 (t, 3H), 2.41 (s, 3H), 2.72 (q, 2H), 3.82 (s, 3H), 7.72 (s, 1H) | 153 | Meth 95 |
| 97 | 5-Methyl-4-(N-methyl-N-isobutyrylamino)isoxazole | 1.03 (d, 6H), 2.36 (s, 3H), 2.48 (m, 1H), 3.16 (s, 3H), 8.20 (s, 1H) | 183 | Meth 91 |
| 98 | 1-Methyl-2-isopropyl-5-acetylimidazole | 1.36 (d, 6H), 2.42 (s, 3H), 3.10 (m, 1H), 3.84 (s, 3H), 7.75 (s, 1H) | 167 | Meth 97 |
| 99 | 4-(Isopropylamino)-5-methylisoxazole | CDCl$_3$ 1.12 (d, 6H), 2.30 (s, 3H), 3.21 (1H, septuplet), 8.01 (s, 1H) | 141 | 4-amino-5-methylisoxazole |
| 100 | 5-Methyl-4-(N-isopropylacetamido)isoxazole | CDCl$_3$ 1.02 (brs, 6H), 1.80 (s, 3H), 2.38 (s, 3H), 4.99 (1H, septuplet), 8.09 (s, 1H) | 183 | Meth 99 |
| 101 | 5-Acetyl-1-isopropyl-2-methylimidazole | 1.40 (d, 6H), 2.38 (s, 3H), 2.42 (s, 3H), | 167 | Meth 100 |
| | | 5.08 (brm, 1H), 7.81 (s, 1H) | | |
| 102 | 3,5-Dimethyl-4-amino-isoxazole | 2.04 (s, 3H), 2.19 (s, 3H), 3.78 (s, 2H) | 112 | |
| 103 | N-(2,2,2-Trifluoroethyl)-5-methyl-4-aminoisoxazole | (CDCl) 2.32 (s, 3H), 2.80 (s, 1H), 3.52 (q, 2H), 8.06 (s, 1H) | 181 | Meth 94 |
| 104 | 3,5-Dimethyl-4-formamidoisoxazole | 2.08 (s, 3H), 2.23 (s, 3H), 8.10 (s, 1H), 9.50 (s, 1H) | 140 | Meth 102 |
| 105 | 3,5-Dimethyl-4-methylaminoisoxazole | 2.08 (s, 3H), 2.30 (s, 3H), 2.60 (d, 3H), 3.84 (s, 1H) | n/a | Meth 104 |
| 106 | 3,5-Dimethyl-4-(N-methylacetamido)isoxazole | 1.75 (s, 3H), 2.16 (s, 3H), 2.30 (s, 3H), 3.00 (s, 3H) | 168 | Meth 105 |
| 107 | 1,2,4-Trimethyl-5-acetylimidazole | 2.26 (s, 3H), 2.38 (s, 6H), 3.65 (s, 3H) | 152 | Meth 106 |
| 108 | N-(2,2,2-Trifluoroethyl)-N-(5-methyl-4-isoxazolyl)acetamide | 1.82 (s, 3H), 2.37 (s, 3H), 4.36 (q, 2H), 8.62 (s, 1H) | 223 | Meth 103 |
| 109 | 1-(2,2,2-Trifluoroethyl)-2-methyl-5-acetylimidazole | 2.38 (s, 6H), 5.31 (q, 2H), 7.96 (s, 1H) | 207 | Meth 108 |

Method 110

N-Methyl-4-aminobenzenesulphonamide

4-Aminobenzenesulphonylfluoride (200 mg, 1.14 mmol) was dissolved in a solution of methylamine in EtOH (3 mL, excess) and heated to 80° C. for 45 minutes, then cooled to room temperature and left to stir overnight. The solvent was evaporated in vacuo and azeotroped with ether to yield the title compound as a solid (160 mg, 75%). NMR: 2.12 (s, 3H), 5.85 (s, 2H), 6.59 (d, 2H), 7.37 (d, 2H); m/z 187.

Method 111

2-Amino-4-(1,2-dimethylimidazol-5-yl)-5-chloropyrimidine

2-Amino-4-(1,2-dimethylimidazol-5-yl)pyrimidine (Method 26; 378 mg, 2 mmol) and N-chlorosuccimide (267 mg, 2 mmol) were dissolved in glacial acetic acid (7 ml) under an atmosphere of nitrogen. The reaction mixture was heated at 65° C. for 18 hours when further N-chlorosuccinimide (89 mg, 0.66 mmol) was added and the reaction heated at 65° C. for an additional 2 hours. The volatiles were removed by evaporation and the residue dissolved in water (10 ml). The solution was adjusted to pH 11–12 by addition of 40% aqueous sodium hydroxide solution. The precipitated solid was collected by filtration and washed sparingly with water, dried under vacuum at 60° C. to give the title compound (344 mg, 77%) as a yellow solid. NMR 2.35 (s, 3H, 3.75 (s, 3H), 4.83 (s, 2H), 7.53 (s, 1H), 8.27 (s, 1H); m/z 224.

Example 166

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph. Eur | 488.5 |
| Magnesium stearate | 1.5 |

| (e): Injection I | (50 mg/ml) |
|---|---|
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1 M Sodium hydroxide solution | 15.0% v/v |
| Water for injection | to 100% |

| (g): Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note
The above formulations maybe obtained by conventional procedures well known in the pharmaceutical art. The tablets (a)–(c) may be enteric coated by conventional means, for example to provide a coating of cellulose acetate phthalate.

What is claimed is:
1. A compound of formula (I):

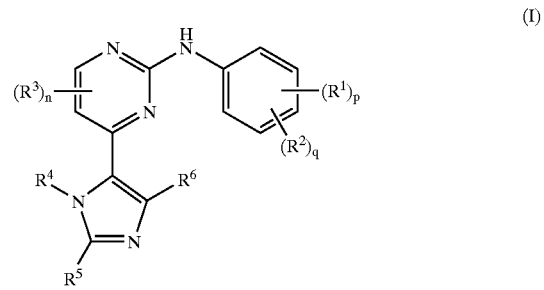

wherein:

$R^1$ is halo, nitro, cyano, hydroxy, amino, carboxy, carbamoyl, mercapto, $C_{1-6}$alkyl, $C_{1-6}$alkoxy, $C_{2-6}$alkenyl or $C_{2-6}$alkynyl;

p is 0–4; wherein the values of $R^1$ may be the same or different;

$R^2$ is sulphamoyl or a group $R^a$—$R^b$—;

q is 0–2; wherein the values of $R^2$ maybe the same or different; and wherein p+q=0–5;

$R^3$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N-($C_{1-3}$alkyl)amino, N,N-($C_{1-3}$alkyl)$_2$amino, $C_{1-3}$alkanoylamino, N-($C_{1-3}$alkyl)carbamoyl, N,N-($C_{1-3}$alkyl)$_2$carbamoyl, $C_{1-3}$alkylS(O)$_a$ wherein a is 0 to 2, N-($C_{1-3}$alkyl)sulphamoyl or N,N-($C_{1-3}$alkyl)$_2$sulphamoyl; wherein $R^3$ may be optionally substituted on carbon by one or more $R^c$;

n is 0 to 2, wherein the values of $R^3$ may be the same or different;

$R^4$ is hydrogen, $C_{1-6}$alkyl, $C_{2-6}$alkenyl, $C_{2-6}$alkynyl, $C_{3-8}$cycloalkyl, phenyl or a carbon-linked heterocyclic group; wherein $R^4$ may be optionally substituted on carbon by one or more $R^d$; and wherein if said heterocyclic group contains an —NH— moiety that nitrogen may be optionally substituted by a group selected from $R^n$;

$R^5$ and $R^6$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$ amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, $C_{1-6}$alkylsulphonylamino, $C_{3-8}$cycloalkyl or a 4–7 membered saturated heterocyclic group; wherein $R^5$ and $R^6$ independently of each other may be optionally substituted on carbon by one or more $R^e$; and wherein if said 4–7 membered saturated heterocyclic group contains an —NH— moiety that nitrogen may be optionally substituted by a group selected from $R^f$;

$R^a$ is selected from $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, a heterocyclic group, phenyl$C_{1-6}$alkyl or (heterocyclic group)$C_{1-6}$alkyl; wherein $R^a$ may be optionally substituted on carbon by one or more $R^g$; and wherein if said heterocyclic group contains an —NH— moiety that nitrogen may be optionally substituted by a group selected from $R^h$;

$R^b$ is —C(O)—, —N($R^m$)C(O)—, —C(O)N($R^m$)—, —S(O)$_r$—, —OC(O)N($R^m$)SO$_2$—, —SO$_2$N($R^m$)— or —N($R^m$)SO$_2$—; wherein $R^m$ is hydrogen or $C_{1-6}$alkyl optionally substituted by one or more $R^i$ and r is 1–2;

$R^d$, $R^g$ and $R^i$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkoxy$C_{1-6}$alkoxy, $C_{1-6}$alkoxy$C_{1-6}$alkoxy$C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, $C_{1-6}$alkylsulphonylamino, $C_{3-8}$cycloalkyl, phenyl, heterocyclic group, phenyl$C_{1-6}$ alkyl-$R^o$—, (heterocyclic group)$C_{1-6}$alkyl-$R^o$—, phenyl-$R^o$— or (heterocyclic group)-$R^o$—; wherein $R^d$, $R^g$ and $R^i$ independently of each ether may be optionally substituted on carbon by one or more $R^j$; and wherein if said heterocyclic group contains an —NH— moiety that nitrogen may be optionally substituted by a group selected from $R^k$;

$R^o$ is —O—, —N($R^p$)—, —C(O)—, —N($R^p$)C(O)—, —C(O)N($R^p$)—, —S(O)$_s$—, —SO$_2$N($R^p$)— or —N($R^p$)SO$_2$—; wherein $R^p$ is hydrogen or $C_{1-6}$alkyl and s is 0–2;

$R^f$, $R^h$, $R^k$ and $R^n$ are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)carbamoyl, benzyl, benzyloxycarbonyl, benzoyl and phenylsulphonyl; wherein $R^f$, $R^h$, $R^k$ and $R^n$ independently of each other may be optionally substituted on carbon by on or more $R^i$; and $R^e$, $R^e$, $R^i$ and $R^j$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt or an in vivo hydrolysable ester thereof.

2. A compound of formula (I) according to claim 1 wherein $R^1$ is halo, amino, $C_{1-6}$alkyl or $C_{1-6}$alkoxy or a pharmaceutically acceptable salt or an in vivo hydrolysable ester thereof.

3. A compound of formula (I) according to claim 1 wherein p is 0–2; wherein the values of $R^1$ maybe the same or different or a pharmaceutically acceptable salt or an in vivo hydrolysable ester thereof.

4. A compound of formula (I) according to claim 1 wherein $R^2$ is sulphamoyl or a group $R^a$—$R^b$—; wherein $R^a$ is selected from $C_{1-6}$alkyl, $C_{2-6}$alkenyl, $C_{2-6}$alkynyl, $C_{3-8}$cycloalkyl, phenyl or a heterocyclic group; wherein $R^a$ may be optionally substituted on carbon by one or more $R^g$;

$R^b$ is —N($R^m$)C(O)—, —C(O)N($R^m$)—, —S(O)$_r$—, —OC(O)N($R^m$)SO$_2$—, —SO$_2$N($R^m$)— or —N($R^m$)SO$_2$—; wherein $R^m$ is hydrogen or $C_{1-6}$alkyl and r is 2;

$R^g$ is selected from halo, hydroxy, amino, cyano, carbamoyl, $C_{1-6}$alkyl, $C_{1-6}$alkoxy, $C_{1-6}$alkoxy$C_{1-6}$ alkoxy, $C_{1-6}$alkoxy$C_{1-6}$alkoxy$C_{1-6}$alkoxy, N,N-($C_{1-6}$alkyl)$_2$amino, $C_{1-6}$alkylS(O)$_a$ wherein a is 2, $C_{3-8}$cycloalkyl, phenyl, heterocyclic group, phenyl$C_{1-6}$alkyl-$R^o$— or (heterocyclic group)-$R^o$—; wherein $R^g$ may be optionally substituted on carbon by one or more $R^j$;

$R^o$ is —O—; and $R^j$ is selected from halo, hydroxy, methyl or methoxy;

or a pharmaceutically acceptable salt or an in vivo hydrolysable ester thereof.

5. A compound of formula (I) according to claim 1 wherein q is 0 or 1 or a pharmaceutically acceptable salt or an in vivo hydrolysable ester thereof.

6. A compound of formula (I) according to claim 1 wherein q is 1 and $R^2$ is para to the —NH— of the aniline of formula (I) or a pharmaceutically acceptable salt or an in vivo hydrolysable ester thereof.

7. A compound of formula (I) according to claim 1 wherein $R^3$ is halo or a pharmaceutically acceptable salt or an in vivo hydrolysable ester thereof.

8. A compound of formula (I) according to claim 1 wherein n is 0 or 1 or a pharmaceutically acceptable salt or an in vivo hydrolysable ester thereof.

9. A compound of formula (I) according to claim 1 wherein $R^4$ is hydrogen, $C_{1-6}$alkyl or $C_{2-6}$alkenyl; wherein $R^4$ may be optionally substituted on carbon by one or more $R^d$; wherein $R^d$ is selected from halo, amino, $C_{1-6}$alkoxy, $C_{1-6}$alkanoylamino, $C_{1-6}$alkylsulphonylamino, phenyl or heterocyclic group;

or a pharmaceutically acceptable salt or an in vivo hydrolysable ester thereof.

10. A compound of formula (I) according to claim 1 wherein $R^5$ and $R^6$ are independently selected from hydrogen or $C_{1-6}$alkyl; wherein $R^5$ and $R^6$ independently of each other may be optionally substituted on carbon by one or more $R^e$; wherein $R^e$ is selected from halo or methoxy;

or a pharmaceutically acceptable salt or an in vivo hydrolysable ester thereof.

11. A compound of formula (I) according to claim 1 wherein:

$R^1$ is chloro, amino, methyl or methoxy;

p is 0–2; wherein the values of $R^1$ may be the same or different;

$R^2$ is sulphamoyl, N-(tetrahydrofur-2-ylmethyl) sulphamoyl, N-(cyclopropylmethyl)sulphamoyl, N-(fur-2-ylmethyl)sulphamoyl, N-(2,2-dimethyl-1,3-dioxolan-4-ylmethyl)sulphamoyl, N-(cyanomethyl) sulphamoyl, N-(carbamoylmethyl)sulphamoyl, N-methylsulphamoyl, N-(4-fluorobenzyl)sulphamoyl, N-(pyridin-2-ylmethyl)sulphamoyl, N-(pyridin-3-ylmethyl)sulphamoyl, N-(4-methylthiazol-2-yl) sulphamoyl, N-(3-methylisoxazol-5-ylmethyl) sulphamoyl, N-(tetrahydropyran-2-ylmethyl) sulphamoyl, N-(2-methylpyrazin-5-yl)sulphamoyl, N-[2-(2-hydroxyethoxy)ethyl]sulphamoyl, N-(2-hydroxyethyl)sulphamoyl, N-(2,2,2-trifluoroethyl) sulphamoyl, N-(2-methoxyethyl)sulphamoyl, N-(2-mesylethyl)sulphamoyl, N-(2-benzyloxyethyl) sulphamoyl, N-(2,2-dimethoxyethyl)sulphamoyl, N-[2-(N,N-dimethylamino)ethyl]sulphamoyl, N-(2-piperidin-1-ylethyl)sulphamoyl, N-[2-(methoxymethoxy)ethyl]sulphamoyl, N-ethylsulphamoyl, N-[2-(2-methoxyethoxy)ethyl]sulphamoyl, N-{2-[2-(2-methoxyethoxy)ethoxy]ethyl}sulphamoyl, N-(2-{2-[2-(2-methoxyethoxy)ethoxy]ethoxy}ethyl)sulphamoyl, N-(2-pyridin-2-ylethyl)sulphamoyl, N-(2-pyridin-4-ylethyl)sulphamoyl, N-(2-isoxazol-3-yloxyethyl)sulphamoyl, N-(2-isothiazol-3-yloxyethyl)sulphamoyl, N-(2-1,2-5-thiadiazol-3-yloxyethyl)sulphamoyl, N-methyl-N-(2-methoxyethyl)sulphamoyl, N-[3-(2-oxopyrrolidin-1yl)propyl]sulphamoyl, N-(3-methoxypropyl)sulphamoyl, N-propylsulphamoyl, N-(2,3-dihydroxypropyl)sulphamoyl, N-(3-morpholinopropyl)sulphamoyl, N-[3-(N,N-dimethylamino)propyl]sulphamoyl, N-(3,3,3-trifluoropropyl)sulphamoyl, N-(2,2-dimethyl-3-hydroxypropyl)sulphamoyl, N-(3-hydroxypropyl)sulphamoyl, N-(3-ethoxypropyl)sulphamoyl, N-(2-hydroxypropyl)sulphamoyl, N-(3-isopropoxypropyl)sulphamoyl, N-(3-isopropoxy-2-hydroxypropyl)sulphamoyl, N-(3-isoxazol-3-yloxypropyl)sulphamoyl, N-(3-isothiazol-3-yloxypropyl)sulphamoyl, N-(3-1,2-5-thiadiazol-3-yloxypropyl)sulphamoyl, N-(1,1-dimethylpropyl)sulphamoyl, N-methyl-N-(3-morpholinopropyl)sulphamoyl, N-butylsulphamoyl, N-t-butylsulphamoyl, N-(2-hydroxybutyl)sulphamoyl, N-methyl-N-t-butylsulphamoyl, N-pentylsulphamoyl, N-(5-hydroxypentyl)sulphamoyl, N-(4,5-dimethyloxazol-2-yl)sulphamoyl, N-(cyclopropyl)sulphamoyl, N-(cyclobutyl)sulphamoyl, N-(3-trifluoromethylphenyl)sulphamoyl, N-allylsulphamoyl, N-(2-propynyl)sulphamoyl, N-methylcarbamoyl, acetamido, mesylamino or mesyl;

q is 0 or 1;

$R^3$ is bromo or chloro;

n is 0 or 1;

$R^4$ is hydrogen, methyl, ethyl, isopropyl, 3-butenyl, benzyl, 2-phthalimidoethyl, 2-aminoethyl, 2-methoxyethyl, 2-acetamidoethyl, 2-mesylaminoethyl or 2,2,2-trifluoroethyl;

$R^5$ and $R^6$ are independently selected from hydrogen, methyl, ethyl, isopropyl, trifluoromethyl or methoxymethyl;

or a pharmaceutically acceptable salt or an in vivo hydrolysable ester thereof.

12. A compound according to claim 1 selected from:

2-{4-[N-(cyclopropylmethyl)sulphamoyl]anilino}-4-(1,2-dimethylimidazol-5-yl)pyrimidine;

4-(1-ethyl-2-methylimidazol-5-yl)-2-{4-[N-(2-methoxyethyl)sulphamoyl]anilino}pyrimidine 4-(1-ethyl-2-methylimidazol-5-yl)-2-{4-[N-(3-methoxypropyl)sulphamoyl]anilino}pyrimidine;

4-(1-ethyl-2-methylimidazol-5-yl)-2-{4-[N-(cyclopropylmethyl)sulphamoyl]anilino}pyrimidine;

4-(1-ethyl-2-methylimidazol-5-yl)-2-[4-(N-cyclopropylsulphamoyl)anilino]pyrimidine;

4-(1-methyl-2-isopropylimidazol-5-yl)-2-{4-[N-(cyclopropylmethyl)sulphamoyl]anilino}pyrimidine;

4-(1,2-dimethylimidazol-5-yl)-2-[4-(N-cyclopropylsulphamoyl)anilino]pyrimidine;

4-(1,2-dimethylimidazol-5-yl)-2-[4-(N-cyclobutylsulphamoyl)anilino]pyrimidine;

4-(1,2-dimethylimidazol-5-yl)-2-{4-[N-(2,2,2-trifluoroethyl)sulphamoyl]anilino}pyrimidine; and 4-(1-isopropyl-2-methylimidazol-5-yl)-2-[4-(N-cyclobutylsulphamoyl)anilino]pyrimidine;

or a pharmaceutically acceptable salt or an in vivo hydrolysable ester thereof.

13. A pharmaceutical composition which comprises a compound of the formula (I), or a pharmaceutically acceptable salt or in vivo hydrolysable ester thereof, as claimed in any one of claims 1–12 in association with a pharmaceutically-acceptable diluent or carrier.

14. A process for preparing a compound of formula (I) or a pharmaceutically acceptable salt or an in vivo hydrolysable ester thereof (wherein $R^1$, $R^2$, $R^3$, $R^4$, $R^5$, $R^6$, n, p and q are, unless otherwise specified, as defined in claim 1), which process comprises:

Process a)

reaction of a pyrimidine of formula (II):

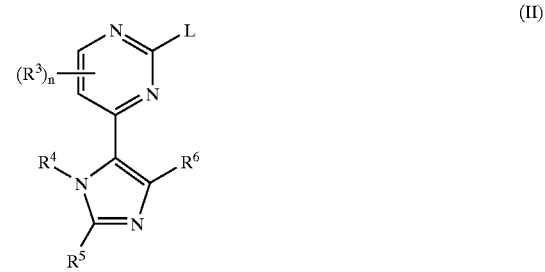

(II)

wherein L is a displaceable group; with an aniline of formula (III):

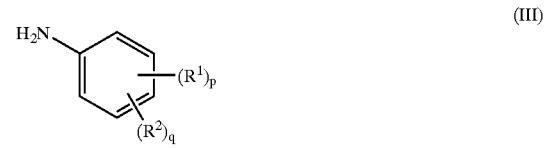

(III)

or

Process b)

reacting a compound of formula (IV):

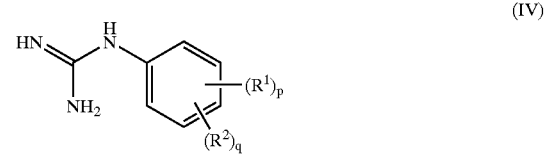

(IV)

with a compound of formula (V):

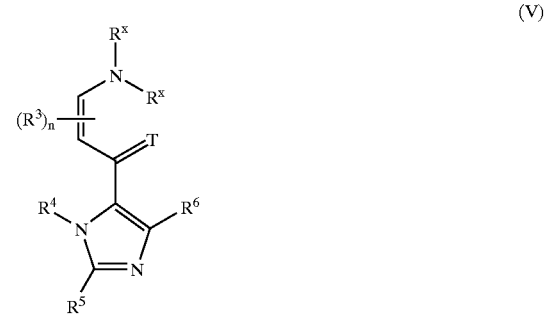

(V)

wherein T is O or S; $R^x$ may be the same or different and is selected from $C_{1-6}$alkyl; or Process c)

for compounds of formula (I) where $R^2$ is sulphamoyl or a group $R^a$—$R^b$— and $R^b$ is —$NHSO_2$—; reacting a pyrimidine of formula (VI):

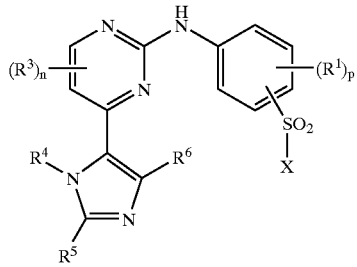

(VI)

wherein X is a displaceable group; with an amine of formula (VII):

$R^a$—$NH_2$     (VII)

or

Process d)

for compounds of formula (I); reacting a pyrimidine of formula (VIII):

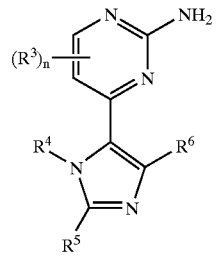

(VIII)

with a compound of formula (IX):

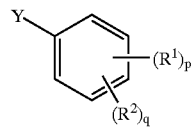

(IX)

where Y is a displaceable group;
and thereafter optionally:
  i) converting a compound of the formula (I) into another compound of the formula (I);
  ii) removing any protecting groups;
  iii) forming a pharmaceutically acceptable salt or in viva hydrolysable ester.

15. A method for inhibiting cyclin-dependent kinase CDK2, CDK4 or CDK6 in a warm-blooded animal, which comprises administering to said animal an inhibitory amount of a compound of formula (I) or a pharmaceutically acceptable salt or in vivo hydrolysable ester thereof as claimed in any one of claims 1–12.

* * * * *